US012083094B2

(12) United States Patent
Mills et al.

(10) Patent No.: US 12,083,094 B2
(45) Date of Patent: Sep. 10, 2024

(54) CANNABINOID COMPOSITION AND METHODS OF TREATMENT USING THE SAME

(71) Applicant: CANNPAL ANIMAL THERAPEUTICS LIMITED, New South Wales (AU)

(72) Inventors: Layton Patrick Mills, New South Wales (AU); Margaret Ann Curtis, New South Wales (AU); Rayson Tan, New South Wales (AU)

(73) Assignee: CANNPAL ANIMAL THERAPEUTICS LIMITED, New South Wales (AU)

( * ) Notice: Subject to any disclaimer, the term of this patent is extended or adjusted under 35 U.S.C. 154(b) by 776 days.

(21) Appl. No.: 17/252,483

(22) PCT Filed: Jun. 14, 2019

(86) PCT No.: PCT/AU2019/050615

§ 371 (c)(1),
(2) Date: Dec. 15, 2020

(87) PCT Pub. No.: WO2019/237156

PCT Pub. Date: Dec. 19, 2019

(65) Prior Publication Data

US 2021/0361613 A1 Nov. 25, 2021

(30) Foreign Application Priority Data

Jun. 15, 2018 (AU) ................................ 2018902143
May 3, 2019 (AU) ................................ 2019901525

(51) Int. Cl.

*G16H 20/13* (2018.01)
*A61K 9/00* (2006.01)
*A61K 31/05* (2006.01)
*A61K 31/352* (2006.01)
*A61K 47/14* (2017.01)
*A61P 25/04* (2006.01)

(52) U.S. Cl.

CPC .......... *A61K 31/352* (2013.01); *A61K 9/0053* (2013.01); *A61K 31/05* (2013.01); *A61K 47/14* (2013.01); *A61P 25/04* (2018.01); *G16H 20/13* (2018.01)

(58) Field of Classification Search

CPC ....... G16H 20/13; A61P 25/04; A61K 31/352; A61K 31/05; A61K 9/0053; A61K 47/14

See application file for complete search history.

(56) References Cited

FOREIGN PATENT DOCUMENTS

| | | | | |
|---|---|---|---|---|
| AU | 2018101357 | A4 | 10/2018 | |
| CA | 3006182 | A | 6/2017 | |
| WO | WO 2004/016246 | A1 | 2/2004 | |
| WO | WO 2016/064987 | A1 | 4/2016 | |
| WO | WO 2016/084075 | A1 | 6/2016 | |
| WO | WO 2016/092539 | A1 | 6/2016 | |
| WO | WO 2016/094810 | * | 6/2016 | ........... A61K 31/352 |
| WO | WO 2016/094810 | A2 | 6/2016 | |
| WO | WO 2016/199148 | A1 | 12/2016 | |
| WO | WO 2017/007833 | A1 | 1/2017 | |
| WO | WO 2017/145160 | A1 | 8/2017 | |
| WO | WO 2018/102029 | A1 | 6/2018 | |
| WO | WO 2018/175259 | A1 | 9/2018 | |
| WO | WO 2019/104442 | A1 | 6/2019 | |

OTHER PUBLICATIONS

"SAVITEX® nabiximols"; https://www.tga.gov.au/sites/dfault/files/auspar-nabiximois-130927-pi.pdf; accessed Dec. 15, 2020; 18 pages.

Matthew E. Miller; "CBD for dogs: Everything You Need to Know"; https://www.petmd.com/dog/general-health/cannabis-oil-dogs-everything-you-need-know; PETMD; Apr. 2017; accessed Dec. 15, 2020; 9 pages.

Karniol et al.; "Cannabidiol Interferes with the Effects of Δ9—Tetrahydrocannabinol in Man"; European Journal of Pharmacology; vol. 28; 1974; p. 172-177.

International Patent Application No. PCT/AU2019/050615; Int'l Search Report and the Written Opinion; dated Jul. 24, 2019; 15 pages.

* cited by examiner

*Primary Examiner* — Erich A Leeser
(74) *Attorney, Agent, or Firm* — BakerHostetler

(57) ABSTRACT

The invention relates to a liquid composition comprising a combination of $\Delta^9$-tetrahydrocannabinol (THC) and cannabidiol (CBD) and an oral delivery system, methods of treating pain, inflammation and/or anxiety in a subject and methods of controlling a heart rate of a subject comprising orally administering the liquid composition, as well as downregulating or upregulating expression of particular related genes.

16 Claims, 13 Drawing Sheets

Specification includes a Sequence Listing.

SEQUENCE LISTING

```
<160> NUMBER OF SEQ ID NOS: 5

<210> SEQ ID NO 1
<211> LENGTH: 5341
<212> TYPE: DNA
<213> ORGANISM: Canis familiaris

<400> SEQUENCE: 1

taactcagga agtttaaaag tcatacaaaa attaggtggc tgaaccagag tttgaaccta     60

gatgctttta tctactacac atacactgct tactttccca ttaaatacca cttcatccca    120

ccccaaccaa gtagtcctag ggaaccactt cctggagcat agacatatct tcattcacct    180

gtccttgagc aatgtcttta tgtagaatgt gctgtttttc tccattttct cattcttcaa    240
```

-continued

```
cattttgctc acactgctta tggaatattc tgtccttatg cccttgttga aattaatcta    300
ttagagccac ttatctgtct tcaataaaag tggttgacaa gattgccttc tctatcattg    360
caacacatgt aatttaccta aagaaatgac cttgccctaa aaaagtaatc ataaatgacc    420
ttactctaac aaccgtcaga tagtacaaca ataaatttat ttatacatgg aaaagtacaa    480
ctgataatgt atcaaagaag cttgaatatt taacaaatat ttttaaacat gttttaaaac    540
acatatgttt taaataaaat gaattaaatc atgttaaaga tcaaatagaa cttcgaacat    600
gccaaaattc tgatgagaca aatttgatga tgactcactt ctgccctcaa agggcaggag    660
gttggttgca tattgtggaa tttcctctga cataattgaa gaatgaggct gcatattctc    720
tgctgctctg aataatataa aatgccacag aagctctcca tccaacagaa gtcctttggg    780
acagcagagc tcacaagcgt ctgggacaag agccagaaag aaaccagaac gaaggcacct    840
tgtgtaaaca tgacttccaa gctggctgtt gctctcttgg cagcttttgt cctttctgca    900
gctctctgtg aaggtaagca gacttttctg gtttacagag ttttcctgtg tctgaatgtg    960
atcctcagat agcaagatta cccttaatgc tttaataaca aatatccttt ttattcaagt   1020
aaaggaaata atatttgcag tcacttaaca ttaaattgaa gctttgttta gattttatct   1080
ctacaacact tagaaaagta taaagtttaa ttaatataga catcttgttc ctattttccg   1140
tgctctatag gatgtttaca tataaatgca ttaatataaa tctatagagc gtatcttttt   1200
aaaaagatat atttatttat ttttagagag tgagagaaag gtgggggggt agagacggag   1260
agagagagag agagagagag agagagagaa tttcaagcag actcccagct gagtgtggag   1320
cccaatgtgg ggcccaatct aaccaccctg agatcatgac ctgagcctaa atcaggtgtg   1380
agatgcttaa ccaactgagc gccctagagt atatcttatt agggccacaa ttactcatat   1440
tatttattaa tattgagcag ataactcagg taattttact acatgtactg ttttattgac   1500
gaacttcaga caactatcat ttcctgtttg gtttaaagac aacaccccaa caaattgtaa   1560
atcttcttgg aatccctccc atgaaagaaa tacagttaga aatgtttata gcatagagtt   1620
cttacatttt tctttttttct gctaagcatt aaagattttg ctaagatctg agacatcttt   1680
gtgcaatttc tattgctatt aattctttcc aaaggcaatt tttctgttac tgaattttag   1740
gttatatcct ataaatagca ttgtggtatc atagaagatt acacaatatc aagtagaaaa   1800
aaaagtacca taaggatgtc aacatttcac aaagtcaact ccaagtctta tgcaggaagt   1860
caatcaatgt tgtcattaat gacagcattt ttttttttaa ctgaatttag gggctaggag   1920
aatatccagc cttctccttc aagaattagt ttactaaaga tgtgatgttt accaaacata   1980
cagttaccaa attatcaact tggaattaag gagagaaagt aagtgaccag cagagtcatg   2040
tttgtgatga aattaatcct agcttttatt attttttcac agctgcagtt ctgtcaagag   2100
tcagttcaga acttcgatgc cagtgtataa aaacacactc cacacctttc catcccaaat   2160
atattaaaga actgagagtg attgacagtg gcccacattg tgaaaactca gaaatcatgt   2220
aagtactttc aaaagatatt ttacttcggc aaatccataa ttgaggaagg tggaaatatc   2280
caacaaaatt ctaggtgtag gaatacaata gtgggcagaa cagaaaggaa agattctttg   2340
tctctatgac atttaaatat ggtaccttcc attcaccata gttaaaaatg tcttggaccc   2400
acattttatg gttatactac aggaactaca acttgaaggg caaagggatg tctgaaacct   2460
gctaaatact gatttagtca tatctctttt atttcagtgt aaagcttttc aatggaaatg   2520
aggtgtgcct ggaccccaag gaaaaatggg tacaaaaggt tgtgcagata tttctaaaga   2580
agtaagtttt tttttttttt aactttagat tcttcattta ccctgagaca tatagtctaa   2640
```

atgttagcct ataaatttcc tcttgctgct ggaagtctac tcttttggaa atttgcctct 2700
ttaattaaaa aacaaaaaaa tagtagcaat agtgagtttg ttgtactcat aactgggaag 2760
accatacatg tcagtttgtc cagtgaagtc tgggcttatg cctgtgccct gtatcagtga 2820
tatggttccc tttcattctc agaagtgttc tggtttagat gataatttat ctttctactc 2880
ataattgaaa attagagtat ttctaacaca tgaatatctg agattattta tttccatagt 2940
atatatattt tcaagaatga tactttcctc cttattagac atttaattaa aatttgtttt 3000
attttattta ttttcagggc tgagaaacaa gatccgtgaa acaacaaaca cattctctgt 3060
ggtttccaag aattcctcag gaaagatgcc aatgagactt caaaaaaatc tatttcagta 3120
cttcatgtcc cgtgtagacc tggtgtagga ttgccagata aaaatacagt atgcccagtt 3180
agatttgaat attaagtaaa acaatgaata gttttttttct aaagtctcat atatgttgcc 3240
ctattcaatg tctaggcaca cttacattaa acatattatt cattgtttgc tgtaaattca 3300
aatgtagctg gaaatcctgg atatattttg ttgttgttac atctttccac ctcacctaca 3360
ggccaggatg catgagtccc ttttcaacct tgccttggtc tcttctttat tcctcaactg 3420
gagaaaaggt atcagcaagc atcctacctc acagaaatat gaggacatat ggaagcactt 3480
taactttttc tcatgttgtc taaattatgt tcaagtgaaa cttgtttgcc tatttattat 3540
ttatgtattt atttaagaaa caaatatggg aatatctgtg cataaatttg gaaaaatagg 3600
aaaggaagca ttgttgataa gttagtataa tgatggtagt gaatttatat ttattttggt 3660
atttagtgat gttatattaa agaactattt tgtttttttt ttttttaaag aactattttg 3720
aacaaggttg ctagatttag caaaattaaa aatgagatac tcatttaatt ttgatttcaa 3780
acaataattt tttattatat tattatttat ctgaaatttc aattgaaccg caatcctact 3840
tttgatactc ctagtcttgt ctattcactg acagccttgt tcaatgctgg gttgaatgat 3900
cagaaccctg agttagaatt gtttctccaa agagcaaaaa ctcgacaagc aatattaatg 3960
aagtaatttc ttgccagtta aaatttgtat atttataata tacaaataga ttcttataat 4020
tttacttatt gtgttcttaa acactgactt ttttgacttt aagatgcttt tatatgttcc 4080
ccaagagatt ttttttccta ctatttttga tgctatggaa atagaaatgt aaaatattta 4140
aaataaaact tattgtcaaa gtcatcaggt gtttgtcttt ctttggtagt tattgattta 4200 ttttttttaca ttaaaaataa tattttgagt tgaaaagcat agatgcttgg ggttcctggg 4260
tggcttagtc agttaagtgt ttgactcttg gtttcagctc aggccacgat ctcagaatcc 4320
tgagacccag ccctgcatag atttccacac ttggcatgga ggctgcttgg gattctcact 4380
ctcccttggt ctctatcccc tctcctgttc tctctctgtc tctctcaaat aagtaaataa 4440
agtctaataa acaaacaaaa atgcttctct ttgtgttttt tatattatgt gggaaattat 4500
aaacctttgt aaaaaaacaa attttttttca gagatgggtt acaaacagta gtcctttcca 4560
tagagtgatg gaaattttct caactcccca attgtattcc attttgctaa taagagtgac 4620
ttacgatttt caattaacca acccaggtat ttgtacagct tagtacatct gagcactctg 4680
tgaaagaggg aagctgatac tcattataag ccacttctca actaattggg gagtaaaact 4740
gacacctatg agataaggaa ttttaaatat gattaaagac caagtatatt tataaataag 4800
tcaaacaaaa ctcttaaaag taaaaatgca ataatttgac taaaatactc agtggagaag 4860
ttttataaca gagtagacac tgctgaaaaa aaaaaaaaat cagagatcca ggaactaaaa 4920
ccaaagaact ttatctggag ttcacatcag agagatatag atgtaatgaa tagagaaaaa 4980

```
caatgagaag acatgggaga tttagggata aggtcttact atatctagtt ggatttttcc   5040

aggcagagga gagaggaaag ggttaggaac atttgaagtg acaatggcta aaaacgtacc   5100

acgtgaagaa gaataacaac tcatagtttc aagaaatcca acttatcaat gcctaacttt   5160

acatttctgg tcaagaaaga tggatcttag aactctgatt cactttaatc cacctcccag   5220

ctcatttact aatgctttta gttattttaa gtccactttc ttttaaagct ctacaaagtt   5280

gagaggaaga gagtcctctc ctatttttct cactcattgg ttcatattgc aacctgcttt   5340

t                                                                   5341
```

<210> SEQ ID NO 2
<211> LENGTH: 33741
<212> TYPE: DNA
<213> ORGANISM: Canis familiaris

<400> SEQUENCE: 2

```
atgctcaacc actgagccac ccaggcgtcc ctatactgtt tgtttgtttg tttgttttta     60

atttttattt atttatgata gtcacagaga gagaaagaga ggcagagaca caggcagaga    120

gaagcaggct ccatgcaccg ggagcccgac gtgggaatcg atcctgggtc tccaggatcg    180

cgccctaggc caaaggcagg tgccaaaccg ctgcgccacc cagggatccc tgtttgtttg    240

tttttaataa ataggtgtaa aatgttttaa aatgagctgg agtggtgtgt ggtagatttt    300

gatgatttgt ttttttcata atgagggaaa actaaccaag tagaatacta gttatgtact    360

ctaatggacg acagtaccag gtaacaaaag ttgtggcttt tcttttacca ctttctctag    420

gttaagtttt aatgtcagta ataatgaata aacctaaaac tttatttgtc aacctctaaa    480

acttaagttt aaaaagcgta tgtagtaaga ttcccagttt tcataatatt tttacataat    540

aaatgctttt ttatgacatt ttatgatgta tataaatact ttttatgaca ttaagtgaaa    600

tgactttcca tcatacttaa aataaaacgt aaacattctt taccatggac tgtaaaattt    660

tgtgtactct tgatttctgt ctgccctcca gcttcatctc tttactctcc ccctcatgct    720

tctatcacac tggctttttg tcaggtcgta gattatacca agttctttcc tgttacagtg    780

cctctggctg gctttttttac atggtgagat cctcactcct caatcaagcc cagctaaaat    840

gtcccttccg actttccttg tgacctccct ctctagaata gatctttcat tcattatcac    900

caaatctatt ttctttttca cacatcacat tcaactggtt gacagatctt tagctctact    960

ttaaggggat tcctacccct tctctccatc tctttaggcc aggatctata acacaaacct   1020

tgctttgaca cttgcattca cagcagccag atttcatggg aactttagag actattaaag   1080

atctacctga agaaaaaaaa aaaaaaaaag atctacctgt actttggctc aaaggtctcc   1140

tggaaaaaaa tagacaataa agatatgaat aagtccagtc catgaacaaa taattatggt   1200

gttaggcatc accatgatga atgatcattt ctgaacttaa gaatacatct ccataaagta   1260

gatcactatt atttagtctt acaagtgtgg gtacataaga gcatgcatta cctggtagag   1320

ggacccagtt caactgaatt ttgaaaagaa ctctggtttc tttctgtgcc atgctacctt   1380

ccattgaaat ttgacttaaa ttttatgtgt tgggttaggt cttgattcat tcttatttta   1440

aggacaggat tatataaagt gagtgagatc atttgcatta gtctaatatt catttgttgt   1500

gctagatctc caacttgctg ctgaacttgg gaagacatta ctggatcgga acacagagtt   1560

agaagattct cttcagcaga tgtacacaac caatcaggag cagttacagg aaattgaggt   1620

aatttactga ttaagagagt tacactttaa gttgtggcat gttgctgcta ttgaccagtc   1680

atgttctgct aaaatagcac tttcaaagaa ccattggaga gacttgggaa gttgatttct   1740
```

```
atttttttgt gctttcccaa catatgtctg atgaaagaaa tttctctctt taccttggtg   1800

aagtatacta gaagcaaatg gtccagtgtt taccattatg tgaaacacaa taaaattgtg   1860

aatattatgc ttcgttttta acttttttta aatagatttt atttatttat ttgagagaga   1920

gtgtgagcca gagagagaga gaaagagaga gaaagtgagc acaagcaagt aagagcaggg   1980

gtgagagaga aggagaagca ggctctctgc tgagcaggaa gcccgactcg gggctcaatc   2040

ctaggaccct ggcgttgtga cccgctgaag gcagacactt aaccgactga accacccagg   2100

cacccctact tttttctttt aaaaaatgaa ttatgtaata tttcagatat tcccagaggt   2160

gtaagagaat acaacgaata gctctgtacc caccacccag cttaagaaaa aactacccat   2220

actgttgagg ctccctcttt ggttataccc ccttccccaa ccactgccaa ataccatcct   2280

aagtttgggt ttagatggaa aaaattttaa attgtagtac tgatttcatg atgtgtttaa   2340

atttcttgtg ccattcaaag aattaatcag gacaacccag gtggctcagc ggtttagctc   2400

tgccttcagc ccagggtgtg atcctggaga cccaggatca attccctctc gggctccctg   2460

catggagcct gcttctccct ctgcctgtgt ctctgcctct ctctctctct ctgtctctct   2520

catgaataaa taaataaaat cttaaaaaaa aaaaaaaaaa gaatcaggga tgcctggcag   2580

gccagtgggt agtgtatgca actcttgatc ttaagttcga gccctatgtt gtgggtagtg   2640

tatacttaaa aaaaatcata aaatggatat ttctttctct ttgcttgata ttaatttatt   2700

tacatttttg gtagattttt aaattttatt ttttttaaag attctatttt attcatgaga   2760

gagacagaga ggcagagaca aaggcagagg gagaagcagg ctccccatgg ggaggccaat   2820

atgggactcg atcctgggac ttctggatca caccgtgagc caaaggcaga cactcaatca   2880

ctgagccacc caggcaaccc tttagtagat attttttaaa ttaaaagagt acttttcccc   2940

taattataac aaactaaaat gagagttact agattaaggc tttaaatgca aggtgctggg   3000

gtacctgggt ggctcggttg ttgagcgttg gaacctcaat ttcagctcag gccatgatat   3060

aaggattgtg agattgagcc cctagtaggc tccttggtca acatggagcc tacttcagat   3120

tctctctttc cctcttcctc taccccctccc caccccccacc ttacatatgt acatgcacac   3180

ttgtgtgttc tcaatctctc tctttcaaat aaaaaaataa aatcttttta aatattcaaa   3240

atgaaaaata aaatgcaggg tgctatcttg taaatggtcc cattcaagta gtccagttat   3300

gggttggcca tgtgactata aagatgataa ttttgggggt gcctcactgg tgcaatcagt   3360

ggagcttcta atttttgact tagggattgt gggtttaagc cccttgttgg gaaaaaaaaa   3420

aaaaaaagcc ccttgttggg tgtacagatt acttaaaaat aaaatctgta agaaaatata   3480

aagatgataa ttttgaatat taacctgaca gttgtctcat tagaatactt ttctctatgt   3540

tccacctccc cacatacctc ccctacccaa aaaaaagctt tgcacttaaa tgacaactcc   3600

ttcctctcaa attggtacat tagagacagg attcttgtgt ttatgtgcac gaaaaatgta   3660

aaagaccttt gaacagtgat cagaacttac tgagtggggt acttgggtgg ctcagttgtg   3720

actcttgata ttggctcaag ttatgatctc agggttgtga gatcaagccg tgcattgggc   3780

tccacagtgg gcattgcgtg tacctaagag tctctctctt ccttgccctg tgcccctccc   3840

tggacccccc cccccaaaga aaatactaaa aaaggcaaat tcataatcta aatatcctta   3900

attttacata gtagccataa ttaacgtgtg tatacagcag atctttcctt cattaggatt   3960

tatgaataat caggtgacta gctctgtgag aaatatgctt ttataatcta gaagggtata   4020

tcttgtaatg atattgaagt tattagctac cacttttagc atgttctata tcaaaagagc   4080
```

```
atagaacatg ccatacccag actaaatata gtttccaaga aacctaaaaa tgcagaaaaa   4140
caagcatttt aaaagctgtt actaggagag cctggacgac tcagtccatt gggcatctgc   4200
ctttggctca ggtcatgatc ccagaatgct gggattgagc cctatgtcag gccccttgct   4260
cagtggggag ccaccttgtc tctctccctc tgcctgctgc tccccctgct tactctctct   4320
gtcaaataaa tatgtacaat cttaaaaaaa aaaaacaaaa aagcaaaact gttaaaacta   4380
gccaagtgtc atacacaaag aattcatact tgctttgtgt cttagacttt gctttacaac   4440
tcagaagatt tcatagagca gtcctagggc catatcatat gctgtgagac acatctattt   4500
ctacttgggt agaaacgtag tctacttagg tagaaacatt taagagaatg atacctattt   4560
gttaccacag gagactatga acacaattgc tttatgatct aagtgactta ttttcttctt   4620
tcttctgccc tgtggtattg aggatgatta aacagttaag acagattgtt ggcattgtga   4680
aaaaaaatcc acagattttt gaaattctct caatcttcaa ataacactat accatctatt   4740
gtcttttata aggtgttgca aagtgtaatg gaaatgaagt gtccaattca gatcttaatg   4800
attaaataaa tataaattta aatacgtgta taacctattc aaataaattt agcctagaat   4860
attccggaaa cattttcatg actcttcttt ccataataaa gcatgtagtt ccctggttca   4920
tagatccaag cattgttgca ttcaacattt tactctttat ccaaagctgt gttttggctg   4980
agaacaacac tttcatagat tttttttctc taccattgca gttggctatc ttctttcttt   5040
ttataaatca ctttatgaaa gtcaatgggg agggacaaaa tgaggagatg aaagaaatgg   5100
cagtgctggt taagctcact tagtagccag agcaccctcc ccccaaagtg gccttattgc   5160
ctgatcaggt cacatctatt tctgtgcaga cttacaagtc acaatattaa ctcccaatag   5220
tctaaaacaa ggaaagcttg atgcttttat aaaaggaagc aggcagccaa agagcctaat   5280
tccgtactaa aaggtgaccg ctttttatat gcttatcatt gcaaccttca ggaaccacct   5340
aagctttatg aaggcccttt ccttaattca aaccttatat tagttctctc tgtcttttaa   5400
aaagtaaact ttttattgaa atacacatac agaggaatgc ctgggtggct cagcagttga   5460
acctctgcct ttggcttagg tcgtggtccc atagtcctgg gatcgggtcc tgcgtcgggc   5520
tccctgcatg gagcctgctt ctccctctgt ctctgcatct ctctctgtgt ctctcatgaa   5580
tgaataaata aaatgttaaa gaaatatata tatatacaga aaaaagcaca aatcctaaat   5640
atatagttca atgagtgttc attaacatac tgatgaaacc aacacctagg taagaaataa   5700
gaacagtatc agctctgcta gtcgtcaccc acactaacca gtatgctaat acctagatta   5760
atttagcctg tttgaacttt accactttta caggttttaa actaactttt tagaatgttt   5820
attgggactt ttcctgacta gaaaagtaat atatgatcat ttttaaagat agaaaaacat   5880
gtagttgaaa accagaaagt tagccttacc acctggaaaa atttgaaatg agatcatcca   5940
gaagaatggt actgaaactt ggaaaatact agtataaaat ctcccaaact gtgacacatt   6000
atagacatta tagaaaaaga caaataagga aactctcaag ggtgttttat aagaactaca   6060
agtgtgcttt caaagactca cagtggattt caaataatcc tcgtaaaaat tgatcagtat   6120
tttttagtga tcgttttagg tttctttttg ttaaagaaaa gagtccaagc atgagtaggt   6180
caaggggcag agagagagaa ccagactccc ctatgagcag agagccctac acagggttcc   6240
acctcaggac cctgagatca tgacctgagt aagccaaagg cagacgctta acagactgag   6300
ccacccaggt gtccctcagt gattgttttt tatgtaaaaa aaaattaaac tattgaaagt   6360
aaagattggc ttcagagata cctatagtct gtgtgacttt tattcagtgt tgatttgaac   6420
atataatttt tcaagactgc cgagcaagtt tttctctcct ggatgagggg ggaggagaga   6480
```

```
agccttggag ggtaatgaga tctggcacca tcagacataa tcggattctc ttaaagattc   6540

ctataatcat gtaagcaagt ctacagcctt atgtttgtgt tgcatctccg cttggaaacc   6600

tgtattattc ccataagcct tgtcactacc actcaaagta gtctggcctt caagatatcc   6660

tttcaagaac ttatgtcttc cttggaaatt ttaaggcatt ttattcctct gctacattta   6720

tcaatattct gtatatttat gatttgttct agtctaccca cccatttccc agtgcaacat   6780

tgaaggctgt tgctatgttt attcatggtc tttcacagag taaacatcaa taaatacttg   6840

ttgaaaccta tatccttttt tttttttttt tttttaagta ggctctgtgc ccaacatggg   6900

gcttgaactc atgaccctga gattgagagt cacatgctct accaactgag ccagccaggc   6960

acccccttaaa tcagtatttt agaaagggac agattagcaa tttgcaaagc acttctgatt   7020

cctaaactgt gggtttccac cttgagattt tttttaaggc aataggaggg gcactggctt   7080

tagcattaga agattcaggt ttaagccctc cagcctatag caaatagatg gagactttag   7140

gcatgtgaat tacctctcag atcctgtttt ttctgctgta taatggtgat aagaatgctt   7200

gcactacatt ggcacagggt tgtcctgaag ggatgaggtt atgtaagtgt attttggaca   7260

gtataaattg tacaatttat ccatgttata agaattttgg taatgaatct taattcagaa   7320

aaaaatcctt ttcaattact ggaaaattga ttttaaaaac aagccaggct tttaatagat   7380

tatattatag gtggttttta tttttatatt catgcctctt ctctccaccc cccccccct    7440

ttaaatttcc tacaggggaa ataaagtatt ttaatcaggg aaaaggtttt tcaaaggtaa   7500

aaggaaatat ttcttcagaa ttgtagaagt cattttgata ctaaactcag aggatttggg   7560

caataatcct taatagaagg ataatcccaa cactgcataa aagccaaatt tccattgcat   7620

tccttatgtg ttttaagttg gggtttttttg tcttttctcc tttactccag gtcacggttc   7680

tgcaattgca aatagatagt aatcttgctg gcctttcttt ttgaaagatt tgcctcagtt   7740

gttaagttga actatttata gcttttgctt ataacctgaa ccttgtactc ctagtcaagg   7800

tggcattcta cgcaaattcc aagaaacgtg tgtaataact cagagaacta aactttgata   7860

ctcttggcta taaaatcgac atttttgcct gtgtttttgc tactgtcgtg tttgcctccc   7920

catgttttgc ttaaatgtct ccctttccgt tgatatgttt aatatgacag atgcttttgt   7980

acttgagttt tggcacttga attttggatc ttggcagtcc tgtcgaattc atttgaggtt   8040

gtgtgtcaaa gattctgaat agagaaaacc agaacattag aagcttatct ttgcctttaa   8100

atgaagggta gaaaatgagc taactcagtc ccttctagat tcagaaaaaa attgacaaat   8160

actaatttga aactttggag gtcaagtgtt aaagcaaggt ctgaccacat acagttctga   8220

ttctctggtc tgataccact acttgctggg agatctaata atttttcttt taagttgctg   8280

accaagttag tcagacttct ttgttaggta acctattaca gattcttgta gaagtaaagg   8340

gctttttttga ttacttttga tttaataata ataagattaa actcctacca cgtgaaaaca   8400

agctccctgc cattctttag attgccatta aagccaagtc ctctaagacc aaaatattac   8460

aagctcttca taaatggttt cattgtgttt ttatcacaag tttatatatc aaactagaag   8520

gacttactat agtttttctt gatacatagg tcctctccac cctcccagtc tgtggttgca   8580

ctttttgcag tttcagttac gtggtcagcc cccatccaga aacagacaat tctccttccg   8640

ttgtatggtc agaaggtgcc ttggagcttc acactgtgtc acaatgcctg cgtcactcac   8700

ctggcttatc tcatcacgtg ggtgttttat cagctcatgt catcagaaga agtgtaggta   8760

cagcaaagga gatattttga gagagaccac attcacataa cttttttttta cagcctattg   8820
```

-continued

```
ctataattct attttattat tctcactgtg ccagatttat aaattagact ttatcatagg   8880
tgtatgtata gggaaaaaac atagtcatat atttagggta cggtgctatc cactttttca   8940
ggcacctact gggagtcttg gaatgtatcc ccagtggaaa agagggggac tgctatcgcc   9000
tctttgtact ttatttacat atttgtttcc tttatatttg aactttatat ctttaaaagg   9060
ggacaacaat taggggccca cataatagct ggtaggaatt ataaatgttt ttcagattac   9120
tgggaataag taatgttttt cagattgtgc catgggaata agtacagaga agtctataaa   9180
tgaggcaaaa gggagggaat tagtggctat taggaacttt tcccaagagg gctataacca   9240
aagcccttct cagaatcttt tagttaagtc tcctccacat ttcagcagtc ttagttgtgg   9300
taaagagcac gataagctgt tgtgaataga ggtctagaaa ttgccatttt ggggcgccta   9360
gctggctcag ttggtagagc atgtgactct tgttctcagg gtcatgatag aaaggaattg   9420
ccatttagcc aatatttttt gagtccctac tatgtatcag gaattgtact aaatggacta   9480
gaaagagaag aggcttccct tttcaaggag ggtcagaaag actggacact gggatgccag   9540
ggtggctcag cagttgagcg cctgcctttg gcccaaggcg tgattctgga gtcctgggat   9600
cgagtcccac attgggctgc ccccatggag cctgcttctc tctctgccta tatctctgcc   9660
tctctctctg tcatgaataa ataaaaatct taaaaaaaaa aaaaaaaaaa agactggaca   9720
ctaacaagta agcacttggt catttgttat tacgctaatt gttttaaagg aaactgataa   9780
gataccttgg gaaaggtgct gcttgaggca gggtggtctg gaaaggcttc tgaaaagatt   9840
atgtttgagc agaggcctta ggacaatcag agttcttaac cattcttgtg ccatagatcc   9900
ctgtggctgt ctggtgaggt ctgtgatgat cctcttaaaa tatatagaat aaaagggaat   9960
ctgttatatt gaaatgcctt atcaaaatat taaaaaaata aatatgtgat atggtaatgt  10020
ttgtcaacct aaaaagtata atttcaaata gtgatgagtg tagccaataa atcaagattt  10080
ctgcaatcac tatcatgtga tatgaaaata tctgtgattt ctattggtga tgaagtccta  10140
gcaaccccat catactactt atggcttgat ggcttgttgc ctccattcag aatcaaagca  10200
cgtggtaaat attggaagtt agagaaaata aagatataac ttctccctca ttcaagttca  10260
cagatcctgt cagttctgtc tgtggacccc agattaagaa ctgctgggtt aaatggagcc  10320
agttaggaaa aacacatccc ctaacagaag gggagcttg cttagagtaa ggcaactcca  10380
tagttttaag gtaaagatac tttgtgaaat aaggatgaat cagtagctcc ctggtgaaac  10440
tggaagagcc acttaagaga cagttgggaa aatcttaatt aagactgaaa aataggggat  10500
ccctgggtgg cgccgtggtt tggtgcctgc ctttggccca gggcacgatc ctggagaccc  10560
gggatcaaat cccacgtcgg gctcccggtg catggagcct gcttctccct ctgcctgtgt  10620
ctctgcctct ctctctctgt gtgactatca taaataaata aagaaaaaaa atatttaaaa  10680
aaaagactga aaaataaatg atagtaaggg gattattggg aggttttagg tatgattaaa  10740
attgtagtta aaacaaaaag tcttttagaa atatatgaat atggatattt aagatgtctt  10800
ggatttgctt taaaatgatt ggagatgaga ataggaaagt agaaatgtca caagactgat  10860
gataattgtt gaaactggat gatggataga tgggggctta ttaaaccatt tttttctctt  10920
ttatatgttt gacattatcc ataatgtttt aaaaacatag tagagggcac cccaggtggc  10980
tcagctgttt agcgctgcct tcgggccagg gcctgatcct ggggaccagg gatcgagtcc  11040
cacgttgggc tccctatgtg gagcctgctt ctccctctgc ctatgtctct gtctctctgt  11100
ctgtctctct gtctctcctg aataaataaa taaaatctta aaaaaaaaaa tgaaatctct  11160
aaaaacatag tagaggggca gccctggtgg cttggcggtt tagcgccgcc ttcagcccag  11220
```

```
ggcccaatcc tggagacctg ggattgagtc ccacgtcagg ctccctgcat ggagcctact  11280
tctccctctg cctgtgtctg cctctctgtc tctgtctctc tctctgcatc tctcatgaag  11340
aaataaaatc ttaaataaaa aaacacacac agtagataaa attagccatg tataaagagt  11400
ctgtacttgg gtggatgaaa gaagcagcac acaaggtcag gaccactaat gtattatttc  11460
gggggatgtg actaaaagaa catattgaag cataactggt aaagaacgct gctggggtgg  11520
ttagaattcc acttcatctt aatgaagagc tgcaagtact agtcctatgg agggaaatgg  11580
taaacatgaa gcttaagaat cattgttgat ccaagtgaat gctgatgcct cctggaccta  11640
agagaaaaag acattagttt ggggggaggg gagacttcca gggttttcca tgtccaagat  11700
caacatttct ctaataagtg tgatccatgg acctcttata ctaacctcac ctggagtttt  11760
tgctgaaaat gcagaatact gattgtaccc tagtctcacc gactcaaaat tttaggagaa  11820
aggggtatag gttcctgtag tttgtttaat aaagctctca gatagatgaa tcttagcaca  11880
tgcaaagttt gcaaactaac tgtagctgcc tcttcctgag cagttttacc atatgctgac  11940
gctgtgctga acccttcaca cacttaaacc ttacggcagc ctttgtgaga taggtgatga  12000
ggaaatatcg cctgagaatt aaggttactt gccaaaggtc acccggttag aggtggtgaa  12060
gcagaacttc agattctaac ctatgctctt agatactgct gcctcccacc aggctctttt  12120
ctctgattct atacccacca aaagatttct gtggaaattg acctctcacc tgccctttac  12180
agaggatgtg ggtcttccag taactgggca gagacaattc ctgtggtaaa ttagtaatta  12240
gtgtctggtc tatgtgttag ccttttttcag tcgttgtaaa tcagtgccaa agaatacttg  12300
acacctatac ttgatataaa agtagcttgt gaagtttctg taccctttgt atgtatacct  12360
gtatcctaaa ctttgtccct aagagattga acacattccc atcagtcata ggaacctact  12420
atgacatcgc tagccagagg gcaggattag gggccttctc ccaggagaag ctggtaggta  12480
ctgaggcagt gaaggctaaa cataggcttt gagagggacc gtgatcagtg tgtgctcacc  12540
taccttattt aatatattta aatcctacaa gataggttag tcatcaattc ataacccctt  12600
atttttcaat tctgaaccca aaggctctat aaaacaagat tttttttcc tttaagtttg  12660
cagcagattc atttggcaga aaccctgac ctgaactgtt gtgaagctgt ttataatcct  12720
tattcacact taccattgca gaaatattaa tgctcgggac acctgagcgg ctcagcagtt  12780
gagcgtctgc cttcggccta gggcgtgatc ctggcgtctc agaattgagt cctgcatcgg  12840
gctccctgca tggagcctgc ttctctctct gcctatgtct ctctgcctct ctctctgtgt  12900
ctcatgaata aataaaatct taaaaaaaaa aaaaaaaaaa gaaatgatcg attacaggat  12960
gctgctcata ccacactgag gatgtttaaa gtttttagtg tgtttgccac gttgtctttc  13020
tacaattgaa agaattttca aaaacatttt tggcccctag agtttcagat gagaaagttg  13080
aagttatgag acttaagtgt tttctcaaca tattaccaag ttatatcact agattttgaa  13140
aaagatcatt tattcttttt ttttcaactg tcacattgtc atttatagtc cactgaaaat  13200
catttagcac attctttgaa agaagtcttt tagctttgca aatatagttg tacagattta  13260
cagttgtaaa ggtgactttt gactcttgac aacatggatt tgaactgtct gggtccactt  13320
acacaaggat tttttttctg aaaatacaga acgtagtgta aatatatttt ctcttcctca  13380
tgattttctt aacattttct tttctttagc ttactatatt gtgagaataa gtatgtaatt  13440
cgtataaaca tacaaaatgt gttaatcaac tgttcatgtc attagtaagg cttccagtca  13500
atagtaggct attaaagtct tagaggaata aaaagttaca agtggatttt tgactatgcg  13560
```

-continued

```
gaagtttgtg ccccaacccc atgttgatca aggatcaact gtatagttgt acaaaaagcc  13620
ccaagaagtg ttgtggggtt tttgttttgt tttgtttttt aagattttat ttatgagaga  13680
gagagagaca gaggcagaca aaggcagagg gagaagcagg ctccatgcag ggagcctgac  13740
atgggacttg atccgggtct ccaggatcag gccttgggcc gaaggtggcg ctaaaccgct  13800
gagccacctg ggctgcccgg ttttgttttt tctttttaag atttatttat ttatttgagg  13860
gagagcaagc aagcaagagg agcagaggag agagaatacc aagccgactc caccctcagt  13920
gtggagccca gtgcagagcc tgatctcatg tgcctgagat cacaacctca gctgaaacca  13980
agagaccgat gcttaactga ctgggccacc aggcacccaa gacatgactt taaaaacatt  14040
ttccttgggg cgcctaggtg acttagttaa gcatctgcct ttggctcagg gtcatgatcc  14100
tgggctcctg gaatcaagcc ctgaattggg cactctgctc gggggggggg ggggggctgc  14160
ttctccctct cctgtttcag cttggccaac ttacgcttgt tttttctgtg tcaaataagt  14220
aaaaattaaa aaaaataaaa gagccactaa aaaaataagt aaataaaaat actattcttg  14280
gggctcctgg gtggctcagt cagttaagca tctgactctt gattttggtt caggttgtga  14340
tcccagggtc atgagattag gccccacatc aggtttcata ttcagcagag tctgcttaag  14400
accttctctc tctctctgct cctactatgt gtacatgtgt gttctctctc tcagaaaaat  14460
ctttaaaaag tcatgtcttg ggcacctgga tggcttagtc aagtgtccaa ctcttgattg  14520
cagctcagat cttaatctca gggttgtgag ttcagagccc acattgggct ctgtgctata  14580
ggctaggtag gcatgtagaa tttaaaatca tgtctttggt cttttaccat ttgatcattg  14640
atgatgcttt gaacctacct ttttttcctc tttctagttg tgctccagag aaatgttagg  14700
aatatttcat ttggaatata tactgtgttt cattgtcttc tggtggagtt gctgtaggag  14760
aggcagtcag tgtaatttaa cactgaggca tgaagactgt gattattccc ctttatcctt  14820
ggacatttag aaagtgattt tagcatttac cagagtaaat aatctggcaa atttctcatg  14880
aataaagagg attatggtgg ggcacctagg tggctcagtg gttgagcatc tgcctttggc  14940
tcaggttgtg atcccagggt tctgggatcg agttccgcat caggctatct gcagggagct  15000
tgcttctctc tgtctctgcc tctctctgtc tctcaggaat aaaaaaaatc tttaaaaagg  15060
attatgatga tcacattctc acaatattaa aaataacaag agtctttgaa ttatagtaag  15120
ctaaatatct ctttctggat aagtcagtta tttcccctgt atttttgtcc agagtagctc  15180
atttggagaa aaaaattcca tttttcttcc aagcaaaaaa tcatctaaaa ttctctactt  15240
caggctttct tatttctgta aaacatggta tttttgctta aacattgatc atgtattcca  15300
ttgcttttac tcttgtggga ttgtcagtct cagatattct tgttgaatat taattttatg  15360
catgcattgt gctttagaag agtagaccag cctcatgata cataggatgt tggtaagcat  15420
taaggaaagt aaacatataa aggatggcct gtatttattt cctattagac aagtacttta  15480
attgggattt aaagatttta tttattcatg aaagacagag aggcagagac atagagggag  15540
aagcaggctc ctcacaggga gtctgacgta ggacgtgatc cctggaccct gtatcacgcc  15600
ctgaagtcaa ccgctgagcc acttaggtgt cccttaaagt ttttctttac ataaaataga  15660
cctgtggtat tatggtataa taaaaaccat gtatttgatc tttctatttc gtggcacaga  15720
gcttctaaaa ccattggaat ttcctgagga tagaatggga actggttgcc agaagaagca  15780
caaccataat attagttaga accatcagtc caacccccaa cctctgggga gggaatgggg  15840
gttggagatg gagttcagtc accaatggcc aatgatttca tcagtcgtgc tatagaatga  15900
agcttcaatg aaaccctgaa acaaggaaca cattgaggtg ctaataggct agtgcatctt  15960
```

aagagggtgt agaagctcta cactcctctt cacccccata ctttgctctg tgcatgtctt 16020
ccatgtggct cttcctgagt tgtctttttt tttttttttt tttttttttg agttgttatc 16080
ctttttataa agtagtcagt atagggcagc tcaggtggct cagtggttta gcgccacctt 16140
cggcccaggg tgtgatcctg aagacctggg atcaagtcct gcatcgggct ccctgcgtgg 16200
ggcctgcttc tccctctgcc tgtgcctctg cctctctgtg tgtgtttctc atgaataaat 16260
aaataaaatc ttaaaaaaaa aaagtcagta taagtaaagt gatctcctga ggtctgtgag 16320
ttattggagt gaattattaa acctgagggg aggttgtgga aaccttcaga tttacagctg 16380
gttggtcaga agtacaggtg gtctctggat ctttcaactg gtgtctgaag tgcagcaatt 16440
ttataggacc aagcccttct gacctggaat ccctacaggt aggcagtgtc agaattgaat 16500
tgtaagatac ccagttggtg ttggagaatc aagagtgggt gttcgaatgc tgcgggtatt 16560
ttgtctgttt aatgtataac ctggtcacaa tcattttctc ttacagtatc tgaccaagca 16620
ggtggagctt ctacggcaga tgaatgaaca gcatgcaaag gtttatgagc aattagatgt 16680
cacagcaagg gaactggaag aaacaaatca aaagctagtt gctgacagca aggcctcaca 16740
gcaaaagatt gtgaggtaaa ttttctagac tccattgagg aagccctaga gggagttact 16800
tagtgttgac tagaatagaa tgtggcttta gtggatttgg gtcaatatgg ggtacagttt 16860
aatttaattc tttatggaga atagagatta aattagaagt cctttccaat taagagtgcc 16920
cagtttgagt ggctggcaac taatctctcc tcactgctga tgcccttaat ttaatatgac 16980
aagcagcaaa cggcttgctt ctgttcctca cagtctgact gaaacaatcg aatgtctaca 17040
aaccaacatt gatcacctcc agagccaggt ggaggagttg aagtcatctg gccaaagaag 17100
gaggagccag ggaaaatgtg accaggagaa accggcaccc agcttctcat gtctgaagga 17160
actgtacgat ctccgccagt aagaacctgc tgttctgtgg tattaatgag cggggaagcg 17220
tcgcctgtca gcgacacatc cctgattcaa gtagattaaa agtacccttt tatgaattgc 17280
tacttggtga ttagactacc agtggtttga gcaaaaccac ttaacttaaa tatacaactg 17340
atcaagttct tgggcattag taattctgca aaaacttatt tttagaaatc ttgagaatat 17400
tcatttcagt gctttgcatg tgttaagtct tcgtttaaat taagttgtac ttctgataga 17460
ctacaggttt gggggttgta tttcgcatta gagtggaaaa aatcgaaatt tcaaaaaaag 17520 ctttttttgcc tcagaaatgc ctttataggg attcctgagt ggctcagtgg ttgagcatct 17580
gcctttggct cagggtgtaa tcccagggtc taggatcgag tcccacatca gactccttgc 17640
aggaagcctg cttctccctc tgcctgtttc tgcctctctc tctctgtgtc tcatgaataa 17700
ataaataaaa tctgggatcc ctgggtggcg cagcggtttg gcgcctgcct ttggcccagg 17760
gcgcgatcct ggagacccgg gatcgaatcc cacatcgggc ttccggtgca tggagcctgc 17820
ttctccctct gcctgtgtct ctgcctctct ctctctcact gtgtgcctat cataaataaa 17880
taaattaaaa aaaaaaaaaa taaataaata aataaataaa taaataaaat cttttaagaa 17940
aaagaaatgc ctttataatt tagagttaag agactgaata tttaagaact acttcttgag 18000
gggatccctg ggtggcacag cggtttggcg cctgcctttg gcccagggca cgatcctggg 18060
gacctgggat cgagtcccat gtcgggctca cggtgcatgg agcctgcttc tccctctgcc 18120
tatgtctctg cctctctctc tctctctctc tctctgtgac tattataaat aaataaatta 18180
aaaattaaaa aaaaaaaaaa gaacttcttg agcacatatg tggcaggtgc tatgccagac 18240
atgaggagtg gtgagcaaaa tagacccagt tcctgccctc ccacttcagt ctcggggaga 18300

```
ggcagataca aatcatcaca caaacacagt tacaagttac ctaggacttt gcacaggaga  18360
cctaggcttc tgcatttgga ggctctcaac cttgactctt gatcaagtca ctttggaatt  18420
tttcaaacag caataccagt gagtccctca ggcctaaatc gggatctctg ggtactggga  18480
aaaacctgcc caggtgattc tgatatgcag ccaggcttga gaacccctgg gccattctca  18540
tttccttcac aggagtcagt catatcactg gacttagaaa atgggtgtcc tgttaatggt  18600
taaaaaaata gtcacaaaaa ttatgttttc ttacatgtgc ttatttgcta gccttacaga  18660
atttcatttt aaccattgct ctagtgtaga ataggcaaaa aattaatcac tgtcacattc  18720
ctcaaaaata ttaaattgaa aggggatccc tgggtggcgc agcggtttgg cgcctgcctt  18780
tggcccaggc gcgatcctgg agacccggga tcgaatccca cgtcgggctc ccggtgcatg  18840
gagcctgctt ctctttctgc ctctctctct ctctctctct ctgtgagact atcataaatt  18900
taaaaaaata tatattaatt tgaaaaaaaa tcttttcatt cccaattgac ctatgtaacg  18960
tgtgtgtgtg tgtgtatttt tttctttttg gtaatatgtt ctttcaacat ttttgtccta  19020
gacactttgt gtatgatcat gtgtttgctg agaagatcac ttccttgcaa agtcagcaaa  19080
gccctgatga agaagaaaat gagcatttga agaaaacagt gacgatgtta caggcccagc  19140
taagcctgga gcggcaaaag cgggtgacca tggaggagga atatgggctt gtgctcaagg  19200
agaacagtga gctggaacag cagctgggag ccactgacgc ctaccgagcg cgggcgctgg  19260
aattggaggc tgaggtggca gagatgcggc agatgctgca gtcagagcat ccttttgtga  19320
atggggttga gaagctggtg ccagactctc tattcatacc tttcaaagaa cacagccaga  19380
gcctgctgga ggagatgttc ctgcctgtgt cggaagcaca cagaaagcct ctcaagcgca  19440
gcagcagtga gacagtgcta agcagcttgg caggggggga catcgtgagg ggtcatgagg  19500
agacctgcat tcggagggcc aaggctgtga agcagagagg catctccctt ctgcacgaag  19560
tggacactca gtatagcgcc ctgaaggtaa agtatgagga gctgctgagg aagtgccagc  19620
aggaagagga ctccctgtcc cataaggccg tgcagacctc cagggcactg gccaaagaga  19680
cccagcctga gctcgacacc agcagttggg agccagcttc tgctacccca gagcctgtca  19740
gttcccccac caccaccaca cctccagaat ataaagcgct ttttaaggag atctttagtt  19800
gcatcaagaa aactaagcaa gaaatagatg aacagagaac aaaataccga tctctttcct  19860
ctcattccta attcaacctc cagctctact actaatttgc ctatttcttt tcacctctct  19920
ctccaactcc gacaagtgtt tgtaaacccc gcagcctaat attactcatg atgtttgcct  19980
cgtagctttg cttatttagc agctgcgaac agcagcaggg aaagaaggtg gctgctggtg  20040
tctgttctat aatccagatc tgtttaaact cctcaggaaa tcccatgaca actggcctct  20100
ggctggcgcg ctgattaggt tgtgattcct tgaaaagccc cagaaccagt ggagggatag  20160
atccatgctc ctagggaagt aggcctggag ttactatagt gtatagtata tagaggttgt  20220
atagtgtaga ggagcaaaag ggcagagttg aaacaaaatt aaggcaactt ttgctcctcc  20280
ttctcaaaac catagaagtc agatggctgc caaactgaag tagctttcac aaacactgtt  20340
ggatactgtg aattcattaa gaaagaatgt ccaggagaaa gcaggggtct aatccagaat  20400
aaatggcatt gacaaatact ccaggccttg tgttttgttc catccactag tagttgagct  20460
gtgactgaca agtcataatg tgtctaagtc caaccaatgc cgaactgaaa aggcaagctc  20520
cggtttgacc acagttagct tgttagcaga ggccctagag ggccttcccc accccaaacc  20580
ccccacctcc agatggtttt cctcaaagct gtagtggtta gcagaggcag atgtgtaaat  20640
ctttcatccc taaagtcaaa ataaagcagc aagatctaag ccctcactcc taccgtgttg  20700
```

```
tccgagctgg ctcagctgac agccacaagc tacccttgtt cagttcctgt cgttcctgga  20760
aatgtttgtg acttgtgcag aattcgtgtc tgctacctta attactaaac agtattattc  20820
tgtgggaatc tactcatcct ctcacttgca tacttttaat ttaaaactat ttaagagaat  20880
tgaaattcca gttattgtat atatttttct aaaaaccaaa taaaactacc tatgaaaatg  20940
aacaaatgga tcacttattt taagctgaag ccatcttact gttataacca acttcacatt  21000
tttttattc caacagataa ctcagatttg accatgattt tttggagtta tttttcccc  21060
cattcttagg gatcatgtta atgtgttcag tagaataact atatgattga aaaatatgtt  21120
cttaaagatt ttgtttattt gagagaagga gagagcatga gtggtaggga gagggagggg  21180
aagaacaggg agaggaagaa gcagactccc cacagagcag ggagcccaac acagggctca  21240
gccccagtac catgacctga gcagtaggca tatgctcaac tgagccatac aggtgcccct  21300
atatcacccc atatttttaa acaagagtat actttaagcc tttttcacta tatctttcat  21360
tttcactgaa ccatgatctt tgaaacattt atctgaccat ctacattttt ctttttttta  21420
agatttattt gagaacagga ggaaccagga gggccagagg gagagggaaa agtagactcc  21480
tgctgagcag ggagcccaac atggggctgg attctgggcc tccaggatca tgacctgagc  21540
tgaatgcaga tgcttaaccc actgagctac ctaggtgccc cagaccatct gcattctttt  21600
tttttttttt tttaagattt tatttattca tgagagatgc agagagagaa gcaagctcca  21660
tgcagggagc ccaatgcagg actcaatccc tggtctccag gatcacaacc tgggccgaag  21720
gcggcgctaa accactgagc cacccgggct gccctgcatt ctttatgaca gtactaaagt  21780
attacaccta tggatataaa ctccatatgt atatttgcca atgagtgcag ttgaggaaag  21840
aaggtggctg ctgctgtcag ttctataatc cagttccatt taagctccaa aggaaatccc  21900
acgacaaact ggcctctgtc tggtgtgctg atgtgtgtat gtatgtaaat acatatattg  21960
tatatatagc catatataag aatccattta agtagtccct gtatctttgg acagttatga  22020
atctagaaaa taaatcatta gaagtgaagt aaaaaagagc attttgccat catagtcttt  22080
cagaagtttt ctgattcccc cagcttccag gccttgccaa tacaggagga tgcctagttg  22140
ctcacacctg tgccagtaaa ctttttgacc cttgccaaac ttatggaaga aaagtggagt  22200
ttacttgtag tttagaattc gtttactaaa gttgaatatt ttatagcccg ttaaaccatt  22260
cgtattgtat tttgcctatt tttcttattt aagagctcaa gcattgagga aattcatttt  22320
gtaactagaa gttacaaata ctctatctta attttacctt gttactggca ttttgtgaag  22380
caaaattttt tgtggttata ttagtttttc aatacttttt tgtgctggac aggtgtttga  22440
tccacctaaa gttcattttt tttcttttat tgtaaaaata cacatgacaa ttatcatctt  22500
aaccattttt taagtataaa gtgttattaa gtaaattcac attcttgtgc aactatctca  22560
gtcattcatc cccatgactc tcttcatttg taaccatgaa acttggcccc tttaacttct  22620
cattctccct tccccccagt ttgcggcaac tacctttaaa cttttctgtc tttatgattt  22680
tgactaagta cctcacagaa gtagaatctg tctttttgtg attggcttat ttcactgagc  22740
ataattacct caaatttcat ccatgtcgta gcatattggg tttccttttt aaggctgaat  22800
attattctat gtgtatatgc cactttttgt ttatccaccc atcagtggac atttgggttg  22860
tttacatgtt ttacctattg tgactaacac tgctatgaat gtgtgtacaa atatgccttt  22920
gagatcctgc tttcagttct ttgaatatat actcagaaga ggaattacta gatcaaatgg  22980
taattctgtt tttatgtttt gaggaaactt catcatacgg ttttccacag tggctgtacc  23040
```

```
gttttacatg cctaccacag tacacattgg ttctagtttc tccacatcct tgccaaaatg  23100
tactttgtga ttttttgata gtagccactc taaaggaagt ggtatcttaa cagttttgat  23160
ttgcacttct ctgatcagtg acacaacttt caatgtgctt ggccatttgt atatctttct  23220
tggataaatg ttcaaatcct ttgccaatgt ttgaatttgt tttttctctt gagttacatg  23280
tatattcatt ctgggtatta atccgttatc agataattta caaaaatttt acatttaaat  23340
gttctagggg tttgcctttt taccttttt ttttttttt tttttgatga tttttatgta  23400
tttgacacag agggagaggg agggaaagag caagcacagg cagggggagt tggcagaggg  23460
agagaagttt ccccactgat cagggagccc aatgcaggac tcgatcccaa gaccctggga  23520
ccatgacctg aactgaaggc agatgcctaa ctgactgaac cacccaggtg cctcgccttt  23580
ttactctgtt gagattgtct tttgatatat aaggctttta aattgtcatg aagtccagtt  23640
aatctgtttt ttcttttgtt acctgtgcct ttggtgtcat gccaagagat cattgctgaa  23700
cccagtatta taaaacaaaa tagtgttgct gaagggtcca acttcattct ttagcatgta  23760
cataccgttt tcctagcacc atttgctgaa taggttgttc tttctccatt aatggtcttg  23820
gaacccttat caaaaatcat ttgaccatat atgtgaggtt tgtttctggg ttctctgtat  23880
tcctttggtc tgtgtgtctc ttgttatgcc agtaccacac tgttttgatt acagtagctt  23940
tgtagtaagt attgaaatca ggaagtatga ttcctccagt tatggttttt ttttctccaa  24000
gattgttttg gctatttggt gtcccttgag tttccatatg aattttggga taattttatc  24060
atgtctgcta aaactgtcat tgggatttag agatcgcatc aaatttgtag atcactgtgt  24120
aatattgaca ttttaacaat attaaccctt ctaatccatg aacatgaaat gtatttccac  24180
tttgtcttaa tttctttaag caatgtttta ttttcattgt atgaatcttt cacctctttg  24240
gttgaattaa ttacaaggta tttcaaggtg cctggctggc tcagtcagag gagcatgact  24300
tgatctcaga gttgtgagtt caagccctac gttgggtgta gagcctaatt aataaactaa  24360
aaataaataa ataaatattt cattcttttg gtgccatttt aaaaggaatt ggcttttaat  24420
ttcctttttg ggctgttcat tgttagtagt gtatagaaat gcaactaatt gtggagtgtt  24480
gactttgtat tcaactactc cgctgaattc atttattctg acaggttttt tggtggaatc  24540
tatagaattt tatacatata tcatctgcaa ataaaatttt tataagattt attttggaga  24600
gacagaacaa gagaagaaaa ggatggggta aggagagaga gagagagaga gagagagaga  24660
aggaagcaga ctccctactg agcacgcagg gagcctgatg cacctcaatc tcatgaccct  24720
gagatgatct gcgcagaaat ctagagtcat cttaacagac tgagccacct aggtgcctct  24780
gcaagtagaa aattttactt cttccttcct aatctgagta actttttatt tatttttctt  24840
gcctaattgc tttggctaga actccttttt ttaaagattt atttattttt tcatgagaga  24900
gagagaggca gagacacagg aggaaggaga agcaggctcc atgcagggag cctgttgcgg  24960
gactcgatcc tgggactcca ggatcgcacc ctgggccaaa gacaggcact aaaccgctga  25020
gccacccagg gatccccctg gctagaactc aatactgtta aattggaagt ggttaaagca  25080
ggcatctttg ccttgttcct gaactttcgg taaatgcttt cattctttca atattgagta  25140
tgatgttcac tgtgggtttt tcatacatgg cttttattat gttgaagtag ttattttcct  25200
agttcattga gtgttttctt ttttaaagat tatttattca tagagacaga gagagagaga  25260
gagagagagg cagagacaca ggcagaggga gaagcaggct ccatgctgag agcccgtcgc  25320
gggactcgat ccagggtctc caggatcata ccctgggctg caggtggcga taaaccgctg  25380
cgccaccggg gctgcccctg tttgtttgtt tgtttgttta accatgaaaa aacgtagtat  25440
```

```
tttgccatat gctttctctg catcatttga gatgatcatg tgttgtgttt ttttcttcat  25500
tctgttgacg tggcatagtg tgttgataaa tttttttaaa catgttgcta ttcatttttt  25560
aaaatttttt atttatgata gtcacagaaa gagagagagg cagagacaca gacagagaag  25620
cagtctccat gcaccaggag cttgacgtgg gactcgatcc ggggtctcca ggatcgcgcc  25680
ccgggccaaa ggcaggcgcc aaaccgctgc gccacccagg gatcccctaa agtttcttta  25740
gttgtaaaat caggttgtag atttaatatc tttattgttt ttttaaagat tttttaaaaa  25800
gtaatcttga tacccaacat agggttcaaa cacacaaccc caagatcaag agtcacatgc  25860
tctaccaact gagccagaca catgtccttc ttttttgtat aaggtaagca tttataacac  25920
taagtttccc cattagcact acttttgctg tgttccataa gttttgggat gttgtatttc  25980
cattttcatt catctctaag tattttctaa gttgatccat tggtagttta aaactatatt  26040
gtttgcagtt tggtgaattt tcctattttt tgttatgatt tctaaatata tcctattgtg  26100
gtcaaggaag atattttgta tgatatctta agatctgttg aaaatttgtg gcctatggtc  26160
tctccttaaa agtgtcccat acagagcagc ctgggtggct cagtggtttg gcactgcctt  26220
cagcccaggg cataatcctg gagacccagg atcaagtccc atgttgggct ccctacaggg  26280
agcctgcttc tccctccgcc tgtgtctctg cctttctctc tctctcaaga ataaataaat  26340
aaaatcttta aaaaaaaatg gcctatacac acttgaaaag aatgtgtatt gtgttgtgta  26400
aagtgttctt tatatgtctg ctagatttag ttggcttact gtgttaaatc ctgtttcctt  26460
agtcatcttc tgtctggttg ttctattatt gtgaatgggg tattaaaatc tcctaatttc  26520
cctggaatat ctttttttcct tcctttcaat ttcaactggt ttgtgtcatt ggatctcaac  26580
ggagtctctt gtagacagca tctagttgga ttttgtgtgt tttacaattt tatttattta  26640
ttcatgagag acacacagag aggcagagac acaggcagag ggaaaagcag gctccctgca  26700
gggagcctga agcaggactc aatcccagga ccctgggacc ataccctgag ctgaaggcag  26760
atgctcaacc actgagccac ccaactgcct catttgtgtg tattttattt tattttattt  26820
tatttaatat atttaaatat tataaatatt ataaatattt tttatttatt catgagagac  26880
agagagagag gcagagacac aggcagaggg agaaacaggc tccatgcagg gagcctgaca  26940
caggactcga tctgggactc caggatcaca ccctgggcca aagtcaggca ctaaacctct  27000
gagccaacca gggatcccct tgtgtgggtt ttaaattgaa gtataattaa cagagtgtta  27060
gtttccaatg tacaatataa tgattcagca gttctataca ttgcttagtg ctcaaggtaa  27120
gtgtactctt aatccctatt acctatttca ccattcctgc ccccctcccc tctggcaatc  27180
accaatttgt tttctgtatt ttagtctgat ttgtttgttt cttaaattct acatatgagt  27240
gaaatcatga tatttgtctt tctctagctt atttcactta gcataatacc ctcttagtcc  27300
atccatgttg gatcatgtgt tttatttagt ttgccaatct ctgtcttttg attggagagt  27360
ttaagccatt tacatttaaa gtaattttaa taaggaggaa attctctcat tgtgctattt  27420
gttctctgta tgcctcatag cttttttttgt cctccatttc ctgtattctt gccgtctttt  27480
atgtttattg attttttttt tgtaatgaga tgtttaaaac tcctttctca ttttcttttg  27540
tgtatatcct acagctattt tcttcatggt tagcatgggg attacattta acatcctaga  27600
gttaaaacag taatttgaat ttatacttta gcttaacttc aataacaaga aacaaaataa  27660
aaacaacctg ttccatcccc accccttttg gttattgtta tcacaaagct acctcttggg  27720
atccctgggt ggcgcagcgg tttggcgcct gcctttggcc cagggcgcga tcctggagac  27780
```

```
tcgggatcga atcccacgtc gggctcccgg tgcatggagc ctgcttcttc ctctgcctgt  27840
gtctctgcct ctctctctct ctctgtgtga ctatcataaa taaataaaaa ttaaaaaaaa  27900
ataaagctac ctctttatgg gtatataact gtacccaaaa acataaactt atatattttt  27960
ttaatgcact ggtcttttaa gttatataga agatcagatt tgaagttaca aatcaaagtt  28020
gcaggaggca cctgcgtagc tcagtcagtt cagcatcaga ctcttgattt tagctgggtt  28080
catgatctca gggtcatgag actgagccca gtgctgggct ctgtgctcat cttgaaggat  28140
tctctctctc cctctccctt tgtccctcta cccccaacac tggtgctctc actcgctcat  28200
tctctaaagt aaataaataa ataaaatatt taaaaaacaa aacaaatcaa agttgcagta  28260
atactacttt tacactgata agttttcttt aaatgtgtgt gtttgtttct ttttaaagta  28320
agctctatgc ccaatgtggg gcctgaactc acaaccccaa gatcaagagt cacatgctct  28380
attgactgag gcagccaggc aatcccagat gcattagtct cttaaatcat gtagaaaaca  28440
aaaagtacta ttacaaacca ttgttatagt tatactggct tttataattg tccatacatt  28500
tatttgcctt tattgaaatt tttgtttctc aatagggctt ctggttaata tctagtgccc  28560
ttttgtttcc tgttgcagga cacatctaat ggtcatgaac tccctcagtt tttgttacct  28620
gggaatgtcc taacttcttc acttttgaag gtcagtttta ctggataata aggttcttgg  28680
ttgacagttt ttgttgttac cgttttcaaa gcagtttgta tctattggcc cactgtgttc  28740
tggcctgtaa tgttttaaat gagaaatctt ttgattgggg atccctgggt ggctcggcag  28800
tttagcgcct gcctttggcc cagggcacga tcctggagtc ccgggatcaa gtcccacatc  28860
gggctcccag catggagcct gcttctccct cctcttgtgt ctctgcttct ctctctctat  28920
gtctatcata aataaataaa taaatcttaa aaaaaaatct tttgattatc ttattgagga  28980
tcccctgtgt atgaggattt gctcttctgc ggcttttcag gattctcttt ggcttttgaa  29040
agtttaatta taatgtctct cagtgggtct gagattatct tggagttacg gagctgcttg  29100
aatgtttgtc ttcatgcctt ttcatcaagt ttgagcagtt ttcagccatt atttcttcat  29160
gtattctctg cccctttctc tctcctgctg ggactcccac gtgtgtatat tggtcttctt  29220
atggcgtcac acaggtccct taggttttgc tcactttcgt gttgtgtttc tttgtttctc  29280
tagaatttcc atcatcttac cttcaagttt gctcattctt tcttctgctt gctcaaatct  29340
gcctttgaat ccctctagcg tatttttcac ttccattgct gtgcttttca gctccagaat  29400
tattttggtt tgctctttaa gtctgtcatt tccattttac tcacacatca ttttctttat  29460
ctacatcctc tagttctttt catgtctttt ttttttttta atttatttat gatagtcaca  29520
gagagagaga gagagaggca gagacacagg cagagggaga agcaggctcc atgcaccggg  29580
agcccgacat gggattcgat cccgagtctc caggatcgcg ccctgggcca aaggcaggcg  29640
ctaaaccgct gcgccaccca gggatcccct tttcatgtct ttaaaacaca tttgtcttaa  29700
agtcttggtc tactgtatct gccattaggt ctttcaggga cagtttctgt tgatttattt  29760
ttttccttgc catgccctat attttcctgg ttttgtatgc cttgtgattt tttgaacacc  29820
agacatttta atttgatcat atagtaactc tgggagtcag tctgatcctt tcccaggttt  29880
tgctggtttt ggttattggt tttgttcctt agattgttgc aggctgtgtc tgtgctgagg  29940
atcagcctga ggcataaggt taaggttttc tcaggtcttt tgagactttc tctgggcatg  30000
catggtcact ttctagtctt ctctgtatat gtgatcatat tttgaatatc ctagttttca  30060
atgtctggct ccccaaaggg agaaaagtga aaaatgaagg ggaggttgtg gggaggatgc  30120
cagtcctttg aataccttgg cagtcacttg agcctcagct ggagagactt gcagtgaagg  30180
```

```
gggcaggtgt gtgcaacagt ggctgcccac ttctgcatct ctggccagaa gcagtaatcc  30240
gtgcagattc ctgatatttg aacagaatct ttttggccac ccaggttcct gcaagctgtt  30300
gcaaactgct ctgtgaatat ggctagtggt ggggttgttg ctactctgct aggagccaaa  30360
gttaaccaaa attgctggca actgacggtc ctgttcttcc tggaagttat aagcctttag  30420
gttctgtaca gttctaaaat ggttacatca gacaaattct gcttgtgcaa ttagtgtcct  30480
agagcaggag agatttctgg tattctcaca ccaccatctt tctagaatct tcctaaactt  30540
catctattcc ccatcacttg aaatcacctg aatcagggat ccctgggtgg ctcagcagtt  30600
tagcgcctgc cttcagccca gggactccag gatcgagtcc cacatcgggc tccctgcatg  30660
gagcctgctt ctccctctgc ctgggtctct gcctctctct catgaataaa taaataaata  30720
aaatctttaa aaaatcacct gaatcagtac taaatttcta catgaatttg aacctgtttc  30780
taagatctgg ttctcatgca cctgtggcaa ttacttactg tttagcttga aattttccta  30840
ttaagggaat attgctccca ttattgctcc ttcagaattt cccccgtttt tttggcgtgt  30900
tttttccccc gatatgaact ttaaagttag cttgtctgat tcttggtggg aaatggttat  30960
tgagatcaaa tttaaaaatt gattaaactg gggatccctg ggtgactcag cagtttagtg  31020
cctgcctgtg gcccagtgcg tgatcctgga gtcccaggat cgagtcccac atcgggctac  31080
ctgcatggag cctgcttctc ctcctgcctg tgtctctgcc tctctctctc tctctctgtc  31140
tctcatgaat gaataatctt tttttaaaaa aatggttaaa ttaagtatag actgtgacag  31200
actttggtcc aaaaacatgg gtttatgcct tcccatttgt tctagtggtc tgtgtctcag  31260
tttccaaact tttatcactt aggtctacag attttagaag gttcacctcc tggatgttat  31320
aaggtctttt cttctgttaa aacatataaa cgtgtgtgca tgtatgtata tatgttttat  31380
ttaagtaatc tctataccca ccatagggct tgaactcata accctgagat caagagttga  31440
atgctcttcc agctgagcca gccaggcacc tctcttgttg tgtgtgtgtg tatttaaaga  31500
ttttatttat ttgagagtgc acacacaagc agggaggagg gtcagagagg gagaagcaga  31560
ctccccactg agcagggagc ttgatgtggg gctctgtccc aggaccctga gatcatgacc  31620
tgagcctaat gaaggcagat gcttaaccaa ctgagccacc caggcaccca ttattttgta  31680
actatagtta cttataggaa agatactgac tccagctgtt ttgttgaatg gttgagttgc  31740
ttttagttga cataactgga gaaaaaaaaa tctccacact caacatggag cttgaactca  31800
caaccctgat tgagtcacat gctccaccaa gccagcccgc ccccgaacaa gttttaacac  31860
ctttttgtct aacttgttag aaggaaacta atttgtgggc agcccgggtg gctcagtggt  31920
ttagcaccgc ctttagccca gggcatgatc ctggagaccc cagatcgagt cccacccacg  31980
tcaggctccc agcatggagc ctgcttctcc ctctgcctct ctctgtctct catgaataaa  32040
taaataaaat cttaaaaaaa aaaaaaaaaa ctaatttgtg taaattttta attttgattt  32100
aatcctttgt ctaatttctc taagtagtat acccaggata ttaattatgc tgagcaaaca  32160
tgtatctcaa tcctaaggaa tatgtggagg gtttggttca gcaggttaaa tttttaccgt  32220
tttaacgagg ttagtgagaa ttcatctatt ccacttttca ggacttatat ttggaatgaa  32280
ttgtaggtct cgacccctga gaggagatct tttcccttct catttcttat tcatgttatg  32340
agctgcatgg tagaagccct gataccaccc ttgcatttct gtgatcatag ttattccatc  32400
cccaggatcc tcactttgtt agacatttta ggattttttt ttttcaatgt gccgtttcaa  32460
tctactactt acgattttaa ttcctatcat gctttgtcag gttttaaatc aattcttcag  32520
```

```
aagtatctgg aggctcgtta catgctcaag tttaaccctt gtttgtcatg tgatcatcat  32580

tcatccgtga aaatacgtgg gctttttctt atttagtaac tgatctattg taatcttatt  32640

tccaaccagt tttaaggctt acgccatttt ccttcatcgg ctggtttatc ttaacattaa  32700

tttttatacc tcatttttaa caatttccta tattcctgat ttactttcct catctgtttc  32760

aggctgtgac tccccactga gccccataac ctctctgtgg tccactgcct ctgctgtaca  32820

acatgagggg tctccccttt gtaagggggt cacacaatag ctggacatac tctccaactt  32880

tggaattttt tttcctcttt tcaggctcat gtttactaac aattagtacc aagaacataa  32940

tataccacca tcctatacta taccaccaaa tattagatgt ttttcttttt gttggtgggg  33000

ccaccaccta aaccttccgg tagtagtggc tctggtgtcc caaccagatc ctggaagatc  33060

aggtagcaga atttcacatc ttgcccaccc cagcttactc tgacttttgt cctaatcctc  33120

tagggctgca ctgtccacta aggtcaccat tagctacatg tcccaactga gtgtttaaat  33180

tgtggctggt cccaactgca agtgtcggaa gtatcaagtg ccgcatcttg aaaacggtat  33240

cttacatttc tttagtaaaa aaatgtcagt acagtttctt tttactattt caatgtgtct  33300

actagtaaac ttaaaaatta catatgcgac tgcaccgtac tgccttctcc cctcctccct  33360

cagctccctt cccggactac atgcgaggct ctgggagcac agacaccact atcttcctgg  33420

aaccctcaga cgacagtagc accatgatgc caggtcagtg ttagtattta ttttaaaaat  33480

acacaaaata taaattttta catcaaagtg taatgatctc acttatacat tgttccatac  33540

ttacctggtt ttgtttgcat ccttatgcaa acattaatag atggatttga ttctgatttt  33600

ttgctagggt tcatgtaaac agctgagact gctacataaa gtggttttaa aaggtaaggt  33660

ggccacagaa acccaatggt gaaagaagaa ttcgatttgg tttgtttaat gaaactggca  33720

gaagtcttag cacataggta a                                             33741
```

<210> SEQ ID NO 3
<211> LENGTH: 2328
<212> TYPE: DNA
<213> ORGANISM: Canis familiaris

<400> SEQUENCE: 3

```
tacaagattt gggtaccctg gtttggcgtt tctcaatatt tagaacatac tcatataaaa     60

aaaaaagatt aattatctgt cacttagatt tatctggatt cttatatctt atctggcaac    120

cctgctggtg tgaagccaaa aagttttgtc tttgttgtca aaactgcagc atcttactta    180

ccaaaatggg caaacagaac agagtagaac atcaacagaa aaatcccctc catcttatcg    240

ttctggattc catttttttc ttggttttga tttccttgtg gtttttgagc ctcagagatt    300

tctcttactt tcaatgggaa gtctcaggat tgggcttttt ggaaacaaaa gaccaaaagt    360

cttgcaggcc acttctgctt cttgaattcc cacataccac tcccaaggca accagtacag    420

acctactgac ccagtagaac atggattgag ggcaaaatat agaggaccaa gatatgcatt    480

gctattttca acatatgatc cgcccacaca gataaagggt ttgcctagag ctgttggttg    540

tgtgaagtca ttattgcggt aattgaaaag gactcgtttc ttcttctcat tgtgctgcag    600

caaaggcttc gtggcaagcc cagcaggagc caagggaccc accccatgga gagccgcggg    660

gtgatggagg cagccaatgg ctgcaaggat gccttggatt tcaaccccat gaaggaatac    720

atggtcctga acagttccca aaggatagct gttgcggtgc tatgcacctc cctcgccctg    780

ctaagtgccc tggagaacct ggccgtcctc tacctggtcc tgtcctccca ccggctccgc    840

aggaagccct catacctgtt cattagcagc ttggctgtgg ctgacttcct ggccagtgtg    900
```

```
atctttgctt gcaactttgt aaatttccac gtcttccatg gcatggattc caaggctgtt     960
ttcctactga agattggcag cgtgaccatg accttcacag cctctgtagg cagcctactg    1020
ctgaccgcca ttgaccgcta cctctgcctg tgccacccat ctacatacaa agccctactc    1080
acctgtggga gggccctggc aaccctgggc atcatgtggg ccctctctgc attggtctcc    1140
tacttgcccc ttatgggatg gacttgctgt cccaatccct gctctgagct tttcccccctg    1200
atccccaatg actatttgct gggttggctc ctgttcattg ccttcctctt ctttggcatc    1260
atctacactt atgggcatgt cctgtggaag gcccatcagc atgtagccag cttggctgaa    1320
caccaggaca ggcaggtgcc agggatggca cgaatgaggc tagatgtgag gttggccaag    1380
accctggggg tggtgctggc tgtccttttc atatgctggc tcccggtact ggccctcatg    1440
gtctacagcc tgaccactac cctaagtgac caggtcaaga aggtcttcgc cttctgctcc    1500
ttgctctgtc ttgtcaactc catgatcaac cccatcattt atgccctgcg gagtggggag    1560
atccgctcct ctgccttcca ttgcctggcc cactggagaa ggcatctgag gagacttggg    1620
cttgaaggaa acaaagaagt cccaaggtcc tcagtcactg agacagaggc tgatgtgaaa    1680
atcaccccat ggccagattc cagagtccta aactgccctg attgctgatg acacctcttc    1740
cacagtttta aaggagctga gtcagaatca tttcactcct cagaggaaag agagcagcct    1800
tgaccctatt gtcttacttg agtcaggctc caggggctta gacacttacc ccttttttgtt   1860
gataactgat gtctctaaca cctggcaggt agcctggctg tgcctatttg catgagactg    1920
ttggatagct agaccctgtg aggagtggca aggtgggcga gaggattgtg caggctcagt    1980
gcacattcag attacagaac ctccccaaca aaatagctta gtgtttacat cttccagaga    2040
ccccaggatc cagagggagc ctgcaggctc accaaagagg aactcagagg aaatctagaa    2100
ggtgaatgga ttatgttcct gatatctcaa gatgtcaggt aggatagctg gccaacaatg    2160
ttcttgcttc attgttggga catccttggt tctaaggcta tgaaagaccg cactttctgt    2220
cacctttgcc tgctgaggac caaaaacttt gatacagtaa ggattaagca tgttgattca    2280
cctctttcac aggtaattga caagcctcta gttcagggaa tcttatta                 2328
```

<210> SEQ ID NO 4
<211> LENGTH: 7690
<212> TYPE: DNA
<213> ORGANISM: Canis familiaris

<400> SEQUENCE: 4

```
cagttactga atttcttcct ctgtaaaatg ggaaaaatga gaagaatagt aaatgagttg      60
acatctgtaa aacctttaga atagtgcctg gccccacagg gtgagtgttc tcaccttctt     120
tggaggctat atatgtcaga gaaccctcct cttcccaaac agctttccat gtatgagagg     180
gaaaatacgg atctgtaatg catgagcaag aaaaactttg aaagcaacca aataaacacc     240
tagaaatttc taatccatcc taactgcccc ccactatccc cagggaagct gcatgctgac     300
ctctgatgag gacccctgcc ctaaaagaag cagctgaaga tgccagcaga gggagagatt     360
ttccaccacc agtgccaata ttagttcttc tggagggcaa agaggaactg atgagctcac     420
tctggatcag aggcagtgag aaggagagag agaatgagac tcaaatttcc agaggctatt     480
tcagttttct tttccatttt gtgcaatttc acttatgata tcaagcaata tgtggctgct     540
gttttggaaa ctccccttgg gggggcaccc cctctactgg cctgactcta taaagggcca     600
gcctgagctg cagaagatcc cttcagagga tcctgagaca gcaggtggct ctccatcagc     660
```

-continued

```
aggtaccatg aaggtctccg cagctacctt tgcaatcctc ctcgccactg ctaccttctg    720
tgctcctgcc tctgcctccc catgtaagtc aggtcctgat cactgcagcc tggggccaga    780
ccctcacact ggcccagact ttgtcctcct ttcaactgca gcatttaggc ttcttgaacc    840
cgatgcttta tattcctata tatatattcc tatatattgc tttacccagc tgtccagctg    900
tccagctgtc cctgagagat ctttaagcca ctccatggca gggaccctct gcttaacttt    960
tctgtcttca agatctatac caagcccttc aggtgctgag cgcggactga tgctggggat   1020
atttgcaggc agaggcagct tgaactgacc tcaaaaccct atcaccagga gggtttctca   1080
gaaacttcta agcttgggat agtcatattc tccctgtttc atagatggaa aaagtgggcc   1140
ctgagagagg attttttaa ttttaatttt tttaagattt atttgagaga gaatagaggg   1200
gaggggttga gcgagaagga aagaaagaat ctccagcaga ctctcactga gcaaggagca   1260
ctgatgcagg gcttgatccc accaccctga gatcatgacc tgagctgaaa tcaagagtgg   1320
gatgcttaac caactgtgcc acccagagga ttttttaaaa acctagtatg gaccatgtat   1380
tatgctgact gctctgcatg taccatgtca tttaatactt cccatgactg agtggctgag   1440
cttgactgaa agacggagaa acagaggctc agaggagtta agtaacttgc ctgaggtcac   1500
atagctagga aatagggaaa ctggtgttca aactcagtac tgtctggctc ctaaacactc   1560
ctactttact gggaagtggc aactgacacc ttccagggtc atcctgaatt aactgaccaa   1620
tagaaagctc tccttccctg tttggaggcc ttcttaccat gcctcagcca gagactccca   1680
ggacacaata cacatcttca ggcccctctt agcggttgag gctgagccat gaagactgaa   1740
ttttggaagc ctccccccaa cccactgtag gtctcaaaga aactaagttc tgaatccact   1800
gaggatcaca agagggcaag aataaggaca aagagcccag acaagccagg aggaagccca   1860
tgatatccat agaaccaaag gcagaggatt agggtgtaga gggaaggata catgcaaggc   1920
tcaaggatta gatagaagat tgtggagatc ttctccgtcc tctgttggaa tcacccactc   1980
tgctactgtg tatccacagc caagtgactt tacctctcgg agcctcagtt tcagccaaag   2040
aaggataaca gtctatccaa gataatgtac ccagcacaat accccatgta taatggcaat   2100
gagtacagga gtctactgct ttctcctcct agatgcctca gacaccacac cctgctgctt   2160
tgcctacatt tccggccgac tacccttcac ccacgtccag gagtatttct acaccagcag   2220
caagtgctcc atgccagcag tcgtgtgagt cccagccctg tggaccctct ggggggggca   2280
gggggggatg aggaagggac accttttgtt ccagagccag tcccccacag gagccctcta   2340
agagcctacc ctatccactc ccacccatct tccagctgct caaatagcca gagttcctcc   2400
atccgtagct tcagatcccc ccctaacctt tgtgtagaag gattaggcag gggttcctgg   2460
gggatccttc cccactctga tggagtggat caggtctctg atctttatgg gtgtacctac   2520
aatgtccctg catggagaca agattgacat agccatctct ctcaactaag aatcccatgt   2580
tctcccatat gccacaccca atcaaatcta cctgcaacct cagaggatct aagaaggagc   2640
agtcagaggt cagagagccc tagttacagt caaatgtact ttaaaaaaaa attatcaact   2700
ggtgaagaaa taatgacatg agattctcct ttaaatatgc aaactaacac ctgaaaaatt   2760
aacagtcctt actacctggg atccctgggt ggcgcagcgg tttagcgcct gcctttggcc   2820
cagggcgcga tcctggagac tcgggatcga atcccacgtc gggctcccgg agcatggagc   2880
ctgtttctcc ctctgcctgt gtctctgcct ctctctctct ctctctctct ctcactctct   2940
ctctgtgact atcataaata aataaataaa aaaatacctt taaaaaaaaa aaaaaacagt   3000
ccttactacc tagaagtgtg tatcaaatgc cttacatgga ttatctccaa atttcatcac   3060
```

```
aacaaccctg acaggtatgt gtaattctct gcatgtttca gataatgaat ctgaaaccta   3120
gaggtttgga gacttgccca aagttgcaca gtaagtgaag gatggagcct gtcttaagag   3180
tctcctcttt ctactaccga cagctcaaca gtgacagttg cttaagaagt ttaagataat   3240
agagacttaa agaatgaaaa gggggtaatc gtgaagtttc ctctataaag tgaagttttt   3300
ttaatccaaa aattcctgtg acacttgcaa agccatatgc attcaagaat tgcctttttt   3360
tctggtgaat ccttcaaagt gtcatggtaa tatctagcac tactaatttt atttctgaaa   3420
acatattttt caaaagaaaa aaacaatcct tctttgagca cctgttatgg gcaggtggag   3480
atgaaaaaaa cactatccct gccctcatgg gactcacagt ctaatacaag gcagtgagat   3540
acagaatgat tagagcagtc ctgtgtaaaa aaacagtaca gaagggcagc ccccatggcg   3600
cagtggttta gcgctgcctg cagcctgggg tgtgatcctg gagatcaggg atggagtccc   3660
acatcaggct ccctgcatgg agcctgcttc tccctctgcc tgtgtctctg cctctctctc   3720
tctctctctc tctctctctc tctctctctg tgtgtctatg aataaatcaa taaaatcttt   3780
aaaaaaaatt tttttaaata aaaaataaaa acagaaggag ggagggagca cattcagccc   3840
cggggattag tggatgtttg ctgcaaaagg tgcttgagaa aagcctgagg gacaaggtat   3900
gttaggcaga ctgagtgtcg cctggacgct cttttggttg atgcagcatc cctgtgtaga   3960
aaagcagtgg tgggcacttg agcatcagca caaggactca aaagtgttag agcaagtgaa   4020
gtgaatgggc acagagaaag cctagagagc caggcccagt gaagtggctg ttatggttac   4080
ccatgtgagt agtattaagg ctaaacagga cctgcaggaa agtagagggt tggaaactgt   4140
cacgtatgga gtcggcaagt cctggcaggt gaggggaggt caggagcaag gacaagaagg   4200
gagctaagtg accttgaggt ttctagccag agggctaagt gaccctgagg ctggagaagt   4260
gtggcactcc ccgaagtctc aaggaaaaac tgtttagagg ataaagctaa gatgccagca   4320
cgacaaccct gtggcaatgt ccagcaggag ttgttagcca ggaagcagtg ttgggcatag   4380
agataagaca ttcttttgta ggaggaaaga gtctcctgag aggagagtag caatctttag   4440
cagagtcttg gtaagcgctg gctcaagtgc tcagcaagtc aggcttcatt agaatcccag   4500
ctctgccagt tgggcagttg caggagcctg gacccatgag ttaacgtctc tgagcctcca   4560
tttcttcagc tgcaaagtgg agtgaaatag aagtacttgc ctcactgggt caaagggaga   4620
ataatgagat gaaaaacaaa attggaatag gtcctggcac acagttggta cctgataagt   4680
gttcacttct cctcctcctt ctccaaaggt aatattatat acatagaagt gacaaaattt   4740
gatgagtgca attcattcat gacctcatgc tataaacatg gggcattaag ccccctcagt   4800
gtgccacacc tagggccaga aactagggag aaaaacacag aaaggggcag caattctgag   4860
aaacacctgc actcaagggg caggtggaag tggttgctcc ggaaagaaca agcaggaaga   4920
gagaggcagg agggaagtca ggcaaggagg gggtccccaa aatgggggca gaaagaagct   4980
tagccaggga ggttgttccc cagtctcaca ttcttcagga ggaaatagag gcctgagaaa   5040
ccctcacccc agatattcgt ttcctgccct tttgatttcc tggccacaga cggaaggggc   5100
cgagaagaga ggataacaag tctgtaggat ttcctgtctg atgtggctga accagggcag   5160
ggtcattgtc taagttccct tactacccca aataaacaaa cactaggagg catgagagtc   5220
cagaatattc catctgctcc ctttctctct tctgcacatt ggaatggaag aaagagtgtc   5280
aagtggctct gagtctcaga aaaggggaag cagcttcctc aagagcaaac actatccagc   5340
atagaaccca aaaagaaacc aagaaatcct catcctcgcc agacgaccta agcttcactt   5400
```

-continued

```
tgaaaatatt tgagctcata aggtgcagaa aaacatccta aagaagccaa aaggagaaag   5460
gtccaagtag acagggctgg cccaaaagta agatgtgaac tgcgggcact gctctccagt   5520
ccacagtctc ccccaggtgg aatcagtctc ccagccaaca ggtgaggtag gcagctggac   5580
taagcctgtg ccccgcaggc ttttatacat ccaatgcatg ccatcaactc ctgtagagat   5640
aaggcccttc cctcccagtg gcctccacat tctagctggt taattggtag aagtgctttg   5700
acaccgggag tacctcgggg ctttcaccct ctctgagcat ggatgtccag taccaggacc   5760
tttggggtca tcttgctctg atccctccta aagaagaggt cccataacat tccaatgaca   5820
aaccacatgc ggtgttttcc aaaactccac aattccatct catttgagtc tcacaacaac   5880
agtgcaaaat aggaagtatt tctatttgta ttttagaggt aaacaaatag attcagaggc   5940
cctaggtgac ttgccaaggt gaatccacta ataagtgatg aaatcaagac tcgggggtca   6000
tgtccttcta tcattcaccc acacacacat agatgtggtt cgtttgttga gtgtctaccc   6060
tttgccaggc actgtgttat ctgaaggcaa atcgcatgtt tgttgtacca cttcttctct   6120
ttcacctact caaccataac tcagttccta gaagacccct ctttttttct gcatcttggc   6180
acttgttacc aggtctaaaa ccagaaatgc tgagaaaaaa ctagtgattg accagctcaa   6240
tcctagactc ctgagctcca tatgccctta gctctccagg ttgcgtacat atttctgtgg   6300
gggttaatat gcacacagat ctgcttctgg cttggagccc tacgattcaa cagaagagga   6360
aatatctttc cttaaaagct acaaatccaa ctttgttggc tccaagccaa cagctccaag   6420
aatcctccac tccagtacca tcatcatcat catccccttg tgtctcagtt cacttcacct   6480
ccaaaaatgg ctgtccaggt gctgaccaga tctcatcctg tcctcttctt ccacagcttt   6540
gtcacccgaa agcaccgcca ggtgtgtgcc aacccacaga agaaatgggt gcgggagtac   6600
atcaactctt tggagatgag ttaggatgta gggcatctgg aacctgaact catgcaaact   6660
ttcctactgc ttcttgctct tgtcctatgc agcttgggag accctcacca acccctaccc   6720
ccaccccttc ctgggagggc acagatgcca ccacccagta gcagttataa aagtagtagc   6780
agttataaat aaaagcctcc tccatctaaa gtttgcaaga gctccggagg ctctgctttg   6840
tgcacagaag gtctctaggc tcttgagttt caggcctctc agcttgaccc cagctctgca   6900
gtcaggaagg agatcaacaa gcctccagag acgaagatgg gaagaagact gggctccttc   6960
ggcaatgtcc catggccaca gctatcctct cagcccctca ctgggaaggg ctgactgata   7020
aatgtgagaa aacagctttc cattaaaatt ctcgctgcag tcaccaagct ggctcctagt   7080
ttgattttct cctcaggaaa tttccttcct tatgagcatt aagtgattaa cccatcttga   7140
atttaactga catgtacttt taatgcttta acagactttt tagtgtgtct cttcaagtat   7200
ttttttagga gttcagatca aatctttgca gaatgttttc tagtttggat ttgcctggtt   7260
gtttccccat aattagattc aggttaagca tttctggcag ggacactaca tgagagatac   7320
tgggtttctc agggcagcac atcagagcac atcggttcac tgctggtgat gttgagtctg   7380
atggcccgaa ggcccatgtt tttttgccac agtgggctcc ccactgtgtg ccaggcacaa   7440
tgctaggtat gggaggctgg tggggaaaaa agagagacga atgagccaca agccaccgtc   7500
tttaaagttt aggccaactg ggatccctgg gtggcgcagc ggtttggcgc ctgcctttgg   7560
cccagggcgc gatcctggaa acccgggatc gagtctgtcg ggctcccggt gcatggagcc   7620
tgcttctccc tctgcctgtg tctctgcctc tctctctctg tgtgactatc ataaataaat   7680
aaaaattttt                                                          7690
```

<210> SEQ ID NO 5
<211> LENGTH: 26613
<212> TYPE: DNA
<213> ORGANISM: Canis familiaris

<400> SEQUENCE: 5
tgtgtgcgcg cgcacgagtg tgcttggggg gtgcgctgga cgggcgcgtc tccgcagaag 60
tctgagcctg tctgtcgggg tgcgcgtgtg cctgtccctg cctgtcgctg cttcttccga 120
gtgctggggg ccgcacaggt agcggccccc agggagcgcc aagccccggg cgcggcgggg 180
gagctcgcca gccccagccg cggcctcgg gggcggccgg gcagcggcgg ggccccgccc 240
gggccggccc cgcgagcggg cgggagagcc gagggccggg ccgggccggg ccgggccggg 300
ccgggcgggg cgggcggggc gggcggggcg gggcgctcgg gccctcgggg ctgcccgcgc 360
gccattggcg gaaagttggc gcacgtcacg cggagggcag ctccctaaag tcgtgcacat 420
aacgggcagc gcgcactccg gggcggcttc tcggggcgca ggctgtgggg gccgcgcggg 480
cgagcgcaga gcaccccgcg agctggatgc ggcttcccgg cgcccgctcg ctgcccgcgg 540
cgccgccccc gaggtccgcc cgctgaggcg cccgtgcgct cacctgccgg cccgcgcgcc 600
atgggccagc ccgcgaaccg cagcgtcttc ttgctggcgc ccaacgggag ccacgcgccg 660
gaccagggag actcgcagga gcggagcgag gcgtgggtgg tgggcatggg catcgtcatg 720
tcgctcatcg tcctggccat cgtgttcggg aacgtgctgg tcatcacggc catcgccagg 780
ttcgagcgtc tgcagacggt caccaactac ttcatcacct ccctggcctg tgctgacctg 840
gtcatgggcc tggcggtggt gccctttggg gccagccaca tcctcatgaa aatgtggacc 900
ttcggcaact tctggtgtga gttttggact tccattgacg tattgtgcgt cacggccagc 960
atcgagaccc tgtgcgtgat cgcggtggac cgctactttg ccatcacctc gcccttcaag 1020
taccagagcc tgctgaccaa gaataaggcc cgggtggtca ttctgatggt gtggatcgtg 1080
tccggcctca cctccttctt gcccatccag atgcactggt accgggccac ccaccaggaa 1140
gccatcaact gctacgccaa ggagacgtgc tgtgacttct tcacgaacca agcctatgcc 1200
attgcctcct ccatcgtgtc cttctaccta cccctggtgg tcatggtctt cgtctactcc 1260
agggtcttcc aggtggccca gaggcagctc cagaagatcg acagatcgga gggccgcttc 1320
catgcccaaa acctcagcca agtggagcag gatgggcgga gcgggcacgg acatcggagg 1380
tcctccaagt tctgcttgaa ggaacacaag gccctcaaaa ctctgggcat catcatgggc 1440
actttcaccc tgtgctggct gcccttcttc atcgtcaaca tagtgcatgt gatccaggat 1500
aacctcatcc ctaaggaagt ttacatcctc ctaaactggg tgggctacgt caactctgct 1560
ttcaatcccc ttatctactg ccggagccct gacttcagga ttgccttcca ggagcttctg 1620
tgcctgcgca ggtcttccct gaaggcctat gggaatggct actccaacaa cagtaacagc 1680
agaagcgact atgctgggga gcacagtgga tgtcacctgg ggcaggagaa agacagcgaa 1740
ctgctgtgtg aggacccccc aggcacggaa gaccgtcaag gtactgtgcc tagcgatagc 1800
gttgattcgc aggggaggaa ttgtagtaca aacgactcac tgctgtaatg cagcttttct 1860
actttttatg aaccccctcc ccgcaacgaa acactataca gactatttaa cttgagtgta 1920
ataaatttag aataaaattg tatagagatg tgcaggagga gggacggcct tctgcctttt 1980
ttttttattt ttttaagctg taaaaaaaag agaaagcata ttcgagtgat tgtttgttgt 2040
acagttcagt tcctttttg catggaacgt gtaagtttgt gtctgaaggg ctttggtccc 2100
agaggacctg ggctgctat gttttgatga cttttccgtg gatctacctc attgatcaag 2160

-continued

```
tattaggggt aatatatatt gctgctggtc atctgtatgt gaaggagtct tttcttcctg   2220
caccccttgca ctggaggatc ttgagtatct cggacctttc agctgtgaac acggactctg   2280
ctggcccctc ttatttgctc aaacagggtg ttgttgtagg cagggatttg aggggcagct   2340
tcagttgtgt tcctgagcaa agtctaaagt ttacagtaaa taaattgttt gaccatgact   2400
tcattgcacc tgtttctcca aaaccccttg actggagtgt ggtcgcctcc ccccactgga   2460
aaccgcaggt aactatttgt aataaataac tgcccaggga cttaatatgg aatgatacag   2520
gaatggcacg cactgattgc ttaacccttt cctttgcctt tgactctgct gctgcgaacc   2580
tgtatctctc tcaatgccag tgcctcagag cagttgtgcc tgccgtcagc atagcttgtc   2640
tccctggtcc tatggtgatg attctgtgtt gttacatcag aaacactgac tcacagaaac   2700
ggagttacag gcatctgctt tgtccctcca cgcgccccca ctgctcacct tctagtccta   2760
cttgtttaac agctgcttat gtcatatatt ggctgcagat ctatatatag tggagatctt   2820
cgtactgtgt caggtttggc attttaaaga taaaggaaga agctcttatg cacaagctac   2880
ccagacagag cccttgtcat tccaagggaa accgaaaagg gcattggtcg tagggagaaa   2940
gctggaaaac acttaaccga tgaataaata cctcatgacc tcaaaacgag attgtaaacc   3000
ttcctcctcc ttctgtctct cttcctcact tcgatataaa gccagccagg cttctcagcc   3060
ttggcactgt taacgtctcg ggccaggtaa ttttctgggc gggggcctgt cctgtgcatg   3120
gtcagatgtt caacagcatc tctggcctct ctacccatca gatgccagca gcaccccctg   3180
aactgtgaca accgaaactg tctccagacc ttgccaaata ctccgtgagg ggtgaaatca   3240
cccctggttg agaaccacag atccaaggtt ccaaaatcta aacagggcag ccgcttgatt   3300
ttgcagagca tccgagaggg attttccatg gttcactggg ttagtgacag accccgggcc   3360
ggcgctcttc cctccacccc tccaccctgc catgctgcct tcccaactca ccttccagcc   3420
gccccgacac tgactgtatt tgtggggatg tgcattgttt ggtagggttt atccatggag   3480
gcgaggcctg tgagtctact gcctttttgt ggagagattc tagtaccgtt aagaggcaca   3540
tgagggaaaa tcacaaaagt aaacacattt cttctcccac cccctttcta tttttgcccg   3600
tgtgtctgag ccagagcttg gcccaggttt gaccgagtgg accgtcctcc ttggcaacgg   3660
cagcctggag aggatcagcc tgcaggttca ttgccattgc acccgctcac gaagccgact   3720
ccacttctct cttcccttct gtcccagcca aggtccccaa ccagagaagc tttggcttcc   3780
tctgcttcct gtcagcgcag tgatgggtgt ccgggtgcac atgcagctct cgggagaaag   3840
ctaggtgccc gagttttcag gacgtgcagt ggcaaattgg agagtgtgtg tgtgcccttc   3900
agcgctttta ctttttctcc aagggctttg ctgcctcttc tcacattctc ctcctgctct   3960
gggccccaca cccagaggtg cgggcagctt ctccagccag tcttcaccct cctggtggcc   4020
tcacaggatc ttggacttga aagagcccat agaaagcatt tggcgtccaa agagacgaaa   4080
aatctgtgag gggggaatgac ctgcccaagg taagaagcca aggatgtcag agacggggct   4140
gcagccgtag aacccagctg tcagctgtta ttcctggaac agatgtcttc cctccactgc   4200
atggccattg acttctgtcc tcgccctcca tggtggcagc tttctttccc tggggctgtc   4260
acagaacaaa ctcatgtcag tgggtgttac tgctctcagg tccttagcgc agaattcagg   4320
caatgaccaa ataaccacaa tagggataag agaaagaatt gttcttttac tcagcaagag   4380
tctactagga tatcctcagc gttggggagg cggggggaca gggaggagcg gggaagagat   4440
gcatgcttcc tcgacccacc aggaattata agccactcca ggtagaaatt tcaaggagaa   4500
aaaaatgtaa acttttctgt caccgttgta agtcctgtgg acaataaacg tgattaacaa   4560
```

```
caacaacaaa aaagttgtat ctatattctt ttggctagag aagcatctaa tataatttca   4620
cttaaaattt gggtacaagg atgtttagcc atattcgtgt tcctttagga atcctttaaa   4680
tataaaaact tcgatgagtt ttaagggtct tgacaaaaca gcattttacg tactgctcaa   4740
tcccttgcct tctgtcatct tttgttttgc gctttgagtg gggggaggcg ggtaggcatt   4800
tgtcagtgtc cctctgtccc tctgtttgct gacaggttgg ttacataagg tttgtgttgg   4860
attcatcatc ctaaagtttt ctttgcctgg acagcaagtt ctcagagtct gtcaagtgag   4920
aaccttatcc tgagatgcaa gctgacaggt gtgcaaagtg gcaggccagg gtgggcctcc   4980
ccactgaggt cactcttggg gggaaggaat ctggggaaaa aggagctggg aagtggggac   5040
tgttgacaag caatgcttag aatatttctg atgaaactac taccaaaaga aactcaggct   5100
ggatcgatca gggccattta tgcagcccct actgtgtgca gcatgagaag agtatacact   5160
tctgtagcat aagattaata atactaaaga gatccctttt ctggaatctt actaaatgat   5220
ccagacagtt ctagacacct ttttaggcat tacatcatct tgatagcctt atgatgtagg   5280
caatataatt gtcctctctt aacagatgtg acaacagagg cttggaaaga ttaagtaact   5340
ttccaaagac tcacaaacca gctagctgca gagtcaggac tggaacccag gtctccgtgg   5400
gtccaaaccc atgcagacca ggaagcagca caaggcagct cataatccat gccagaacgg   5460
gcataagaac tggaaacgca atacctcggt gagagaagag ggaggctgct atgggctggg   5520
gcagggagga atgtgccctt cgaagcatgt gactgcaggg ttgctgggga ctgggacagg   5580
aaaccaatca cccaagtgtc tagtttgttt ctctgagtct ttgctttgtc ttttcatcga   5640
gaattgggca aaggtgaaaa gaggatttca cacttgaaaa caagcatggg ctagagcaga   5700
aatgcagcct gcctcacatc ctgggaaatc atttttgctt ctgaagttgg gaagttctct   5760
gaaatggagc gggaacctag acccgatggg aagtgaggca gggctaggcg gccctggagg   5820
tgcaccatcc atttggagct atcgaattct agggtaaggg agatagtctt tggacagcag   5880
agagccatgg atgcacttgg aacgagacgg cacggacagc gtaatgtcca ataagttctg   5940
ccctgctcta atccctcctt cattgacagt gcaaatatca tttgaaggag gcatttttga   6000
aatacctaag agaacaaact tcccaagcac tctcaagggc ttaagaaata ctggtatctt   6060
atgaataata ggaggcaggg tgaaagaggc cggcactggg aattcatgcc gttaggttcc   6120
aggtctccac tctctctctc tttctccctc tctctttctc tctctctctc atgttgggtc   6180
aggcagttct cctcagtgga cctcatcttg cttgtctgta aaatcacgag gccagtgcag   6240
gtggtctcta agctctgctc aggtatgaat ttgtataacc attaatttag aagctaagta   6300
gagacactag tttgtaattc taattagaat tgatgacatt tgtcatataa ataatgactg   6360
agtatcttgg gggtggccag ctggcagagg agaatgttgt gaagacctat ttgatgcatg   6420
atacctgcct tcaaatattt aaggaccatc tggggaaaag gagcatatca attttacatg   6480
aataccgaaa ggcaagcaga agctcagagg aaggtcgatt ccccgctcag gtgaaaaaaa   6540
agactttaaa agtgaagtag gttatctatc agaatagtga gcttcctgtc attggaagca   6600
ttcggagaag cccaaataaa gctctgtgtg gtgtgaagta caaagggttc ctgcacagag   6660
caggagctgg actaagctcc ttccaaatct gtgcctccat gtccttgaaa acaatagacc   6720
tgaatgttct taaaaagtat tcagaccgtt ccctaattcc agctggcctt ctccccaatt   6780
cctctggatt tcagaggttt cactgcattc ctaaacagga aacctccggg ggaaatcagg   6840
atctcaacag tccttggcca tgggggggaaa tccagaaata gagaaataag gttaagcagt   6900
```

```
tttccaaact attagacctt ttcatcagct gctcttccca tgccttttgc aaatgaccta   6960
ctaactccca gagagagaat aatgagagct gcaaagtcct ctctgcaaag gctattacat   7020
acttctccac cctcagaatc agtgcacttc ctgtagtttt tccgtcaccc tcacagggca   7080
ggaagaaaag gaggcaggtc cctggaaagc acggagcact tcaaagccct ctggtccaag   7140
agcctagaga cctggggtct ctcacagccc agccactaac cagtagggcc acctcggaca   7200
ggtcactctc cttctctaga cctgttttca tcatctgtga tgagagatag tttggtttcc   7260
atgaatcttg tgtttccttt ttccagaatt ctgtacgatt tcaggaagta tttgatgcgg   7320
cacatctggc cgcaatgctt ttatttcaaa atcacatttt tttttttctc attagaaggg   7380
taatagatgc cctttgtaga acatttaaaa atatatgaaa tcacaaaatg agataaatca   7440
cacataacat tagcacctcg agagagccat tgttatatgt gttgtatatg cttccagtct   7500
ttgtcctgag cgtggcgatg caatgcgtat aggtatattt ttaaacgaaa atgaattaga   7560
ttatgaatac aactttgatc ccactgataa taattttgca aatgcctcct tgaatatctt   7620
ttatatataa tataatccag gtatcataac tggcctgaca atagaagcgg ccagcagttt   7680
tcaaactttg ggggtacaga ggaccatcac tcccagagca tctggattgg gaaatctgag   7740
caggggccca agaatctgca ttctagcaag ttcccccaag tgtttctaac attctaaagt   7800
tcccttgatc cccaaggatc acattctgat gaataagttt atggagataa attctgtcat   7860
ttatacagaa tgtcccctct cttccttgct agttgacaaa aaggtgttgc catacttgtc   7920
tctttgaaag catgctttct gcaaatgggc tctagttgct ttcagagcat aatcactaaa   7980
ctcctcgggt gaggttcttg ctgcatcgtt aaatgcctcc aacccagcca gttgatttat   8040
gttaaaataa gtccattcaa gttacatagt gaccaatacc tactatatga aaagtataac   8100
agcagatttc tatccacaga gcacctcttg ggagaataat gactatgaac tccagaggga   8160
tactatgaac ttggtatcat gcttggtggt ttttgcgagt gatctcattt agtgcttacc   8220
ctaaccctac agaatgggta caattgtgtt tctacccatt ttataaatag ggaaactgag   8280
acttgaaggg gttagctaag ttgccaacaa tgacgcagtc cactggagtg aaacagagcc   8340
catgtgcttt attgctagga tatgccgtct tccccccttg tggggtcagt taagagaaaa   8400
agaagaaaat gatgagaagg catttttatt tttatttcat tttttaaaag atttttatttt   8460
tttattcatg agaggcacag ggagagaggc agagacatag gcagagggag aagcaggctc   8520
cctacgggga ccctgatgtg ggaactccat cccaggatcc aggatcatga cctgagccaa   8580
aggcagatgc tcaaccactg agccacccag gtgtcctgag aaggcatttt taatgggcat   8640
gctttgtttt attctccagg gattctttca tgaggcctga ttaatttctg agccttgcaa   8700
ctgagaggca agcccctgcc atcgagggta ggctgtggct aagtatgaac gaggacacca   8760
gattgccctg aaagcgggca gcaccctgtc tttcaccatc attcaggcag tgtttctgag   8820
cttcccccac caggtaggaa gcagaggtgg gccgcctggt accagcacat tggtttgcgc   8880
tgagtcaaat cctgactgtc atggcaggaa gcccgtgaca tctggctttg gggtgctttt   8940
cccatctctc tgcccaggtc tgtactcgta tctgaggttt caccatagag aatatccaga   9000
tggcatgggc ggtgagcaag cccattactt cctaagtgta ctaagaaagc caaggctcta   9060
agaggtgggg tcggtgacaa ggtagcccag gcaccacgag aggaccatct ctcctggctt   9120
gttttattat tatttttcca gtgctgagag gggaagactg atgtttctga atatattcac   9180
ttcttcagga agagaaaaca gtgtttaaaa tcacaacagc aatactcatg acaaagcaaa   9240
attagaggcc tagggaactc ttgccttctt tcaactgtaa ctgcctttgt ctggagagtt   9300
```

```
ttcttcattg gacccattct gcctctgttc taccgtctag tgttcctctt tatttatgaa   9360
aatcctatta gatggtctta aatactgcag acaaccctga taatctgttg gtgggttttc   9420
attgttttca atttggttga gaagtgccca cagtgcagag atgcattgcc aactctaagc   9480
ctgttctgct cacaacattc agatttcttt cttgtttcac ctctgtgtct ctgtgattcc   9540
aaacaatcac ctggcctcct caacctaaca gaactgaggg ccagcctcaa gggcctcagg   9600
tggccagcct tagaaatctc tttctatagg atcgtggaag ggttagtgat gtcagtatag   9660
gtaggagttt cttggcgcta ttttatttta ctgcagtggg tcccaaaaaa tgatttgggg   9720
gaatttctga gaaaatgcat attcatgacc cccgtctctg agactctgat ctgacaggac   9780
tctggttggg agccagcaat ctgcattttg ccacgacgac tcccagagga ctgcgacgca   9840
ggtgctctga ggcaattcgg gaacctaatg ctagcactgt cttcccttcc ccgtcctttc   9900
cactgaagaa cacaaaatgt aggcatacaa aagaaatgat cctgtacagt tgcatacgtt   9960
cacacacaca caaaaaatca tcctatcaaa taaacaaata aataaatcga atcctgactt  10020
tcctgtgttg ccaaataaaa caatgtagat gaaaacaatt tgtatgtgat aaagaattac  10080
tctgactgac aataaaatgc ctagtcccaa accctcttca atataccggg aggtagcagc  10140
acaggaagac aagggatttt gctgcagtga tagactacta ctccagtgct ccttcctccc  10200
tgacaccaaa ccttggttaa atcaaactat attaaagtct atatgaatct atttgcccaa  10260
tgtacataaa ccctcctact tagaaacctg atgggggtcc cacccactac agagaagagt  10320
atgattcata catattgacc catacacctc tacacacagc tgcacacacc caaataaaca  10380
cacacacaca cacacacaca cagaatttta tgttgatgcc tatacctata tcaacataaa  10440
tccacacaag cgcatttcca catagctata tggccacata gactcagacc taaaccttag  10500
agaaatacac acatagagat tcctaagcat actttcgtgt gagcaaacat gccacgtctt  10560
gtaatcgtgg tcccactgct acctacatag gcacaagtcc gtgtgcagac ccctttttcct  10620
tggtgagtct atatgtcctt gattaaagca tgcgtactaa attcctatta agtgccaaga  10680
actgttagat gttgaagcac agtgagtgaa taaaaacagt tcatctgtgc ccttatggag  10740
tttgtatgtg atgagagaga acttttaaaa aatgcatgcc aagttgcaac tgtcgttagt  10800
gctgcagagg agatttgtgg tgttttgagg gaatctgact aattctgaga gttcggtaaa  10860
ggctcacaac cccacaaaga agtgaggttt caactaggag ctgaaggata gctagataat  10920
ctcttgaaaa agaaaggaga taagagcatg ccactcaggt agaaaagctt gtgcaaatgt  10980
cctggggtaa gaggaaacct ggtgcatgag acaaccgagc aaaggtcagt ttagttggtg  11040
tgcagagagg gagaatgaag cagggtatgg ggtaagcccg caagaggcag acagatgcca  11100
catgtgaagg gacttttagg ccacattaaa gatttgggtc tttatcccaa gggcttttag  11160
aagccactga tgtttacagt agggatcaga tttgtatcta ctctacaaaa gcactctcac  11220
gtagataaag gtgcacacaa gggttcacac agacagttgg gtgttgtttt cttagaaatg  11280
cacgtttaca tgtaaatatt catttaaaaa cagagcctct ctgaacacac tcttatgtat  11340
ttatgtgcat ggtattgaaa cccagcaagc atcagaggtg tggaaatata ctcttcgctg  11400
agtatcatca ggcttaagcc agtgtttggg ggtgggggct agattagtga tgtatcagac  11460
ctgatccaaa ccctctaact ttggagcttc gggctcttag gcttggcctc ctgccttcac  11520
ctcctgctcc gctcccactc ctcttggctc agagcacacc atgacaaggt ggggtttctt  11580
ccagaacatg atcattgact attcttggcc tgggcaagga ggggaggatg ggcaggtcag  11640
```

```
gttgcataaa gattgccttg tgccctctca gatttgtaag cagagcctct gcccagcacc  11700
aagctcggag cacccctttgc acaaagttgg tggtatcaag aagtaaatgt agcgatggga  11760
aaccagaggt ctgcaggtcc tggtggggac tgtgggggga ctccatgcag tgcattccat  11820
aaggaaccac tcactgcacg aaatgtgaca ctggaggagg aaacagacaa agccccgcaa  11880
gaaagccttt caaggcaaga tgtcccacag tggccccact gccctggcac agtgaacacg  11940
tgtactcaca tatttacaca tcaacaaatc ttgctctggt gggtgtcaca tctccccaca  12000
gagaaggtag caagaaattt atcagccaca acagtctgca ttctcttcct tccgaagaac  12060
tggaactaca tttgtgtgta ttttgctcct gtttaccagc aagccctcca gggccttaac  12120
cagagccagt gacagactcc agggaaatca gtaggaacat tcatgccgaa tgaaaggctc  12180
acctagagcc ttacgttcta aggccataaa gatggtccca agtgattttt tttttatatt  12240
ttaaagactc ctacccactg agattttttg ttttccagtg tgtgcttaga aatgctttct  12300
tctataatta aaaagaatta tgtaatgtaa cttgaagctc ttcttatttt gcttcaggct  12360
gtgtaaggaa catccttctt ttctcccagt tgggtgctct tttatgctat cctggcagtg  12420
agctactaga tccatcaagt gctgcagacc atagcactgt gctcaagggg acactgtggc  12480
ataacaatcc atattgatct agcacttggc agtttacaaa gagcttttat atctgccatc  12540
ttatctgatc cttacaactc tgaggtcagc atgcttgctc ccatttcaca gataagaaga  12600
ccaaggttag aagcacccag gtggctctgt cagttaagtg tcctgttttt gattttggct  12660
caggtcgtga tcccagggtc atgggatcaa ggcctgcttc gtgctccgaa ctcagttgag  12720
tctgcttgtt tttcttcctc agcttctgcc ccacttgctc tctctctctc tctctctctc  12780
tctctctctc tctcaaataa ataaatagat ctaaaaaaaa aaaaacaaag aaacactgag  12840
attaaaagat ttgcctaagg gcgtggagct accacatggc agggttggga cttgaactta  12900
ggccttcata gttggtcagg aaataactca agttgtcttg agctcaactg cccttctagg  12960
acttactcag gctcctctca ctgttcttcc ctgctttcgg cttgcatttt atcttataaa  13020
ttcagtgcta acactcccca gcaccgaagc cacagctgca aagctgcaga taagtgactg  13080
cctgctccag agacagtccc cgggatgttt tccatattga caagccccag gctagggtga  13140
gctcatgctg ggaggagacc acgctcagct ctgtcaactg tggcttaggg cagaagctcc  13200
aagccttttg ggttcctcat gccagtcacc agatgcactt tccccaagtg agagttaccg  13260
gataacatac atgtccagct ggagctcagg gctctactga ggccttgctt gttcattttt  13320
cccaattcct cttgcatcag gatgtttctg tgggaagacc cggtatgatt tgccccaatc  13380
ccacacccac tgggcacagc gcaacctgct tctaagggcc aagttccaca ccttggtaaa  13440
aattgcaggc tccaggaagt atttcagctt cttgaaaaca gcttgtattt ggcataaatg  13500
tcttatttta gtcagagcaa ttagatgttc ttgttttgca cacacttcca acagaattgc  13560
cttcagcaca ggtgaaaggt atttaatggt tctgggaaag cttgagatag tggccacatc  13620
ccaaccatga gaaacctccc tgttggcaac tgcttcctct cagagtgtca gcttatctga  13680
tttacttagc tctccaaaca acatttgatt gattgattga ttgattcatt cattcattca  13740
ttcattcatt cattcattcc ttgaaaagat gtttgaacac ttataaatgc cagagcctgt  13800
attagctaca agggtctatc tagctatctt ggtcacctaa ctatgaccaa gataggtgtg  13860
gctggctggt ccccgtgttt tagtttctta cagtctaatg gagaagacag acaatgaaaa  13920
gggaattata aatcatttgt ggatcacatt ccttagtatg cacaccagag aaacttaaat  13980
atattgatga aaaggggtga gagatgggca attggcttca caattttgct agctaggact  14040
```

```
aagaaatttg ctgaaggatc tgtcaacctc agactgactc ctacccatcc ataaaaatat  14100
taatgtcttc cctttaaaaa catctcaggg gggcacctgg gtgactcagt ggtcatggtc  14160
ccaaggtcct aggatcgagt cctgcgtcaa gtttcccaca gagagcctgc ctcttcctct  14220
gcctatgtct ctgcccctct gtgtttctca ttaataaata aataaaatct ttaaaaaaaa  14280
attttaaata aaaacatctc agggagggac acctgggtgg ggcagtgggt taagcatctg  14340
actcttggtt tcagctcagg tggtgatctc agggtcatga gatagagctc tgcatcagct  14400
ctgtgctctg tgtggagtct gcttaggact ctctctccct ttgaccctct acctgcacac  14460
tctctctaca cgccccccac cccccatctc aaataaacaa aacttaaata aataaataaa  14520
taaatgcacc tcagggaaaa gcatagttga cagtggcttc caaagttatc aatgatctct  14580
gtcttggtac atctctcgag tactgtgcca aattctgagg ccacattttt caagggaagg  14640
gggacatttg gggcccttcc aggcttgcca gatttagcaa gtaaaaacat aagacattca  14700
gttaaatttt aatttcgaat caccaacaca ttcttttttt catataaata tgtcccaaat  14760
actgcatgga acatacttat accaaaaaaa aaaaattttt tttatcagaa attcaaactt  14820
aactaggctt cctgtgtttt aatccaacag ccctacatta gagcaaagat agtgaagaaa  14880
tctcaataat gtgtctcaaa aggaaactta agaggagcct gactttttag cttggagaca  14940
atggtagtaa gaacctagat ttttgtaaag aagcattttc caaacatttt ccctaaaagc  15000
atatatggaa aatagtaaaa ggtacactga gagggaaaaa aaatctttcg aggtcaaaag  15060
ttggggaaac attgcatggc cagtcttccc attttggagc ttacactata cagaaacatg  15120
gtaaacgttc tgagtagact tgcaggaaac agacctggtt gacctggttt agcttagcat  15180
gcctacagaa tgccatttgt ggtcttttgt ctgtttgttt tgatatgttt gctttataga  15240
ggacatctat taacattgtg caaactggct actctgccca gaacaccttg gggacagtg   15300
gcataaaaaa aatgaaagtt cttttcaaat atccagagtg ctcccgggta gggaggaaac  15360
agatttagtc tttgtaaacc aaagggccga gctgtaccca atgcacggac acatctggga  15420
gacagattgc tggcctggta taaagactag aactttctaa caattataat agtctgaaag  15480
gtaatgagct ccctgtttgg agaccttaag gcaaaaatga aatgctatca gggacactgt  15540
aggaaattct tgttttgtgt gggaaattct ctgcatctgc taggaagggt gtattcacat  15600
aaaacacaga gaggtctcta ccagcaaaca gactttcaaa ttatgtcccg tgttctatat  15660
cctttctgca gtctgagtct atccctcttg aatacattgt tactgagttc ccttcccatc  15720
actgggccaa acctctcaag aatattagtc ctctcaagct aacgatcttt ggtctgatct  15780
gagcctcttc atagtctagc ctaccttgcg tcttggctct ttggaacccc accttgagcc  15840
tctgggagtg acttacagat ttcatgagta aactaaggct tacatctgag cttagtacct  15900
cggaagagga tggggtatgg agaaacttgg ccctatgctc ccccaggacc agtgagcttc  15960
ccccgggtgg gtgtctacag tgtggtagag accaccgcat acctgaggtg ctccacataa  16020
caaaaatcag tagagggtca aatcccaacc ccgcttcttc ctgagtctat gacctggaga  16080
aaattgtttg gcttctccaa ctttaatttc cctctgtgaa aaaaaaaaaa aaaaaaaaaa  16140
caagaatgat gataactgca tcacaatatc atgaaaatta aaagagatta agagagtaca  16200
ttccaaaaaa aaaaaaaaag agtacattcc aggcaaattg aacaccaata aaaaataaat  16260
ttattattat taaaaaaaaa aagagtacag ggatccctgg gtggctcagc agtttggcgc  16320
ctgcctttgg cccagggcgt gatcctggag acccgggatc gaatcccaca tcgggctccc  16380
```

```
ggtgcatgga gcctgcttct ccctctgcct gtgtctctgc ctctctctct ttctctctct  16440
gtgactatca taaattaaaa aaaataataa aaaataaaaa aaataaaaaa aataaaaaaa  16500
agagtacatt ccaaagagcc agcagagtgc gatacaaagt ggacattaag taaatgttta  16560
tttaatgtgt gactgggatt gctactgttg tggtaaagac tttcagagaa gttaaaagat  16620
ttctgtagaa cttcaacgat cggtgtgcca agatttcagg ccccagccaa aatctaatct  16680
agctcttgtc tagagctcta acaccttttc agaacttgtg cttgagaatg gaaagttatg  16740
catgtgtatt aaacatcaca gttttccttc ctgcgggtct tgggccagtg ctaggaaagg  16800
cattggattc gggggcagat tggtttaagt gactctgctt ccttttccgt gctgaactct  16860
ggtcctcatc tgtaaaatta agaggttgga ctgagatttc tctaggttcc gtgagctgtg  16920
cctttgagct gggggcgatg gatgcagatg tgtaagtaat ggtccctggt ccctaatgaa  16980
agaaagacct tgcccaacta aagcaatgtg tgtgtacatg tgtgtacaca gcaacgcgat  17040
ttgaagtcac tttaattgcc ccctgctctt gtgcctgtct ctaagtttga caaagaaaga  17100
gttgcaccag aattagctgt ggaggagtga cctcctgatg gggagagctg ggttcgagtc  17160
ccagtcctga ctctgctggc agagcctgtt ccccatctcc agggtgtgac actcccttcc  17220
gcccccacct tggcctcccc catctttcac gtgagacaat tggctccagg gtctccaagc  17280
tctgtgtctc ctgggaaagc gtctctgatc tattttcgct tggctttgca cgctctccgc  17340
aaggattctc atcgggatga ctcaagttct gcttctttct tttgtttcat ctgctctggt  17400
ttcataacac aagctctcca gccaatttta gcatttcttg gattatggga gtgtctacat  17460
gaaggtacca gagcactggt ctccttttct gcccaggatg ctggtctccc ccttccccgc  17520
cccgcccacc ctgacactcc cttccattct ggcacaagca gactccctcc tccccgctgg  17580
atgacacact aagtggagtc tgcttttcgc attagtcgag aggaggccct gaagtcagaa  17640
atccttggca catgactcac tttgtctctt tgtgcctcct ttcccccagt aataaatagg  17700
tggagtctca cactttctca cctcccagtg tttgcccccc cacccccagg gaggtgtttt  17760
tgtgcagagt gtcccctctt ttcacagatg ggctctctcg attatcatag ccccagggca  17820
ctctctagga aaacagtatg taccctccag acttcccttc attactgccc aagacacagc  17880
actttctaaa acacagaagt caacttttgc tgtaaagcct tccatggctc cctattacct  17940
tcaggataaa gacctcagca gagcgagttc acaaggaagc accccgaaga tgaatgactc  18000
atctgcacat acagcccccc tgacttgcac tccttccctg ggaactggaa tgggccaggg  18060
ggtacagtgg gaataaatag agaggggagc aggactcggg ccatgtgttt aagcttatgt  18120
gccttccaaa aagggaatag acattcaaaa ataataatgg ttttcttttt taagtactgg  18180
aaatggtctt agaaatcact ggcctggccc aactgcttca tttcacttgt ggaaatggat  18240
gtcatagaat tggcaaatta ttattttttt caaagatgta ttcattcatg agagacacac  18300
agggagagag agagagagaa agaggcagag acacaggcag agggagaagc aggccccacg  18360
cagggagccc gatgtgggac tagatcccgg gtctccagga tcacgccctg ggctgaaggc  18420
aggtgctaaa cctctgagcc acccagggat cccagaattg gcaaactata agagaccatg  18480
tctcttacta agtcgccggg tttctactct gcctctacta ccaggggccc ctctccactc  18540
tgcagccaga gtcatccttc caagggggat gggatgttgt cactccccat gtgaaagttt  18600
tctgtggccc caatgcagct actgaagaag ccaggcatct tcctggggcc agggagccag  18660
tgtggtttgg gtgcaaggta gacacacggc cccactcact ctccttctct ttaccatccc  18720
ttggtgcatt cgcaggccag accaccatct gcaccatctt gctgattcat ttgggtttct  18780
```

```
tatttattat ctgtgtccac tcactagagg gtaaactgca ggagggctgg ggttcgcctc  18840
taactctagt gtctacaaca cagtggctca cagttggtac ataataaata tttgctaaat  18900
gactaaccaa acaaacaaat gaatgcatat tgaaggaaat ttgaaaatgg agaatagtat  18960
aaagaaacca ataaaaacca ctcatacttc ctccttctag atattacatc tgttaatatt  19020
ttggagtatt tctttttttt cagatctttt tttctcccta ggtacatgta ggacatatat  19080
atatatatat atatattaga tatataatat ctaataggaa ataaaattat attaaattgt  19140
ggtttgtatc ctgctttttt ctctcatcat tatgttgtgt ttctacatct atggaattat  19200
cttttaaaat aatattttaa atgctgcata gattacatac atatatcaaa attataaagc  19260
atttctctaa ttctggacac tgacaatttt tttttcccta agtgatctac tttacctcca  19320
aaccattcta tttttttaaa aaagatttta tttatttgag agagagaaaa gcagagaaag  19380
catgagctgg gggagctgca gagggagagg gaaaaccagg ctccccgcta aacagggagc  19440
cctactgggg ctcaatccag gaccctagga tcgtgacttg agcagaaggc agaagcttaa  19500
ccaactgagc cacccagatg cccctctcca aactattcta gtagaacttg gcttttaagg  19560
tacttgcggt aactatttct tactttgagt agttgggtgg aagacattac tttctttcca  19620
ggaaatgtca acagatcaag cctttatttt gtatgttttc ccatcacctc cttcagtggg  19680
gattgactta gttgatgatc tagttattaa gtcaaagact tgtgtttagt acagggttgt  19740
gtttcaatga cttcctgttc gaaagataaa gtactctaag tgttcacaac tgagtagagt  19800
ccatggagaa acggaggcca ggccctgtta catctagtgc atactcttaa ctcaggggtg  19860
actgcctgtt gaaattaatc aatgcttagg gaccgaagct tcgagcgttt ccaaatactg  19920
acttataaaa tctctgtgaa ttaaaaggaa aagtaaagat aactaacacc ttcaagtgat  19980
gaaaaaggaa actgagactc aaaccgtatc tttggtgaac tagatttcag aaaagatttt  20040
acagagctgg aacggacctt cgagatgaac tgtcccgacc ttgtcatgtt ctaaagatga  20100
ggaaacagag gtccagacaa ggaagggtgt cgtacccggt caccagacca ccagcttgtg  20160
gtggggctgc aatgagaagc cacttcctct tccttggcac ccatcagtct ttccactgcc  20220
ctagctttgt ggggccttgt caccagccaa cactcagcag cagaatctgc ccttgggctc  20280
tgtttcctgg agtgctaaga aatctcctca cttcacacag aggattggaa agtcagagct  20340
ttcttttttt tttttttttt tttttttaat attttgtgat gtcgaagatc acttttttttt  20400
ttaaattttt atttatttat gatagtcaca gagagagaga gagaggcaga gacacaggca  20460
gagggagaag caggctccat gcaccgggag cccaacatag gattcgatcc cgggtctcca  20520
gaattgcgct ctgggccaaa ggcaggcgct aaaccactgc gccacccagg gatcccggaa  20580
agtcagagct ttcagggaag ccctgctgtg agtgcagcac cacaggggtg ccaggcataa  20640
aacaacacgt acaccctaac atccctttct tgtcagcccc cacccccacc ccaatccagc  20700
tctatagcac tttacgccct cagagtccca cggacctctc cttgctcgct cttgccacac  20760
tcctcttgcg gcctgtggat ggccagctct ccctctagag tagcagcttc ctgaaaccag  20820
aagctctttc tctttctttg atttttcagc gctctgtagc aaatcattgc ctagtccata  20880
atagatgttc cgtaaatatc tgctgaatac atgaataaaa acttagtttc tgaaaaaaaa  20940
aataaaaaaa aaaaacccac ttagtttctg tatcagctgg ctagggttgc ataacaaaat  21000
atgttatgag tgccttaaac aacacacact catttattca cagctgcaga ggctggaagt  21060
ccaagatcaa ggagctggca gggttggctt cctctgaagc caccctccgg ctgcctcttc  21120
```

```
acagcatcct acgctctaca cccgaacccc tgccaccatc tctatctggg tcctgatccc  21180
ctcttctcag aaggacccca gccagattgc agcagggccc accctaatgc ctcacccgaa  21240
ctcagttcca ctcttcaaac gggggggaata cagccaattt gtgaagtagt gggagttcac  21300
acttcaacat gtggatttgg ggagaaagca aaaatgttgt cccagagggc tggagagcat  21360
ggagaggctg ggaaggccaa tcacaagtca gattaggaga ggtcttattt tatagaatag  21420
taaaattggg ctttattctc tagacactga caaacttttg gttatttcag cacaaaatca  21480
tttcatccca cctcttcatt ttaccagcaa agaaaccaag gaccagagag aaaggacttg  21540
cccaaggcca tgcagtaggt caatggcaga gctgacacca gctgacactg agatctctca  21600
ggcccgggtc agagctacac tctgctaaat tcggcctgca taagtgcatc gaaaccgaca  21660
tcattttaaa gaatgaggtt ttttttttt ccccatgttt tcccatgcct ttcttttttt  21720
ttttttttt ccccccatgc ctttcatcca gttttcatcc actttctttt ttgggcaatt  21780
gtacagttcc ccaagtttca agtaattaat acctttcatc aaatataact gatatggttc  21840
agtcagaaag atccccagaa atcactaatg atgctgttcc cgtgtggctc tgtggagtgt  21900
ggccaaatgg ctcgctggta cattttacag actcgaagga cctgtatttc ttacgtctaa  21960
tagatagctc gagatagact gttacactaa acagctactc tggccaagtt tgttttacca  22020
cacatagaca cacacacacg cacatgcaca cgcacacatt tggtacacta tttcaggccg  22080
tttctgccat gcttagagct cctcatagca gtgattcccc agctagagga tgtgtgtcca  22140
accaggaaaa tggaaaccac tcagggatcc ctgggtggct cagcagttta gcaccagcct  22200
ttggcccagg gtgtgatcct ggagacccag gatcgagtcc cacgttgggc tccctgcatg  22260
gagcctgctt ctccctctgc ctgtgtctct gcctctctct ctctgtgtct ttcatgaata  22320
aataaataaa atcttaaaaa aaaaaaagaa aagaaaagaa aagaaaatgg aaaccactct  22380
aggtctttct acttaagaaa ttcaatataa agaattggat gcacaagtga tagaagagct  22440
aagaagccaa acagggatgg taaggaatca gagattaaca acagcaggag gatgctgttg  22500
ctcctgagcc tagagagaca caggagaagg tggtgacaca agatcccaga agccagggga  22560
ttatttggca agagctggag ccacagagca catgaagcca ctgccagaga tgccccttga  22620
gttagagaaa gaaaggagaa acagtcagct tgtccccacc tctcctccat tcttctgtca  22680
tacactccca tcggccaaac tgcagcatgt aggtccccat gtcaaaaagc agggcagggg  22740
aagcatgagg aaagggacag agagcaggca ccctggtggc cttgggtaaa tcatttgctc  22800
tcagttttag ttgccttgtg gataatttga taatttctca cacgtttgtt gggagaagct  22860
tcaaaggcac gtatataaat ggaagggctt ttattattgg ttttaattca aagtatttgg  22920
gactttgggc tctgggggggg acaaaagagg ggtggtgatc aggtgtcatc aggagctttg  22980
tgatgcctcc ttaattgccc tggtgaaggg aagtaggtct gcattttacc acttgttatt  23040
ttattgtgtc actctgctcc atcaggcttc aaaagccact gactgacttt gaataaactg  23100
gcacataact gaaaggatgt tggagtgtgt tctcggttct gtttggggag ctctctgtgg  23160
tttttgcatc aaaaagtgac acatagagag gactctagaa attactccaa agccattacc  23220
tccaccccac cccttttgtt ttacagagga ccagagagga gacggggttg gcctgttgtc  23280
ccatgccaaa ttcttggcag agagagatgc acggcgctgg aggagactca ctgctttctc  23340
cagtcctcct ccttgggcct tcgggtcttc agtcagcccc atataacagc tgatactgca  23400
acatttcctt gttctttgcc atgatccttc ttttccatga gcctcctctc tttctttttc  23460
gtctttaacc tcttcttcct agtagtcttt gacaactcgt tctcatgggg ttctttcgct  23520
```

```
ccactctgct gatggacatc agaagcggag tgttgagcca catctatttt aagttgagag  23580
tgtaaactct tctaaataac tccattcccc tttgatggcg ggagtgagca aggatcatca  23640
caaactcttg gaagaccagt ttttctgcca acctcagggc ttacggtgaa aataataagg  23700
tgccatctct tcctttctac tggcagaaag tacagcccat ggtcagtaag tggcaggcca  23760
ttccaaccag gcccatgaga acggtaggac ttctaccaat ggcacgaggt ggtttagccc  23820
tctcggcaag aatgggtctg tgttctgtat ctttcagtgc cagctaacct tgatgagtgg  23880
atgataaagc tcaaggatgg attccttaac ttgtcaaatg aagagattgt gccttgattg  23940
taagttccct tccagcactg acatttaaga aatcagtatc cttccaccaa agaagtccta  24000
ttatggtcac agaggcacta agattgtaat aatcccctga gtgactcatg gaattcccaa  24060
tggtccactg tgaattgaca ttttactggt gcagagtctg tggcatctta aaatgtcaga  24120
gctagaagag catcagtcat cctctaccat gaggacattg aggagtctgg gacctgaagc  24180
ttgcaagtat ccatttaccg attccttcag cagaaattga ctatgcccgt gttatgtgcc  24240
aagcagtgtt ctaggtctta gggtacagta atagagagga gtagggatct gccctcacat  24300
atgcttgtag ggtaagatgc aggacaacta gggaactaaa aaaatgggta caataattat  24360
agtttgtaat aattgtttga aaggcaataa aaatatattg gattaattca ctttgctcaa  24420
tggatattga ataacttggg tcaggggaaa gtgactgttt gtaacagtag cccttaagct  24480
gaagcgtaag aagaaaccag ctgtggaaac caggatgtaa gaaagtaggc agagagaatg  24540
acatgtgcaa aggccttggg gcaggaaagc ttttggtata gccaagatgt ggaaaggcag  24600
cgaatcaagt gggaatgtaa taggtgaaaa gtggctggag gagttggctg aaaccagatt  24660
ggctgcatag gccctcataa ggagtttagg ttttattctg agattgggaa gccattgaaa  24720
actcttaagc agttaagcaa catgttctgc ttgcatttct taaagactcc tctgattgca  24780
gaaaggagaa tggattgtag aagaggaaat gagactactg aaatagtcca gacaaaaaag  24840
aaatgataga caaaattagc agcaacggaa atggtaagaa atgggaggat ttggaataac  24900
atagaggctc taagacttgt ttcttacttg gctacataaa ctgaggatca gaggaatcaa  24960
aaaagacttc taggctgttg agcaactggg tgaatggatg tttcactaca gatgtggtaa  25020
caaacattaa aggtgggtag gattagagag atctatttac tgtaaaggga aactggggtt  25080
ccaggggaca caaggttggg gagtatacag gtatgagggt ggcataagaa ttgcaatatt  25140
agtgcctggg tggctcagtc ggttaagtgt ctaccttcag ctcaggtcat gatctcagaa  25200
tcctgagatc aagcttcaca gtgggctctg ctcagtggga agtctgcttc tccatctccc  25260
tccacccctg cccccttcct gctcatcccc tgcctcctcc ccactcatcc tctctctctt  25320
tctctctcaa ataaatgaaa gctttaaaat aaaaaaaaaa gaattgcaat attaccaaat  25380
atcatctatg ccttaagaga aagtaagact atgaatgact ttacagtggt gttattcagt  25440
gggtgtgatt tggacccatt tggcaatgtc ctgagattct tttagttgtt atgacttttg  25500
gagagattgt agtttttctg gcgtctaggg gatagaggcc agggatgctg ctagatattc  25560
ttcagtgtat aaggcagccc atataacaaa aacttgtctg gcctcacatg tcaacaatgc  25620
tgaatttgag aactctatag attatttttg gggttttata caaatgaatc atgcccagag  25680
agcaatgtct tgaaaggtgt cactccagtg ttaggaagga gtccagactg cttctgtggc  25740
aagaggctga tagtagctag tgaatatgag accagcagtt tccttgtggt ggggctggga  25800
ccccaagaga gggctctgag ccctgtaggg ccttagtaag agcagaacat tgattggatc  25860
```

-continued

```
tgaccagaga gcactaagtc cagtgggaca ccagatagat gcactgccaa gtgagagctc  25920
acttattgag caagaggacc aatggggata tgtctctggg ggaaccaggg gttgccagag  25980
gaagggaaag aggctgggag atcctaaggg gccagagggt gggtagcaag taccagttcc  26040
caaactagag atcctcaaga gtctgctggt tctcatgact gcctgcacag taaaatcacc  26100
tggggagatt ttaagagtat taatacctag gccccacccc caaagacagt tattaagttt  26160
gtctggctta gggccctaac actggaattt taaagcccct ccaggtattc tgggttaaga  26220
accactgatc taatccaagc attgcacaca gaagcttcca gaggcagaca aataaaggaa  26280
gcaagggact gggaggcccc atcgcagtgg ccagtctgta ctcagctgga gcccactatc  26340
accctgtaga gatctgggct cagtgttgcc agaaatcttc ccatttcctt gttgttgttt  26400
ttttcctctc aagaagccta aaatccagaa ttttttttt ttttttttta gtgtaagctc  26460
caaaaatctt aaaatcgcat gccaaacaaa acatgtgtgc ggagtgctct ggacctttgg  26520
gctgtcattt agcaacctct gatccagtcc agtggttttc acactttttt ttagccacag  26580
gggtttttc ctccaaacaa gctattttgt gga                                26613
```

CANNABINOID COMPOSITION AND METHODS OF TREATMENT USING THE SAME

CROSS-REFERENCE TO RELATED APPLICATIONS

This application is the National Stage of International Patent Application No. PCT/AU2019/050615, filed Jun. 14, 2019, which claims the benefit of Australian Patent Application numbers 2018902143, filed Jun. 15, 2018; and 2019901525, filed May 3, 2019, the disclosures of which are incorporated herein by reference in their entireties.

FIELD OF INVENTION

The invention relates to a composition comprising a combination of $\Delta^9$-tetrahydrocannabinol (THC) and cannabidiol (CBD). The invention also relates to methods using the composition.

BACKGROUND

The following includes information that may be useful in understanding the present invention. It is not an admission that any of the information provided herein is prior art, or relevant, to the presently described or claimed inventions, or that any publication or document that is specifically or implicitly referenced is prior art.

There has been a resurgence in popularity of therapies targeting the endocannabinoid system, both due to increased scientific support for the efficacy of these treatments and relaxation of regulation of Cannabis products in some jurisdictions. This resurgence is also evidenced by the regulatory approval of some Cannabis-derived therapeutic compositions for a limited range of indications. The endocannabinoid system is highly conserved across many animal species, including mammals, such as companion animals. This system includes the cannabinoid receptors CB1, CB2, and GPR55, as well as the transient receptor potential ion channel TRPV1. The expression pattern for each of these proteins is different; however, the endocannabinoid system is expressed widely throughout the body, including in the central nervous system (CNS), the peripheral nervous system (PNS), gastrointestinal tract (GIT), immune and endocrine tissues, reproductive organs, and in the skeleton and/or tissues associated with skeletal functions.

Currently, medicinal cannabis is popular among human patients and prescribers alike due to the reported benefits of cannabinoids, the active components of the cannabis plant, and the long history of use which provides a known safety profile. This popularity has led many companies to develop formulations of cannabinoids for human patients. However, there may be significant interspecies differences in terms of formulation requirements.

Accordingly, there is a continuing need to develop cannabinoid-based treatment options that are suitable for administration to non-human subjects, preferably in addition to humans. There is also an ongoing need for alternative therapies for the treatment of pain, inflammation and/or anxiety.

SUMMARY

In one aspect, the invention provides a liquid composition comprising a combination of $\Delta_9$-tetrahydrocannabinol (THC) and cannabidiol (CBD) and an oral delivery system.

In some embodiments, the ratio by weight of THC:CBD is 1:1.2 or more.

In some embodiments, the ratio by weight of THC:CBD is 1 or more: 1.

In a further aspect, the invention provides a food product comprising the liquid composition of the invention.

In another aspect, the invention provides a method of treating pain, inflammation and/or anxiety, comprising orally administering to a subject in need thereof an effective amount of the liquid composition of the invention or the food product of the invention.

In a further aspect, the invention provides use of a liquid composition of the invention or the food product of the invention in the manufacture of a medicament for treating pain, inflammation and/or anxiety.

In another aspect, the invention provides a method of controlling a heart rate of a subject, comprising orally administering to the subject an effective amount of the liquid composition of the invention or the food product of the invention.

In a further aspect, the invention provides use of the liquid composition of the invention or the food product of the invention in the manufacture of a medicament for controlling a heart rate of a subject.

In another aspect, the invention provides a method of downregulating expression of chemokine (C-C motif) ligand 5 gene (CCL5, as shown in SEQ ID NO:4) and/or downregulating expression of cerebellar degeneration-related protein 2 gene (CDR2, as shown in SEQ ID NO:2) and/or upregulating expression of cannabinoid Receptor 2 gene (CNR2, as shown in SEQ ID NO:3) and/or upregulating expression of interleukin 8 gene (CXCL8, as shown in SEQ ID NO:1) and/or upregulating expression of adrenoreceptor beta 2 gene (ADRB2, as shown in SEQ ID NO:5), comprising contacting a cell with a combination of THC and CBD, wherein the ratio by weight of THC:CBD is 1 or more: 1.

In a further aspect, the invention provides a method of downregulating expression of interleukin 8 gene (CXCL8, as shown in SEQ ID NO:1) and/or upregulating expression of chemokine (C-C motif) ligand 5 gene (CCL5, as shown in SEQ ID NO:4) and/or upregulating expression of cannabinoid Receptor 2 gene (CNR2, as shown in SEQ ID NO:3) and/or upregulating expression of adrenoreceptor beta 2 gene (ADRB2, as shown in SEQ ID NO:5), comprising contacting a cell with a combination of THC and CBD, wherein the ratio by weight of THC:CBD is 1:1.2 or more. In another aspect, the invention provides a method of affecting the concentration of a biomarker associated with inflammation selected from granulocyte-macrophage colony-stimulating factor (GM-CSF) and interleukin-15 (IL-15) or a combination thereof, comprising contacting a cell with a combination of THC and CBD.

In a further aspect, the invention provides a kit comprising in separate parts:

(a) $\Delta^9$-tetrahydrocannabinol (THC) and an oral delivery system; and (b) cannabidiol (CBD) and an oral delivery system.

BRIEF DESCRIPTION OF THE ACCOMPANYING DRAWINGS

The invention may be further described with reference to the following non-limiting drawings, in which.

Figure 25:
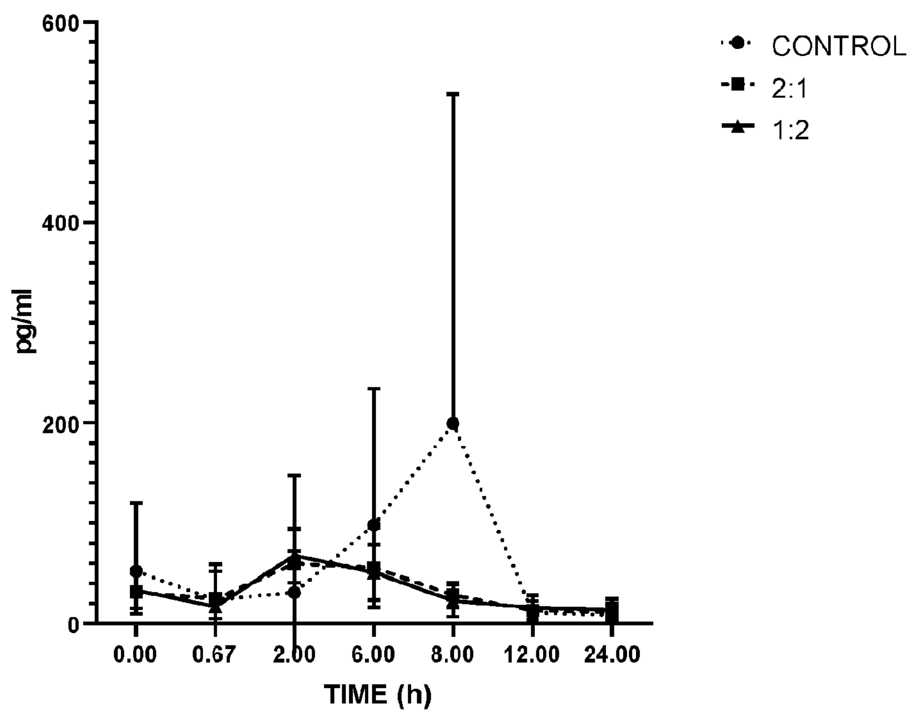
Figure 26:
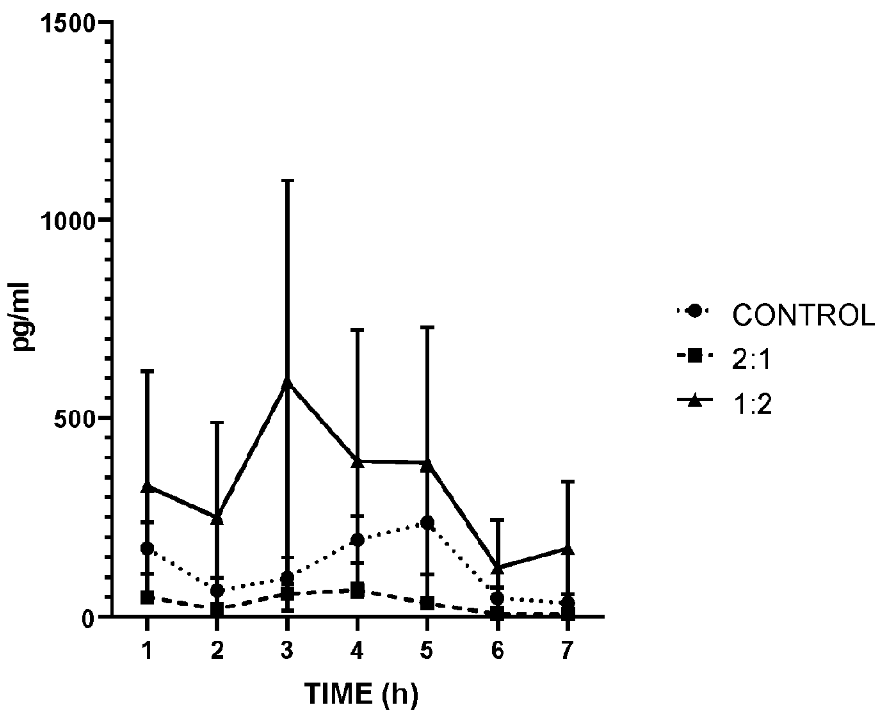

FIG. 25 shows a chart of the concentration of granulocyte-macrophage colony-stimulating factor (GM-CSF) in blood over 24 hours following administration of (i) MCT oil; (ii) a composition of the invention comprising a 2:1 ratio by weight of THC:CBD and MCT oil; and (iii) a composition of the invention comprising a 1:2 ratio by weight of THC:CBD and MCT oil; and FIG. 26 shows a chart of the concentration of interleukin 15 (IL-15) in blood over 24 hours following administration of (i) MCT oil; (ii) a composition of the invention comprising a 2:1 ratio by weight of THC:CBD and MCT oil; and (iii) a composition of the invention comprising a 1:2 ratio by weight of THC:CBD and MCT oil.

DEFINITIONS

Before describing the present invention in detail, it is to be understood that this invention is not limited to particularly exemplified embodiments, such as the compositions, methods and uses, which may, of course, vary. It is also to be understood that the terminology used herein is for the purpose of describing particular embodiments of the invention only and is not intended to be limiting.

All publications, patents and patent applications that may be cited herein are hereby incorporated by reference in their entirety.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "administering" refers to providing the composition to a subject suffering from or at risk of the disorders(s) and/or condition(s) to be treated.

By "effective amount" it is meant an amount sufficient that, when administered to a subject, an amount of the composition is provided to achieve an effect. In the case of a therapeutic method, this effect may be the treatment of a pain, inflammation and/or anxiety, or to control a heart rate of a subject. Therefore, the "effective amount" may be a "therapeutically effective amount". By "therapeutically effective amount" it is meant an amount sufficient that when administered to a subject an amount of composition is provided to treat the disease, disorder and/or condition, or a symptom of the disease, disorder and/or condition.

As used herein, the terms "treating", "treatment", "treat" and the like mean affecting a subject (e.g. a patient), tissue or cell to obtain a desired pharmacological and/or physiological effect. The effect may be prophylactic in terms of completely or partially preventing, or reducing the severity of, a disease or associated symptom, and/or may be therapeutic in terms of a partial or complete cure of a disease. For example, a reference to "treating" inflammation may therefore encompass: (a) arresting the progress of the disease, e.g. preventing worsening of a symptom or complication over time; (b) relieving or ameliorating the effects of inflammation, i.e. causing an improvement of at least one symptom or complication of inflammation; (c) preventing additional symptoms or complications of inflammation from developing; and/or (d) preventing inflammation or a symptom associated with inflammation from occurring in a subject. In another example, a reference to "treating" pain may therefore encompass: (a) preventing the severity of the pain from increasing; (b) relieving or ameliorating the severity of pain as experienced by the subject; (c) preventing the spread of pain from its originating location; and/or (d) preventing or delaying the onset of pain in the subject. In a further example, a reference to "treating" anxiety may therefore encompass: (a) preventing the severity of the anxiety from increasing, for example by preventing increase of a subject's heart rate; (b) relieving or ameliorating the severity of the anxiety as experienced by the subject in the short and/or long term, for example by lowering a heart rate of a subject; (c) preventing additional symptoms associated with anxiety from developing; and/or (d) preventing or delaying the onset of anxiety in the subject.

It must be noted that as used herein and in the appended claims, the singular forms "a," "an," and "the" include plural reference unless the context clearly dictates otherwise. Thus, for example, a reference to "a fatty acid" and/or "at least one fatty acid" may include one or more fatty acids, and so forth.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The term "(s)" following a noun contemplates the singular or plural form, or both.

The term "and/or" can mean "and" or "or".

Unless the context requires otherwise, all percentages referred to herein are percentages by weight of the composition.

Unless the context requires otherwise, all amounts referred to herein are intended to be amounts by weight.

Various features of the invention are described with reference to a certain value, or range of values. These values are intended to relate to the results of the various appropriate measurement techniques, and therefore should be interpreted as including a margin of error inherent in any particular measurement technique. Some of the values referred to herein are denoted by the term "about" to at least in part account for this variability. The term "about", when used to describe a value, may mean an amount within ±25%, ±10%, ±5%, ±1% or ±0.1% of that value.

The term "comprising" is used in an inclusive sense, i.e. to specify the presence of the stated features but not to preclude the presence or addition of further features in various embodiments of the invention. When interpreting statements in this specification that include that term, the features, prefaced by that term in each statement, all need to be present but other features can also be present. Related terms such as "comprise" and "comprised" are to be interpreted in the same manner.

The term "pharmaceutically acceptable" in the context of a form of a compound or an additive to the composition, is intended to mean that the form of the compound or the additive to the composition is suitable for use in a pharmaceutical sense. Therefore, pharmaceutically acceptable forms and/or additives are non-toxic to the subject in the amounts in which they are present in the compositions described herein. In some embodiments, the composition of the invention is a nutraceutical composition. It will be appreciated that any ingredient that is pharmaceutically acceptable will also be suitable for nutraceutical use.

The term "veterinary acceptable" in the context of a form of a compound or an additive to the composition, is intended to mean that the form of the compound or the additive to the composition is suitable for use in a veterinary sense. Therefore, veterinary acceptable forms and/or additives are non-toxic to the non-human subject in the amounts in which they are present in the composition described herein.

The term "nutraceutically acceptable" in the context of a form of a compound or an additive to the composition, is intended to mean that the form of the compound of the additive to the composition is suitable for use in a nutraceutical sense. Therefore, nutraceutically acceptable forms and/or additives are non-toxic to the subject in the amounts in which they are present in the composition described herein. It will be appreciated that all pharmaceutically acceptable forms and additives will typically also be nutraceutically acceptable.

The term "cannabinoid" as used herein relates to any compound that has activity involving the endocannabinoid system.

The term "phytocannabinoid" refers to a cannabinoid that has been reported in an extract of a Cannabis plant, whether derived from a Cannabis plant or synthetically created.

The term "cannabinoid fraction" is used to describe the combination of cannabinoids present in the Cannabis extract.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DESCRIPTION OF EMBODIMENT(S)

The invention provides a liquid composition comprising a combination of $\Delta^9$-tetrahydrocannabinol (THC) and cannabidiol (CBD) and an oral delivery system.

The inventors have surprisingly found that oral administration of the liquid composition of the invention to a subject does not result in any significant observed adverse events while achieving sufficient bioavailability of both cannabinoids to provide a biological response in the subject.

THC is the main psychotropic constituent of Cannabis, its main pharmacological effects including analgesia, muscle relaxation, antiemesis, appetite stimulation and psychoactivity. THC is a partial agonist of both the CB1 and CB2 receptors. THCs activity at the CB1 receptor are primarily implicated in its psychotropic effects. CB1 receptors are primarily expressed in the central nervous system, including within the brain, while CB2 receptors are typically expressed throughout the body, including in the peripheral nervous system. Further, due to its well-documented psychotropic efficacy, it is known that THC can cross the blood brain barrier when administered in a variety of forms, including inhalation and oral dosing.

Most of the recent data regarding the activity of THC focusses on the human endocannabinoid system. However, prior to the present invention it was commonly assumed that ingestion of THC by a companion animal, such as a dog or a cat, results in THC toxicity which includes symptoms of:

panting (in dogs), anxiety, and extreme agitation
dilated pupils, glossy-eyes, and a "dazed and confused" appearance
extreme lethargy
staggering, stumbling, and being unable to walk without falling or losing their balance
drooling and vomiting
diarrhea (especially if a pet has consumed high-fat edibles, cannabutter, or oils)
inability to control their bladders
abnormal heart rate and blood pressure.

CBD is the main non-psychotropic cannabinoid present in extracts of the Cannabis sativa plant, in some cases constituting up to 40 percent of its extract depending on plant genetics and the extraction technique employed. Both animal and human studies suggest that the pharmacokinetics and pharmacodynamics of CBD are very complex. CBD appears to operate at both CB1 and CB2 endocannabinoid receptors within the endocannabinoid system (ECS) indirectly stimulating endogenous cannabinoid signalling (anandamide) by suppressing fatty acid amide hydrolase (FAAH), the enzyme that breaks down anandamide. Importantly, this enables more anandamide to remain at the receptors, which elicits anxiolytic and antidepressant like effects. This indirect agonist property at the cannabinoid receptors may also explain its promising safety profile. Furthermore, CBD has been shown to also act on the vanilloid, adenosine and serotonin receptors explaining its broad spectrum of potential therapeutic properties in animal models and humans, including anxiolytic, antidepressant, neuroprotective, anti-inflammatory and immunomodulatory actions.

It is believed that THC and CBD used in combination act synergistically in the treatment of some indications, such as to maximize biological response. CBD has been demonstrated to antagonise some undesirable effects of THC including intoxication, sedation and tachycardia, while contributing analgesic, anti-emetic, and anti-carcinogenic properties. The liquid compositions of the invention therefore comprise the combination of THC and CBD to exploit the beneficial cooperation of these two active cannabinoids.

The composition of the invention is in a liquid form. Liquid form compositions may be preferred as the amount administered may be more readily adjusted depending on requirements for a subject compared to other dosage forms, such as tablets. In addition, liquid form compositions may also be preferred for oral dosing to subjects that may not be able to swallow solid compositions, such as non-human subjects. Accordingly, the liquid composition may be a pharmaceutical composition, a veterinary composition and/ or a nutraceutical composition. The liquid composition is typically a solution and/or a suspension of the cannabinoids in an oral delivery system.

It was also surprisingly found that administering the liquid composition of the invention affected the gene expression profile (Example 4) and inflammatory biomarker concentrations (Example 5) for the subjects. Further, the expression of genes surprisingly differed depending on the ratio of THC:CBD contained in the composition (see FIGS. 20-26).

Accordingly, in some embodiments, the liquid composition comprises a higher amount as a proportion by weight of THC relative to CBD. Such liquid compositions may be referred to herein as "high-THC compositions". The ratio by weight of THC:CBD in these embodiments may be greater than 1:1. For example, in some embodiments the ratio by weight of THC:CBD may be about 1.01:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.5:1, 4:1, 4.5:1, 5:1, 6:1, 7:1, 8:1, 9:1, 10:1, 20:1, 30:1, 40:1, 50:1, 60:1, 70:1, 80:1, 90:1, 95:1, 99:1 or higher. The ratio by weight of THC:CBD may be from any of these ratios to any other of these ratios without limitation. For example, the ratio by weight of THC:CBD may be from about 1.01:1 to about 99:1, about 1.01:1 to about 10:1 or about 1.1:1 to about 3:1.

Surprisingly, administration of a high-THC composition showed downregulation of CDR2 at 72 h after treatment and upregulation of CXCL8 at 1.5 h and 72 h after administration, which differed significantly from results obtained after administration of a vehicle (control) or compositions comprising a lower ratio of THC relative to CBD.

In other embodiments, the liquid composition comprises a lower amount as a proportion by weight of THC relative to CBD. Put another way, the liquid composition comprises a higher amount as a proportion by weight of CBD relative to THC in these embodiments. Such liquid compositions may be referred to herein as "high-CBD compositions". In these embodiments, the ratio by weight of THC:CBD may be 1:1.2 or higher. For example, in some embodiments, the ratio by weight of THC:CBD may be about 1:1.2, 1:1.21, 1:1.25, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.5, 1:4, 1:4.5, 1:5, 1:6, 1:7, 1:8, 1:9, 1:10, 1:20, 1:30, 1:40, 1:50, 1:60, 1:70, 1:80, 1:90, 1:95, 1:99 or lower. The ratio by weight of THC:CBD may be from any of these ratios to any other of these ratios without limitation. For example, the ratio by weight of THC:CBD may be from 1:1.2 to about 1:99, about 1:1.3 to about 1:10 or about 1:1.4 to about 1:5.

Surprisingly, administration of liquid compositions comprising a higher ratio of CBD relative to THC showed upregulation of CCL5 at 1.5 h and 72 h after treatment, downregulation of CDR2 at 1.5 h after treatment, upregulation of CNR2 at 1.5 h after treatment at a level greater than following administration of a 2:1 THC:CBD composition, downregulation of CXCL8 at 1.5 h and 72 h after administration and greater than 3-fold upregulation of ADRB2. In addition, it was surprising that the concentrations for inflammatory biomarkers GM-CSF and IL-15 were elevated for the high-CBD compositions as compared to administration of the control and high-THC compositions.

It is believed that THC and CBD are artefacts of isolation and extraction from the Cannabis plant, where their natural biosynthesised precursors are $\Delta^9$-tetrahydrocannabinolic acid (THCA) and cannabidiolic acid (CBDA), respectively. Analytically it is also difficult to detect the precise concentration of THCA and CBDA due to their propensity to decompose into decarboxylated THC and decarboxylated CBD. In some embodiments, the liquid compositions comprising a non-natural amount of decarboxylated THC and decarboxylated CBD. In some embodiments, the liquid compositions comprise less than about 0.5 mg/ml THCA and/or CBDA.

In general, when cannabinoids are accessed from Cannabis extraction, the concentration of THC and THCA, and similarly the concentration of CBD and CBDA, are reported together due to the difficulty in preventing decarboxylation under analytical conditions, e.g. conditions associated with gas chromatography (GC), high-performance liquid chromatography (HPLC) or ultra-high-performance liquid chromatography (UPLC) techniques. Unless the context requires otherwise, any amount of THC referred to herein may be read as referring to the combined amount of THC and THCA. Unless the context requires otherwise, any amount of CBD referred to herein may be read as referring to the combined amount of CBD and CBDA. Further, unless the context requires otherwise, the relative amounts of THC:CBD described above may in some embodiments refer to the combined amount of THC and THCA relative to the combined amount of CBD and CBDA. In some embodiments, the liquid compositions may comprise the combination of THC, THCA, CBD and CBDA. The structures of THC, THCA, CBD and CBDA are shown in Table 1 below.

TABLE 1

| # Cannabinoid | Structure |
| --- | --- |
| 1 $\Delta^9$-Tetrahydrocannabinol (THC) | $H_3C$, HO, H, $C_5H_{11}$, H, O, $H_3C$, $CH_3$ |
| 2 $\Delta^9$-Tetrahydrocannabinolic acid (THCA) | HO, $H_3C$, HO, O, H, $C_5H_{11}$, H, O, $H_3C$, $CH_3$ |
| 3 Cannabidiol (CBD) | $H_3C$, HO, $C_5H_{11}$, HO, $H_2C$, $CH_3$ |
| 4 Cannabidiolic acid (CBDA) | HO, $H_3C$, HO, O, $C_5H_{11}$, HO, $H_2C$, $CH_3$ |

The composition may comprise any effective amount of THC. In some embodiments, the minimum amount of THC may be at least about 0.01%, 0.05%, 0.1%, 0.2%, 0.3%, 0.4% or 0.5%. In some embodiments, the maximum amount of THC may be not more than about 10%, 9%, 8%, 7%, 6%, 5%, 4%, 3%, 2%, 1%, 0.9%, 0.8%, 0.7% or 0.6%. The composition may comprise THC in an amount from any of these minimum amounts to any of these maximum amounts, for example, from about 0.01% to about 10% or about 0.1% to about 1%.

The composition may comprise any effective amount of CBD. In some embodiments, the minimum amount of CBD may be at least about 0.01%, 0.05%, 0.1%, 0.2%, 0.3%, 0.4% or 0.5%. In some embodiments, the maximum amount of CBD may be not more than about 10%, 9%, 8%, 7%, 6%, 5%, 4%, 3%, 2%, 1%, 0.9%, 0.8%, 0.7% or 0.6%. The composition may comprise CBD in an amount from any of these minimum amounts to any of these maximum amounts, for example, from about 0.01% to about 10% or about 0.1% to about 1%.

The THC and CBD present in the composition may be provided from a natural or a synthetic source, or a combination sources, including semi-synthetic sources. Cannabinoids provided from natural sources may be isolated, purified and then combined. Alternatively, an extract of a Cannabis plant (e.g. an extract that has been enriched in one or more of THC, THCA, CBD and CBDA) may be used to provide the cannabinoids. Synthetic or semi-synthetic or isolated natural THC, THCA, CBD and/or CBDA may be added to a Cannabis extract to enrich the extract in any of these cannabinoids. These mixtures may be prepared by any means known in the art.

In some embodiments, in addition to the combination of THC and CBD, the liquid compositions comprise one or more additional cannabinoids. The one or more additional cannabinoids may be selected from cannabigerol (CBG), cannabigerolic acid (CBGA), cannabinol (CBN) and cannabichromene (CBC). In other embodiments, the amount of any of these additional cannabinoids may be not more than about 1%, 0.7% or 0.5%, or the composition may be free of any or all of these additional cannabinoids.

In some embodiments, the combination of THC and CBD is provided in the form of a Cannabis extract.

To date, over 100 cannabinoids have been identified in Cannabis extracts. A comprehensive list of these cannabinoids may be found in Mahmoud A. El Sohly and Waseem Gul, "Constituents of Cannabis sativa" In Handbook of Cannabis Roger Pertwee (Ed.) Oxford University Press (2014) (ISBN: 9780199662685). Cannabinoids that have been identified in Cannabis plants include: Cannabigerol (E)-CBG-C5, Cannabigerol monomethyl ether (E)-CBGM-C5 A, Cannabigerolic acid A (Z)-CBGA-C5 A, Cannabigerovarin (E)-CBGV-C3, Cannabigerolic acid A (E)-CBGA-C5 A, Cannabigerolic acid A monomethyl ether (E)CBGAM-C5 A and Cannabigerovarinic acid A (E)-CBGVA-C3 A; (±)-Cannabichromene CBC-C5, (±)-Cannabichromenic acid A CBCA-C5 A, (±)-Cannabivarichromene, (±)-Cannabichromevarin CBCV-C3, (±)-Cannabichromevarinic acid A CBCVA-C3 A; (−)-Cannabidiol CBD-C5, Cannabidiol monomethyl ether CBDMC, Cannabidiol-C4 CBD-C4, (−)-Cannabidivarin CBDV-C3, Cannabidiorcol CBD-CI, Cannabidiolic acid CBDA-C5, Cannabidivarinic acid CBDVA-C3; Cannabinodiol CBND-C5, Cannabinodivarin CBND-C3; Δ9-Tetrahydrocannabinol Δ9-THC-C5, Δ9-Tetrahydrocannabinol-C4 Δ9-THC-C4, Δ9-Tetrahydrocannabivarin Δ9-THCV-C3, Δ9-Tetrahydrocannabiorcol Δ9-THCO-CI, Δ9-Tetrahydrocannabinolic acid A Δ9-THCA-C5 A, Δ9-Tetrahydrocannabinolic acid B Δ9-THCA-C5 B, Δ9-Tetrahydrocannabinolic acid-C4 A and/or B Δ9-THCA-C4 A and/or B, Δ9-Tetrahydro-cannabivarinic acid A Δ9-THCVA-C3 A, Δ9-Tetrahydrocannabiorcolic acid A and/or B Δ9-THCOA-CI A and/or B, (−)-Δ8-trans-(6aR,10aR)-Δ8-Tetrahydrocannabinol Δ8-THC-C5, (−)-Δ8-trans-(6aR,10aR)-Tetrahydrocannabinolic acid A Δ8-THCA-C5 A, (−)-(6aS,10aR)-Δ9-Tetrahydrocannabinol (−)-cis-Δ9-THC-C5; Cannabinol CBN-C5, Cannabinol-C4 CBN-C4, Cannabivarin CBN-C3, Cannabinol C2 CBN-C2, Cannabiorcol CBN-CI, Cannabinolic acid A CBNA-C5 A, Cannabinol methyl ether CBNM-C5, (−)-(9R,10R)-trans-Cannabitriol (−)-trans-CBT-C5, (+)-(9S,10S)-Cannabitriol (+)-trans-CBT-C5, (±)-(9R,10S/9S,10R)-Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3 (±)-trans-CBT-C3, 8,9-Dihydroxy-Δ6a(10a)-tetrahydrocannabinol 8,9-Di-OH-CBT-C5, Cannabidiolic acid A cannabitriol ester CBDA-C5 9-OH-CBT-C5 ester, (−)-(6aR,9S,10S,10aR)-9,10-Dihydroxy-hexahydrocannabinol, Cannabiripsol, Cannabiripsol-C5, (−)-6a,7,10a-Trihydroxy-Δ9-tetrahydrocannabinol (−)-Cannabitetrol, 10-Oxo-Δ6a(10a)tetrahydrocannabinol (OTHC); (5aS,6S,9R,9aR)-Cannabielsoin CBE-C5, (5aS,6S,9R,9aR)-C3-Cannabielsoin CBE-C3, (5aS,6S,9R,9aR)-Cannabielsoic acid A CBEA-C5 A, (5aS,6S,9R,9aR)-Cannabielsoic acid B CBEA-C5 B; (5aS,6S,9R,9aR)-C3-Cannabielsoic acid B CBEA-C3 B, Cannabiglendol-C3 OH-iso-HHCV-C3, Dehydrocannabifuran DCBF-C5, Cannabifuran CBF-C5, (−)-Δ7-trans-(1R,3R,6R)-Isotetrahydrocannabinol, (±)-Δ7-1,2-cis-(1R,3R,6S/1S,3S,6R)-Isotetrahydrocannabivarin, (−)-Δ7-trans-(1R,3R,6R)-Isotetrahydrocannabivarin; (±)-(IaS,3aR,8bR,8cR)-Cannabicyclol CBL-C5, (±)-(1aS,3aR,8bR,8cR)-Cannabicyclolic acid A CBLA-C5 A, (±)-(IaS,3aR,8bR,8cR)-Cannabicyclovarin CBLV-C3; Cannabicitran CBT-C5; Cannabichromanone CBCN-C5, CannabichromanoneC3 CBCN-C3, and Cannabicoumaronone CBCON-C5.

The sum of the weights of any cannabinoids present in a Cannabis extract may be referred to herein as a cannabinoid fraction. The cannabinoid fraction typically accounts for the majority of the compounds present in the Cannabis extract. In some embodiments, the Cannabis extract comprises a cannabinoid fraction in a maximum amount of up to about 97%, 96%, 95%, 94%, 90%, 80%, 70% or 60%. The minimum amount of cannabinoid fraction may be at least about 15%, 20%, 30%, 40% or 50%. The Cannabis extract may comprise the cannabinoid fraction from any of these minimum amounts to any of these maximum amounts, for example, from about 15% to about 97% or about 50% to about 94%.

In addition to a cannabinoid fraction, Cannabis extracts may also comprise a diverse array of secondary metabolites, including terpenes and terpenoids, sterols such as phytosterols, triglycerides, alkanes, squalenes, tocopherols, carotenoids, flavonoids, polyphenols, cannflavins and alkaloids. The mix of these secondary metabolites varies depending on several factors, including Cannabis variety, part of the Cannabis plant extracted, method of extraction, processing of the extract, and season. In some embodiments, the Cannabis extract may comprise the non-cannabinoid fraction in a maximum amount of up to about 20%, 15%, 10%, 6% or 5%. The Cannabis extract may comprise the non-cannabinoid fraction in a minimum amount of at least about 0.001%, 0.005%, 0.01%, 0.05%, 0.1%, 0.5%, 1% or 3%. The Cannabis extract may comprise the non-cannabinoid fraction in an amount from any of these minimum amounts to any of these maximum amounts, for example, from about 0.001% to about 20% or about 0.1% to about 6%.

There are several varieties of Cannabis plant, which have been described under two distinct naming conventions. One of these conventions identifies three distinct species of Cannabis plant, namely Cannabis sativa Linnaeus, Cannabis indica LAM., and Cannabis ruderalis. Another convention identifies all Cannabis plants as belonging to the Cannabis sativa L. species, with the various varieties divided amongst several subspecies, including: Cannabis sativa ssp. sativa and ssp. indica. As used herein, the term "Cannabis" refers to any and all of these plant varieties.

The Cannabis extract may be prepared by any means known in the art. The extracts may be formed from any part of the Cannabis plant. Extracts may be formed by contacting an extractant with a leaf, seed, trichome, flower, kief, shake, bud, stem or a combination thereof. Any suitable extractant known in the art may be used, including, for example, alcohols (e.g. methanol, ethanol, propanol, butanol, propylene glycol, etc.), water, hydrocarbons (e.g. butane, hexane, etc.), oils (e.g. olive oil, vegetable oil, etc.), a polar organic solvent (e.g. ethyl acetate, polyethylene glycol, etc.) or a supercritical fluid (e.g. liquid $CO_2$). The extractant may be completely or partially removed prior to incorporation of the Cannabis extract into the composition, or it may be included in the composition, and in some embodiments may form part of the oral delivery system. The extractant may be removed by heating the extract optionally under reduced pressure (e.g. under vacuum). It will be appreciated that some of the more volatile plant metabolites (such as terpenes) may also be removed with the extractant and some cannabinoids may decompose under heating, such as decarboxylation of a cannabinoid acid (e.g. THCA or CBDA). In some embodiments, removing the extractant may enrich the cannabinoid fraction of the extract. In some embodiments, the extract is filtered to remove particulate material, for example, by passing the extract through filter paper or a fine sieve (e.g. a sieve with pore sizes of 5 μm).

In some embodiments, the Cannabis extract is formed by applying heat and pressure to the plant material. Typically, in these embodiments, no extractant is required.

Oral Delivery System

The liquid composition comprises an oral delivery system. The oral delivery system comprises one or more pharmaceutically, veterinary and/or nutraceutically acceptable carriers to solubilise or suspend the THC and CBD in a manner that enables it to be administered orally to a subject.

The composition may comprise the oral delivery system in a major amount. In some embodiments, the composition comprises a minimum concentration of oral delivery system of at least about 40%, 45%, 50%, 55%, 60%, 65%, 70%, 75%, 80%, 85%, 90%, 91%, 92%, 93%, 94%, 95% or 96%. The composition may comprise a maximum concentration of oral delivery system of up to about 99.99%, 99.9%, 99.5%, 99%, 98.5, 98%, 97.5%, 97% or 96.5%. The concentration of fatty acid component in the composition may be from any of these minimum values to any of these maximum values, for example from about 40% to about 99.99% or about 75% to about 98%.

The oral delivery system preferably comprises all liquid ingredient(s). In some embodiments, the oral delivery system comprises a liquid ingredient selected from ethanol, glycerine, propylene glycol, a fatty acid (optionally in the form of an oil), an emulsifier, and water or a combination thereof. Suitable emulsifiers include cationic, anionic, zwitterionic and non-ionic surfactants. In some embodiments, the emulsifier may be selected from the following group: a sulfate ester, a sulfonate ester, a phosphate ester, an alkyl carboxylate, lecithin, a quaternary ammonium salt, a polyethylene glycol (PEG), an alkylated fatty acid and/or fatty acid ester, a fatty acid ester of a polyol (such as sorbitan monolaurate, sorbitan monostearate and sorbitan tristearate), an alkylpolyglucoside, an ethoxylated amine, an ethoxylated fatty acid amide, a poloxamer, a polysorbate (e.g. polysorbate 20, 40, 60 or 80 or tween 20, 40, 60 or 80), a pegylated oil (e.g. polyoxyl 35 castor oil), and a combination thereof.

As THC and CBD are both lipid soluble, in some embodiments, the oral delivery system comprises a fatty acid. The fatty acid may be in the form of a free acid or an ester, such as a glyceride. It will therefore be understood that a reference to a "fatty acid" includes the free fatty acid and an ester thereof. Fatty acid esters include glyceryl esters, such as monoglycerides, diglycerides and triglycerides. The fatty acid residues included in a diglyceride and/or triglyceride may be the same or different and may be selected from any of the fatty acids described herein.

The fatty acid may be selected from saturated and unsaturated fatty acids or a combination thereof.

Unsaturated fatty acids may comprise from 1 to n/2 double carbon-carbon bonds, wherein n is the number of carbon atoms in the fatty acid side chain. Typically, unsaturated fatty acids comprise from 1 to 10 double carbon-carbon bonds. The double carbon-carbon bonds may be cis or trans. Typically, the double carbon-carbon bonds are cis.

The fatty acid may be:

- a short chain fatty acid (SCFA) comprising from 2 to 6 carbon atoms (inclusive of the carboxyl carbon);
- a medium-chain fatty acid (MCFA) comprising from 7 to 13 carbon atoms (inclusive of the carboxyl carbon);
- a long-chain fatty acid (LCFA) comprising from 14 to 22 carbon atoms (inclusive of the carboxyl carbon); and/or
- a very long chain fatty acid (VLCFA) comprising 23 or more carbon atoms (inclusive of the carboxyl carbon), for example from 23 to 100 carbon atoms.

In some embodiments, the fatty acid component comprises a MCFA, a LCFA or a combination thereof.

In some embodiments, the fatty acid component comprises a fatty acid selected from one or more of the group consisting of butyric acid (4:0); caproic acid (6:0); caprylic acid (8:0); capric acid (10:0); undecanoic acid (11:0); lauric acid (12:0); tridecanoic acid (13:0); myristic acid (14:0); myristoleic acid (14:1); pentadecanoic acid (15:0); cis-10-pentadecanoic acid; cis-10-pentadecenoic acid; palmitic acid (16:0); palmitoleic acid (16:1n-9); hexadecenoic acid (16:1); hexadecadienoic acid (16:2); margic/heptadecanoic acid (17:0); cis-10-heptadecanoic acid; cis-10-heptadecenoic acid; margaroleic acid (17:1); stearic acid (18:0); vaccenic acid (18:1); oleic acid (18:1); elaidic acid (18:1); linoleic acid (LA; 18:2); linolelaidic acid (18:2n-6); linolenic acid (18:3) including α-linolenic acid (ALA) and γ-linolenic acid (GLA); octadecatrienoic acid (18:3); stearidonic acid (SDA; 18:4n-3); arachidic acid (20:0); eicosenoic acid (20:1) including gadoleic acid (20:1n-11), gondoic acid (20:1n-9) and paullinic acid (20:1n-7); eicosadienoic acid (20:1n-6); cis-11, 14, 17-eicosatrienoic acid; cis-8, 11, 14-eicosatrienoic acid; eicosatetraenoic acid; arachidic acid (AA; 20:0); eicosapentaenoic acid (20:5n-3); heneicosanoic acid (21:0); behenic acid (22:0); cetoleic/erucic acid (22:1n-9); dicosadienoic acid (22:2n-6); docosapentanoic/docosapentaenoic acid (DPA; 22:5); docosahexaenoic acid (DHA; 22:6n-3); tricosanoic acid (23:0); lignoceric acid (24:0); and nervonic acid (24:1n-9).

The fatty acid component may comprise fatty acids derived from nature or produced synthetically (i.e. non-natural). In some embodiments, the liquid composition comprises at least one fatty acid from a non-natural source.

In some embodiments, the fatty acid is provided in the form of an edible oil. In some embodiments, the edible oil is selected from flax seed oil, hemp seed oil, fish oil, coconut oil, cocoa butter, palm kernel oil, palm oil, cottonseed oil, wheat germ oil, soybean oil, olive oil, corn oil, sunflower oil, safflower oil, canola oil, sesame oil, peanut oil, rosemary oil, anise oil, or a combination thereof. In some embodiments, the fatty acid component comprises a combination of 2, 3, 4 or more oils, such as any of the oils described herein.

Triglycerides comprising at least 1 MCFA may be referred to herein as a medium chain triglyceride (MCT). In some embodiments, the oral delivery system comprises a MCT. In these embodiments, the MCT may be provided in the form of an oil comprising an MCFA, herein referred to as an MCT oil. MCT oils are advantageously associated with a range of health benefits when administered to a subject, including when administered in the composition of the invention.

In some embodiments, wherein the oral delivery system comprises a fatty acid, the composition may further comprise an antioxidant to delay or prevent oxidation of the fatty acid. Any compatible antioxidant may be included. The antioxidant may be selected from ascorbic acid, butylated hydroxyanisole, butylated hydroxytoluene (BHT), propyl gallate, a tocopherol and a pentacyclic triterpenic acid (such as those described in Australian Provisional Patent Application No. 2019901093) or a combination thereof.

The composition may comprise the antioxidant in a stabilising amount. A stabilising amount is an amount effective to delay oxidation of the fatty acid component.

In some embodiments, the minimum concentration of antioxidant may be at least about 0.0001%, 0.0005%, 0.001%, 0.005%, 0.01%, 0.05% or 0.1%. In some embodiments, the maximum concentration of antioxidant may be not more than about 20%, 15%, 10%, 9%, 8%, 7%, 6% or 5%. The composition may comprise the antioxidant in a concentration from any of these minimum concentrations to any of these maximum concentrations, for example, from about 0.0001% to about 20% or from about 0.05% to about 6%.

In some embodiments, the composition may comprise a further active pharmaceutical, veterinary and/or nutraceutical ingredient other than THC and CBD. Any compatible active pharmaceutical, veterinary and/or nutraceutical ingredient may be included. In some embodiments, the further active ingredient may be selected from any one or more of the following: anti-inflammatories, analgesics, opiates, anticonvulsants, antibiotics, anti-helmintic, steroids and hormones, anaesthetic agents, sedatives, anti-ulcer, anti-emetics, tranquilisers, antiparasitic agents, bronchodilators, decongestants, reflux medications, anti-pyretics, diuretics, antiparasitic agents, antiprutitic agents, and sympathomimetic agents.

When present, the further active pharmaceutical, veterinary and/or nutraceutical ingredient is included in a therapeutically useful amount which is sufficient to provide a suitable dosage to a subject following administration. Accordingly, the composition may comprise an effective amount of a further active pharmaceutical, veterinary and/or nutraceutical ingredient.

In some embodiments, each further active pharmaceutical, veterinary and/or nutraceutical ingredient is present in a minimum amount of at least about 0.0001%, 0.0005%, 0.001%, 0.005%, 0.01% or 0.05%. In some embodiments, each further active pharmaceutical, veterinary and/or nutraceutical ingredient is present in a maximum amount of not more than about 10%, 5%, 1% or 0.5%. The composition may comprise each further active pharmaceutical, veterinary and/or nutraceutical ingredient from any of these minimum amounts to any of these maximum amounts, for example, from about 0.0001% to about 10% or from about 0.01% to about 1%.

References to the various compounds described herein, such as THC and CBD, include the relevant compound and pharmaceutically, veterinary and/or nutraceutically acceptable salts, tautomers and solvates thereof.

The various compounds may be provided as salts which are pharmaceutically, veterinary and/or nutraceutically acceptable. Examples of pharmaceutically and veterinary acceptable salts include salts of pharmaceutically, veterinary and/or nutraceutically acceptable cations such as sodium, potassium, lithium, calcium, magnesium, ammonium and alkylammonium; acid addition salts of pharmaceutically, veterinary and/or nutraceutically acceptable inorganic acids such as hydrochloric, orthophosphoric, sulfuric, phosphoric, nitric, carbonic, boric, sulfamic and hydrobromic acids; or salts of pharmaceutically, veterinary and/or nutraceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups (if present) may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid.

It should be understood that a reference to a pharmaceutically, veterinary and/or nutraceutically acceptable salt includes the solvent addition forms or crystal forms thereof, particularly solvates or polymorphs.

A "tautomer" is a structural isomer of a compound that is in equilibrium with another of the compound's structural isomers. This equilibrium is typically driven by thermodynamics making isolation of only one tautomer of a compound that exhibits tautomerism impossible by conventional techniques. To the extent that any of the present compounds exhibit tautomerism, it is intended that the invention includes all tautomers of the various compounds and derivatives thereof.

The compound(s) may exist in unsolvated as well as solvated forms with acceptable solvents such as water, ethanol, and the like. Solvates contain either stoichiometric or non-stoichiometric amounts of a solvent. Hydrates are formed when the solvent is water. Alcoholates are formed when the solvent is an alcohol. In general, the solvated forms are considered equivalent to the unsolvated forms for the purposes of the compositions and methods provided herein.

The liquid compositions may additionally comprise a pharmaceutically, veterinary and/or nutraceutically acceptable additive. The additive may be selected from the group consisting of one or more colorants, bulking agents, excipients, binders, preservatives, flavouring agents, buffers, artificial and natural sweeteners, dispersants, thickeners and solubilising agents, and combinations thereof.

The additive may be any additive included in the United States Pharmacopeia/National Formulary (USP/NF), the British Pharmacopoeia (BP), the European Pharmacopoeia (EP), the Japanese Pharmacopoeia (JP) or the Chinese Pharmacopoeia (ChP). In some embodiments, the composition comprises an additive which may be non-natural (e.g. synthetically produced).

The liquid compositions may be formulated according to techniques such as those well known in the art of pharmaceutical, veterinary and/or nutraceutical formulation (see, for example, Remington: The Science and Practice of Pharmacy, 21st Ed., 2005, Lippincott Williams & Wilkins and/or Veterinary pharmacology and therapeutics, Riviere, J. (Ed.); Papich, Mark G., (Ed.); Wiley-Blackwell; 2017).

The pharmaceutical, veterinary and/or nutraceutical compositions may be prepared in unit dosage form. In such form, the compositions are subdivided into unit doses containing appropriate quantities of the ingredient(s). The unit dosage form can be a packaged preparation, the package containing discrete quantities of preparation. The preparation may be a solution, suspension, emulsion, elixir, tincture or capsule filled with a solution, suspension, emulsion, elixir or tincture.

For preparing pharmaceutical, veterinary and/or nutraceutical compositions described herein, pharmaceutically, veterinary and/or nutraceutically acceptable additives can be either solid or liquid. In the case of solid additives, these should be soluble and/or dispersible within the liquid components of the liquid composition such that the composition is provided in liquid form.

The liquid compositions of the invention may be sterile. Sterile liquid form compositions include sterile solutions, suspensions, emulsions, syrups and elixirs.

Typically, the administration of the compositions is oral administration. The compositions may be formulated for oral administration in any suitable form. For example, compositions for oral administration may be formulated in one or more of the following liquid forms: a solution, a suspension, an emulsion, an elixir, a syrup, or a capsule filled with a solution, a suspension, an emulsion, an elixir, a syrup, a tincture or a combination thereof.

In some embodiments, the dosage unit form may be a capsule. To form a capsule, typically the ingredient(s) are combined with one or more of pharmaceutically, veterinary and/or nutraceutically acceptable excipients (e.g. carriers) to provide a liquid composition, which is then encased within a capsule shell. Any suitable capsule shell known in the art may be used, including hard and soft capsule shells. Suitable hard capsule shells may comprise gelatine, HPMC, starch, pullulan and/or polyvinyl acetate (PVA). Suitable soft capsules may comprise gelatin thickened with a thickening agent, such as a polyol (e.g. glycerine or sorbitol). As noted above, the capsule shell may be filled with any of the following dosage forms described herein: a solution, a suspension, an emulsion, an elixir, a syrup, or a combination thereof.

Various other materials may be present as coatings or to otherwise modify the physical form of the dosage unit. For instance, capsules may be coated with shellac, sugar or both. Of course, any material used in preparing any dosage unit form should be pharmaceutically, veterinary and/or nutraceutically acceptable and substantially non-toxic in the amounts employed. In addition, the liquid composition may be incorporated into sustained-release preparations and formulations.

Also included are preparations that are intended to be diluted, shortly before use. In such cases, a concentrated form of the liquid composition of the invention (e.g. a form lacking all or part of an oral delivery system) may be diluted with a liquid carrier (such as an oral delivery system) shortly before use. Alternatively, a liquid composition of the invention may be further diluted with a liquid carrier shortly before use.

In some embodiments, a liquid composition of the invention is incorporated into a food product. Accordingly, in another aspect, there is provided a food product comprising the liquid composition of the invention. It will be appreciated that the food product is not limited to liquids. Suitable food products include solid food products including baked goods and liquid food products such as a beverage. The composition may be incorporated into the food product during manufacture or may be added to an existing product. Therefore, the food products disclosed herein may further comprise at least one Generally Recognised As Safe (GRAS) ingredient. The GRAS ingredient may be any ingredient included in the GRAS database maintained by the US Food and Drug Administration (FDA). In some embodiments, the food product is an animal treat, such as a dog biscuit.

The food product may be a functional food product, wherein the food product also comprises a pharmaceutically, veterinary and/or nutraceutically active ingredient. Any of the active pharmaceutical, veterinary and/or nutraceutical ingredients described above may be included in the functional food. The active pharmaceutical, veterinary and/or nutraceutical ingredient may be included as a part of the composition, or may be incorporated separately into the functional food product.

Pharmaceutically, veterinary and/or nutraceutically acceptable carriers and/or diluents include any and all solvents, dispersion media, coatings, antibacterial and antifungal agents, isotonic and absorption delaying agents and the like.

When desired, formulations adapted to give sustained release of the active ingredient(s) may be employed. In addition, the liquid compositions may be formulated to provide a self-emulsifying drug delivery system (SEED), a lipid-based drug-delivery system (LBDDS) and/or a self-microemulsifying drug delivery system (SMEDDS).

The practice of the present invention employs, unless otherwise indicated, conventional pharmaceutical and/or medical techniques within the skill of the art. Such techniques are well known to the skilled worker, and are explained fully in the literature.

Also provided is a method of preparing the liquid composition of the invention. The method comprises:

- preparing a THC solution comprising THC and a liquid carrier;
- preparing a CBD solution comprising CBD and a liquid carrier; and
- combining an aliquot of the THC solution with an aliquot of the CBD solution to provide a liquid composition comprising a combination of THC and CBD.

Typically, the THC solution comprises a first concentration of THC and the CBD composition comprises a second concentration of CBD. The first and second concentrations may be predetermined or assessed through an analytical technique. Any suitable analytical technique may be employed, including GC, HPLC and UPLC.

Preparing a liquid composition according to this method allows for the control of the final ratio of THC:CBD. If either the THC or CBD is obtained by extraction of Cannabis plant material, the concentration of the THC or CBD may vary from extract to extract. Regardless of source of the THC and CBD, this method allows adjustment of the volume of the aliquots to ensure the final ratio of THC and CBD in the liquid composition.

The liquid carrier of the THC and/or CBD composition may comprise an oral delivery system. Any oral delivery system described herein may be used.

In some embodiments, the method further comprises dilution of the liquid composition. The liquid composition may be diluted with an oral delivery system. Any oral delivery system described herein may be used.

The liquid composition produced by this method may be any of the liquid compositions described herein.

Methods of Treatment

The liquid composition of the invention may be used to treat any disease, disorder or condition associated with the endocannabinoid system. THC and CBD therapy have been indicated as useful in the treatment of one or more of the following disease, disorders and conditions: pain control—post operative, arthritis, cancer, neuropathic, injury, anxiety relief, epilepsy treatment, gastro-intestinal health conditions, improved skin health—atopic dermatitis, itching, appetite stimulation, palliative care, anti-inflammatory, alleviates glaucoma, improved joint and bone health, aid for sleep, nervous system support including OCD, depression, migraines, autism, an allergy (e.g. a contact allergy, a food allergy or any other allergy), reduced vomiting and nausea, helps suppress muscle spasms, management of phobias, management of behaviour disorders, management of cognitive dysfunction, reduction in cancer growth, killed or slowed bacteria/fungal growth, reduced blood sugar levels and imbalances of fatty acids.

In particular, the invention provides a method of treating pain, inflammation and/or anxiety. The method comprises administering to a subject in need thereof an effective amount of the liquid composition of the invention. Any of the liquid compositions of the invention described herein may be employed in these methods.

The pain treated in the present methods may be nociceptive pain, psychogenic pain and/or neuropathic pain. Nociceptive pain is associated with stimulation of sensory nerve endings (or nociceptors). Psychogenic pain is associated with psychological factors resulting in a pain disorder (often diagnosed when other physical causes for pain are ruled out). Neuropathic pain is associated with damage or malfunction of the peripheral nervous system (PNS) or central nervous system (CNS). Cannabinoid receptors (e.g. CB1 and CB2 receptors) have been reported as being expressed in the PNS and CNS. The pain to be treated may be any pain associated with the endocannabinoid system.

The inflammation treated in the present methods may be any form of inflammation associated with the activity of the endocannabinoid system. The inflammation may be localised or systemic.

In some embodiments, the inflammation may be a symptom or a cause a disease and/or disorder. The disease and/or disorder may be selected from osteoarthrisis (OA), rheumatoid arthritis (RA), psoriatic arthritis (PsA), ankylosing spondylitis (AS), non-radiographic axial spondyloarthritis (nr-axSpA), idiopathic arthritis, anterior knee pain, chilblains, chronic recurrent multifocal osteomyelitis, fibromyalgia, familial Mediterranean fever (FMF), gout, growing pains, haemochromatosic arthritis, localised scleroderma, lupus, polymyalgia rheumatica, reactive arthritis, ross river fever, scleroderma, Sever's disease, Sjogren's syndrome and spondyloarthritis, or a combination thereof.

The anxiety treated in the present methods may be any form of anxiety associated with the endocannabinoid system or associated with a subject's experience of a disease and/or condition associated with the endocannabinoid system such as an inflammatory disease and/or disorder, and/or pain. The anxiety may be generalised anxiety or a specific anxiety (e.g. a phobia, anxiety to sound or travel, separation anxiety, etc.). Anxiety is experienced by humans and non-human animals alike. In dogs, for example, one measure of anxiety reduction is heart rate. It was surprisingly found that for embodiments of this invention comprising a lower amount of THC relative to CBD that the average heart rate of the subjects was reduced across the treatment period.

The method comprises administering an effective amount of the liquid composition of the invention. The effective amount may be determined by the skilled person based on numerous factors, including the severity and kind of symptoms of the subject, the subject's medical history, the subject's physical attributes (weight, sex, etc), the specific combination of active ingredients included in the pharmaceutical compositions to be administered.

In some embodiments, the liquid composition is administered to the subject to provide a minimum dose of THC of at least about 0.001 mg/kg, 0.005 mg/kg, 0.01 mg/kg, 0.05 mg/kg, 0.1 mg/kg, 0.12 mg/kg, 0.15 mg/kg or 0.2 mg/kg. The maximum dose of THC provided to the subject may be not more than about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.4 mg/kg, 0.3 mg/kg, 0.25 mg/kg or 0.24 mg/kg. The dose of THC administered to the subject may be from any of these minimum amounts to any of these maximum amounts, for example, from about 0.001 mg/kg to about 10 mg/kg, about 0.01 mg/kg to about 1 mg/kg, about 0.1 mg/kg to about 0.3 mg/kg or about 0.12 mg/kg to about 0.24 mg/kg.

In some embodiments, the liquid composition is administered to the subject to provide a minimum dose of CBD of at least about 0.001 mg/kg, 0.005 mg/kg, 0.01 mg/kg, 0.05 mg/kg, 0.1 mg/kg, 0.12 mg/kg, 0.15 mg/kg or 0.2 mg/kg. The maximum dose of CBD provided to the subject may be not more than about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.4 mg/kg, 0.3 mg/kg, 0.25 mg/kg or 0.24 mg/kg. The dose of CBD administered to the subject may be from any of these minimum amounts to any of these maximum amounts, for example, from about 0.001 mg/kg to about 10 mg/kg, about 0.01 mg/kg to about 1 mg/kg, about 0.1 mg/kg to about 0.3 mg/kg or about 0.12 mg/kg to about 0.24 mg/kg.

Any of the doses of THC and CBD given above may be combined without limitation, and may be dictated, for example, on the ratio of THC:CBD contained in the composition.

The liquid compositions of the invention may be administered with or without food. In some embodiments, the subject is fasted for at least about 3, 6, 8, 10 or 12 hours prior to administration. In other embodiments, the liquid composition may be administered within about 0.5, 1 or 2 hours of consuming food.

The method comprises administering at least two active ingredients, namely THC and CBD optionally together with a further active ingredient. While in some embodiments, the THC and CBD are formulated into the same a liquid composition, some embodiments of these methods may involve administering the active compounds simultaneously, separately or consecutively. By simultaneously it is meant that each of the active ingredients are administered at the same time in the same composition. By separately it is meant that each of the active ingredients are administered at the same time in different compositions and optionally by different routes of administration. By consecutively it is meant that each of the composition and the further active ingredient are administered separately optionally by different administration routes and may be at different times. Typically, when the active ingredients are administered consecutively they are administered within 24 hours, or within 12, 8, 6, 5, 4, 3, 2, or 1 hour(s) of each other. THC may be administered before or after the CBD.

The THC and CBD may be administered 1, 2, 3, 4 or more times per day as required based on the disease, disorder and/or condition to be treated. Typically, the composition is administered once daily or twice daily (BID).

In some embodiments, the peak THC plasma concentration may be achieved within about 3, 2, 1.5 or 1 hours after administration. The peak THC plasma concentration may occur after at least about 0.2, 0.3, 0.4, 0.5, 0.6 or 0.67 hours after administration. The peak THC plasma concentration may be achieved from about 0.2 hours to about 3 hours after administration or about 0.67 hours to about 1.5 hours after administration.

In some embodiments, the peak CBD plasma concentration may be achieved within about 3, 2, 1.5 or 1 hours after administration. The peak CBD plasma concentration may occur after at least about 0.2, 0.3, 0.4, 0.5, 0.6 or 0.67 hours after administration. The peak CBD plasma concentration may be achieved from about 0.2 hours to about 3 hours after administration or about 0.67 hours to about 1.5 hours after administration.

While the absorption of THC and CBD from the composition may be considered independent even when dosed simultaneously, in some embodiments, the peak plasma concentration for both THC and CBD is achieved within about 0.5, 0.4, 0.3 or 0.2 hours.

In some embodiments, the peak THC plasma concentration ($C_{max}$) achieved was from about 19 ng/mL to about 71.3 ng/mL. Surprisingly, it was observed that THC was detectable in the subject's blood 72 h after administration. Accordingly, in some embodiments, the THC plasma concentration may be at least about 0.11 ng/ml, 0.22 ng/mL, 0.28 ng/ml, 0.34 ng/ml, 0.47 ng/ml, 0.58 ng/ml, 1.48 ng/ml, 1.91 ng/ml, 10.5 ng/ml, 71.3 ng/mL. The plasma THC concentration achieved may be from any of these concentrations to any other of these concentrations, for example, from about 0.11 ng/ml to about 71.3 ng/ml, about 0.22 ng/mL to about 0.58 ng/mL, about 1.48 ng/mL to about 10.5 ng/mL, about 0.47 ng/mL to about 1.91 ng/mL, or about 0.11 ng/mL to about 0.46 ng/mL.

In some embodiments, the peak CBD plasma concentration ($C_{max}$) achieved was from about 5 ng/mL to about 69 ng/mL. Surprisingly, it was observed that CBD was detectable in the subject's blood up to 72 h after administration. Accordingly, in some embodiments, the CBD plasma concentration may be at least about 0.23 ng/mL, 0.26 ng/mL, 0.28 ng/mL, 0.46, ng/mL, 0.76 ng/mL, 0.88 ng/mL, 5.74 ng/mL, 69 ng/mL. The plasma CBD concentration achieved may be from any of these concentrations to any other of these concentrations, for example, from about 0.23 ng/ml to about 69 ng/ml, about 0.76 ng/mL to about 5.74 ng/mL, about 0.11 ng/mL to about 0.46 ng/mL or about 0.23 ng/mL to about 0.88 ng/mL.

Any of the THC and/or CBD plasma concentrations described herein, without limitation, may be maintained after administration for at least about 6, 12, 18, 24, 32 hours or longer.

In addition to plasma concentration, it is also useful to calculate the area under the curve (AUC) for an administered active ingredient. In some embodiments, the AUC for THC concentration after administering a dose of 0.12 mg/kg THC in combination with 0.24 mg/kg CBD to a canine subject may be from about 90 to about 110, for example about 95 to about 100. The AUC for THC concentration after administering a dose of 0.24 mg/kg THC in combination with 0.12 mg/kg CBD to a canine subject may be from about 145 to about 170, for example about 150 to about 160. In some embodiments, the AUC for CBD concentration after administering a dose of 0.12 mg/kg CBD in combination with 0.24 mg/kg THC to a canine subject may be from about 30 to about 50, for example about 35 to about 45. The AUC for CBD concentration after administering a dose of 0.24 mg/kg CBD in combination with 0.12 mg/kg THC to a canine subject may be from about 95 to about 110, for example about 100 to about 105. These AUC results show that both THC and CBD achieve measurable plasma concentrations after oral dosing of the liquid composition of the invention. Surprisingly, the AUC of THC following administration of 0.24 mg/kg THC/0.12 mg/kg CBD is less than 2 times that of the AUC of the AUC of THC following administration of 0.12 mg/kg THC/0.24 mg/kg CBD. Similarly, it was surprisingly found that the AUC of CBD achieved following administration of 0.12 mg/kg THC/0.24 mg/kg CBD is more than twice that of the AUC of CBD following administration of 0.24 mg/kg THC/0.12 mg/kg CBD. This relative improvement in bioavailability for both THC and CBD suggest a synergistic effect in terms of oral absorption for the high-CBD compositions of the invention.

The subject to be treated may be a human or a non-human subject. Non-human subjects may be any animal possessing an endocannabinoid system. It is believed that the endocannabinoid system is highly conserved across all vertebrates as well as in some invertebrates too. The term “animal” as used herein includes but is not limited to companion animals, food-production animals and zoo animals. Companion animals include dogs, cats, guinea pigs, hamsters and horses. Food-production animals include cattle, goats, sheep, fowl, poultry and swine. Zoo animals include monkeys, elephants, giraffes and other ungulates, bears, mice and other small mammals. Typically, the subject is a dog or cat, most typically a dog.

In another aspect, the invention provides a method of controlling the heart rate of a subject. The method comprises orally administering to the subject an effective amount of a liquid composition of the invention.

In some embodiments, controlling the heart rate means lowering the average heart rate of the subject for a period of time following the oral administration. In these embodiments, the liquid composition may be a high-CBD composition.

The liquid composition may be dosed in any of the effective amounts described herein. The pharmacokinetic profile for the THC and CBD following administration may therefore also be any plasma concentration profile described herein.

In some embodiments, controlling the heart rate means preventing elevation of the average heart fora period of time following administration.

The period of time following administration may be at least about 2, 3, 4, 5, 6, 7, 8, 9, 10, 11, 12, 14, 16, 18, 20, 24 hours or longer, for example up to about 72 hours.

Also disclosed herein is a kit of parts comprising in separate parts:

(a) a liquid composition comprising THC and an oral delivery system; and
(b) a liquid composition comprising CBD and an oral delivery system.

The oral delivery system of parts (a) and (b) may be any oral delivery system described herein. Typically, the oral delivery system of parts (a) and (b) is the same. In some embodiments, parts (a) and (b) may be combined to provide a liquid composition of the invention.

Gene Expression

One aspect of the invention provides a method of modulating the expression of one or more genes selected from chemokine (C-C motif) ligand 5 (CCL5, as shown in SEQ ID NO:4), cerebellar degeneration-related protein 2 (CDR2, as shown in SEQ ID NO:2), cannabinoid receptor 2 (macrophage) (CNR2, as shown in SEQ ID NO:3), interleukin 8 (CXCL8, as shown in SEQ ID NO:1) and adrenoreceptor beta 2 (ADRB2, as shown in SEQ ID NO:5). In some embodiments, the expression of all of these genes may be modulated in these methods.

In some embodiments, the method comprises contacting a cell with a combination of THC and CBD.

In some embodiments, contacting the cell with the combination of THC and CBD may be achieved by administering to a subject a combination of THC and CBD.

The combination of THC and CBD may be provided in the form of any of the liquid compositions described herein. The liquid compositions may be provided to the cell and/or administered to the subject in any of the dosages described herein.

Chemokine (C-C motif) ligand 5 gene (CCL5) encodes a chemokine and functions as a chemoattractant for blood monocytes, memory T helper cells and eosinophils. It causes the release of histamine from basophils and activates eosinophils. Among its related pathways are pigment epithelium-derived factor (PEDF) induced signaling and toll like receptor signaling pathway. Therefore, an upregulation of this gene may result in improved immune cell communication, organization and coordination.

Cannabinoid Receptor 2 gene (CNR2) encodes the CB2 receptor also known as the peripheral cannabinoid receptor. The CB2 receptor is located primarily in immune cells both within and outside of the CNS. The upregulation of this gene may reinforce the physiological uptake involved in metabolism of the treated active compounds at a cellular level.

Interleukin 8 gene (CXCL8) encodes interleukin 8 (IL-8), which is a protein that is a member of the CXC chemokine family and is a major mediator of the inflammatory response. The encoded protein is secreted primarily by neutrophils, where it serves as a chemotactic factor by guiding the neutrophils to the site of infection. This chemokine is also a potent angiogenic factor. Among its related pathways are PEDF Induced Signaling. IL-8 is a chemotactic factor that attracts neutrophils, basophils, and T-cells, but not monocytes. It is also involved in neutrophil activation. It is released from several cell types in response to an inflammatory stimulus. It is a potent proinflammatory cytokine and implicated in various pain states including cancer pain. A downregulation of this gene suggests an anti-inflammatory effect.

The cerebellar degeneration-related protein 2 gene (CDR2) encodes a protein that plays a role in cellular calcium transport and nerve function at the mitochondrial level. CDR2 is linked with CB1 receptor activation and is believed to form part of a pathway for the neuroprotective role attributed to CBD.

The adrenoreceptor beta 2 gene (ADRB2) encodes the beta-2 adrenergic receptor. Adrenaline is a ligand of this receptor. ADRB2 has been linked to the pain response, where antidepressants have been reported as suppressing neuropathic pain mediated by a peripheral β-adrenoreceptor mediated anti-tumour necrosis factor-α (TNFα) mechanism. Actions of ADRB2 are related to facilitation of the fightor-flight response but also are involved in neuroinflammatory processes. ADRB2 stimulation is also thought to increase migration of hematopoietic progenitor cells and stem cells.

The expression levels of a gene may be determined according any technique known in the art.

In some embodiments, CNR2 is upregulated following administration of the combination of THC and CBD. The upregulation may be at least about 0.5-fold, 1-fold, 1.5-fold, 2-fold, 2.5-fold or 3-fold increase over expression levels of the gene in a sample obtained prior to exposure to the combination of THC and CBD. The upregulation may persist for at least about 1, 1.5, 6, 12, 18, 24, 48, 36, 72 hours or longer after THC and CBD exposure.

In some embodiments, ADRB2 is upregulated following administration of the combination of THC and CBD. The upregulation may be at least about 0.5-fold, 1-fold, 1.5-fold, 2-fold, 2.5-fold or 3-fold increase over expression levels of the gene in a sample obtained prior to exposure to the combination of THC and CBD. The upregulation may persist for at least about 1, 1.5, 6, 12, 18, 24, 48, 36, 72 hours or longer after THC and CBD exposure.

In some embodiments the regulation of a gene (upregulation or downregulation) varies depending on the ratio of THC:CBD exposed to the cell and/or administered to the subject. In some embodiments, exposure to a high-THC composition may result in a downregulation of CCL5. The downregulation may be at least about −0.5-fold or −1-fold change over expression levels of the gene in a sample obtained prior to exposure to THC and CBD. The downregulation may persist for at least about 1, 1.5, 6, 12, 18, 24, 48, 36, 72 hours or longer after THC and CBD exposure. In some embodiments, exposure to a high-CBD composition may result in an upregulation of CCL5. The upregulation may be at least about 0.5-fold, 1-fold, 1.5-fold, 2-fold, 2.5-fold or 3-fold increase over expression levels of the gene in a sample obtained prior to exposure to the combination of THC and CBD. The upregulation may persist for at least about 1, 1.5, 6, 12, 18, 24, 48, 36, 72 hours or longer after THC and CBD exposure.

In some embodiments, exposure to a high-CBD composition may result in a downregulation of CXCL8. The downregulation may be at least about −0.5-fold or −1-fold change over expression levels of the gene in a sample obtained prior to exposure to THC and CBD. The downregulation may persist for at least about 1, 1.5, 6, 12, 18, 24, 48, 36, 72 hours or longer after THC and CBD exposure. In some embodiments, exposure to a high-THC composition may result in an upregulation of CXCL8. The upregulation may be at least about 0.5-fold, 1-fold, 1.5-fold or 2-fold increase over expression levels of the gene in a sample obtained prior to exposure to the combination of THC and CBD. The upregulation may persist for at least about 1, 1.5, 6, 12, 18, 24, 48, 36, 72 hours or longer after THC and CBD exposure.

In some embodiments, exposure to a high-THC composition may result in a downregulation of CDR2. The downregulation may be at least about −0.5-fold, −1-fold, −1.5-fold or −2-fold change over expression levels of the gene in a sample obtained prior to exposure to THC and CBD. The downregulation may persist for at least about 1, 1.5, 6, 12, 18, 24, 48, 36, 72 hours or longer after THC and CBD exposure. In some embodiments, exposure to a high-CBD composition may also result in downregulating and/or upregulating CDR2, for example, within about 70, 48, 36, 24, 12, 6, 5, 4, 3 or 2 hours of THC and CBD exposure, expression of CDR2 may be downregulating, while after about 2, 3, 4, 5, 6, 12, 24, 36, 48 or 70 hours of treatment CDR2 expression may be upregulated. The CDR2 downregulation may be about −0.5-fold, −1-fold or −1.2-fold change over expression levels of the gene in a sample obtained prior to exposure to THC and CBD. The CDR2 upregulation may be about 0.5-fold, 1-fold or 1.2-fold change over expression levels of the gene in a sample obtained prior to exposure to THC and CBD. The downregulation may persist for at least about 1, 1.5, 6, 12, 18, 24, 48, 36, 72 hours or longer after THC and CBD exposure.

In some embodiments, the invention provides a method of downregulating CCL5 and CDR2 and upregulating CNR2, CXCL8 and ADRB2, comprising contacting a cell with a combination of THC and CBD, wherein the ratio by weight of THC:CBD is 1 or more: 1. The combination may be provided in the form of any of the high THC liquid compositions described herein. The step of contacting the cell with the combination of THC and CBD may comprise administering the combination of THC and CBD to a subject.

In some embodiments, the invention provides a method of downregulating CXCL8 and CDR2 and upregulating CCL5, CNR2 and ADRB2, comprising contacting a cell with a combination of THC and CBD, wherein the ratio by weight of THC:CBD is 1:1.2 or more. The combination may be provided in the form of any of the high-CBD compositions described herein. The step of contacting a cell with the combination of THC and CBD may comprise administering the combination of THC and CBD to a subject.

In some embodiments, the invention provides a method of downregulating CXCL8 and upregulating CCL5, CNR2 and ADRB2, comprising contacting a cell with a combination of THC and CBD, wherein the ratio by weight of THC:CBD is 1:1.2 or more. The combination may be provided in the form of any of the high-CBD compositions described herein. The step of contacting a cell with the combination of THC and CBD may comprise administering the combination of THC and CBD to a subject.

In some embodiments, the method of gene regulation is also a method for treating pain, inflammation and/or anxiety.

Biomarkers

One aspect of the invention provides a method of affecting the concentration of a biomarker associated with inflammation. The biomarker may be selected from granulocyte-macrophage colony-stimulating factor (GM-CSF) and interleukin-15 (IL-15) or a combination thereof.

In some embodiments, the method comprises contacting a cell with a combination of THC and CBD. The step of contacting the cell with the combination of THC and CBD may comprise administering the combination of THC and CBD to a subject.

The combination of THC and CBD may be provided in the form of any of the liquid compositions described herein.

The concentration of GM-CSF is decreased when a combination of THC and CBD is contacted with the cell and/or administered to the subject. Accordingly, the combination may be provided by any of the liquid compositions described herein. In some embodiments, the maximum peak plasma concentration of GM-CSF following administration of the combination of THC and CBD may be up to about 180 pg/ml, 150 pg/ml, 120 pg/ml, 100 pg/ml, 80 pg/ml, or 70 pg/ml. The minimum peak plasma concentration of GM-CSF CSF following administration of the combination of THC and CBD may be at least about 20 pg/ml, 30 pg/ml or 40 pg/ml. The peak plasma concentration of GM-CSF CSF following administration of the combination of THC and CBD may be from any of these minimum amounts to any of these maximum amounts, for example, from about 20 pg/ml to about 180 pg/ml or about 40 pg/ml to about 80 pg/ml. The peak concentration of GM-CSF following administration of the combination of THC and CBD may occur within about 7, 6, 5, 4, 3 or 2 hours following administration.

In some embodiments, there is provided a method of decreasing the concentration of interleukin 15, comprising contacting a cell with a combination of THC and CBD, wherein the ratio by weight of THC:CBD is 1 or more: 1. The combination may be provided in the form of any of the high THC liquid compositions described herein.

In some embodiments, there is provided a method of decreasing the concentration of interleukin 15, comprising administering to a subject a combination of THC and CBD, wherein the ratio by weight of THC:CBD is 1 or more: 1. The combination may be provided in the form of any of the high THC liquid compositions described herein.

In these methods of decreasing IL-15 concentration, the maximum peak plasma concentration of IL-15 following administration of the combination of THC and CBD may be up to about 150 pg/ml or 100 pg/ml. The minimum peak plasma concentration following administration of the combination of THC and CBD of IL-15 may be at least about 20 pg/ml, 40 pg/ml or 50 pg/ml. The peak plasma concentration of IL-15 following administration of the combination of THC and CBD may be from any of these minimum amounts to any of these maximum amounts, for example, from about 20 pg/ml to about 150 pg/ml. The peak plasma concentration of IL-15 following administration of the combination of THC and CBD may be reached within about 4.5 hours following administration.

In some embodiments, there is provided a method of increasing the concentration of interleukin 15, comprising contacting a cell with a combination of THC and CBD, wherein the ratio by weight of THC:CBD is 1:1.2 or more. The combination may be provided in the form of any of the high-CBD compositions described herein.

In some embodiments, there is provided a method of increasing the concentration of interleukin 15, comprising administering to a subject a combination of THC and CBD, wherein the ratio by weight of THC:CBD is 1 or more: 1. The combination may be provided in the form of any of the high-CBD compositions described herein.

In these methods of increasing IL-15 concentration, the maximum peak plasma concentration of IL-15 following administration of the combination of THC and CBD may be up to about 1500 pg/ml, 1000 pg/ml, 750 pg/ml, 650 pg/ml or 600 pg/ml. The minimum peak plasma concentration following administration of the combination of THC and CBD of IL-15 may be at least about 250 pg/ml, 300 pg/ml, 350 pg/ml, 400 pg/ml, 450 pg/ml or 500 pg/ml. The peak plasma concentration of IL-15 following administration of the combination of THC and CBD may be from any of these minimum amounts to any of these maximum amounts, for example, from about 250 pg/ml to about 1500 pg/ml. The peak plasma concentration of IL-15 following administration of the combination of THC and CBD may be reached within about 4.5, 4 or 3.5 hours following administration. By way of comparison, peak plasma concentration of IL-15 following administration of vehicle only is about 220 pg/ml achieved at about 5 hours after administration.

Some embodiments of the methods of treatment described herein further comprise affecting the concentration of GM-CSF and/or IL-15.

The concentration of a biomarker in a sample taken from a subject may be determined according any technique known in the art.

EXAMPLES

The invention will be further described by way of non-limiting example(s). It will be understood to persons skilled in the art of the invention that many modifications may be made without departing from the spirit and scope of the invention.

Example 1—Administration of Cannabinoid Containing Compositions to Dogs

This Example describes single oral dosing to dogs of two compositions comprising different ratios of THC and CBD. After administration, blood was taken from the animals and they were observed for evidence of adverse effects or toxicity.

Two compositions, IVP1 and IVP2, were administered in varying amounts in the study. The IVP's can be administered separately as in the case of the present study or they can be mixed together to provide a fixed ratio of THC and CBD as described in Examples 2 and 3.

Investigational Veterinary Product 1 (IVP1):

Composition—4.75 mg/ml THC in MCT oil; Formulation type—Oil-based solution

Investigational Veterinary Product 2: (IVP2):

Composition—4.58 mg/ml CBD in MCT oil; Formulation type—Oil-based solution

Control Veterinary Product (CVP):

Composition—Medium Chain Triglyceride (MCT) oil no active ingredients; Formulation type—Carrier oil Design Eleven (11) dogs received single concomitant oral doses of cannabidiol (CBD) and tetrahydrocannabinol (THC) oils, or placebo.

Three (3) dogs served as controls and received MCT oil with no active ingredients (Treatment 1).

Treatment 2 were dosed with IVP1 and IVP2 in a 2:1 ratio which was administered to four (4) dogs.

Treatment 3 were dosed with IVP1 and IVP2 in a 1:2 ratio which was administered to four (4) dogs.

Dose Calculation

Dogs were treated on individual Day −1 bodyweights as indicated in Table 2 below. Dosage volumes were calculated prior to Day 0, to provide the target dosage in mg/kg bodyweight based on actual dog bodyweights and IVP active ingredient composition based on the Certificates of Analysis.

TABLE 2

Treatment Regime

| Treatment Group | Dose Rate | Route | Frequency | Treatment Day | Number of Animals |
|---|---|---|---|---|---|
| 1 | MCT oil 0.1 mL/kg | Oral | Once | 0 | 3 (Dogs 9-11) |
| 2 | 0.24 mg/kg THC and 0.12 mg/kg CBD | Oral | Once | 0 | 4 (Dogs 1-4) |

TABLE 2-continued

| Treatment Regime | | | | | |
|---|---|---|---|---|---|
| Treatment Group | Dose Rate | Route | Frequency | Treatment Day | Number of Animals |
| 3 | 0.12 mg/kg THC and 0.24 mg/kg CBD | Oral | Once | 0 | 4 (Dogs 4-8) |

Monitoring and Recording Adverse Events

Each study animal was closely monitored throughout the study period for the development of the following clinical signs (which have been associated with THC toxicity): sedation/lethargy, agitation/involuntary movement, locomotion issues, eye changes, coughing, drooling/salivating, gagging/retching, vomiting, diarrhea, incontinence, heart rates, respiratory rates, temperature changes, and/or any other abnormal observation.

A serious adverse event (SAE) was defined as an AE which is fatal or life-threatening, or results in significant disability or incapacity or a congenital anomaly/birth defect or results in permanent or prolonged signs which require professional intervention beyond routine prevention measures and common first aid. An AE was automatically classified as serious if one of the following reactions was reported: shock (all shock reactions whatever the origin is: circulatory, anaphylactic), collapse, syncope, immune mediated disease (for adverse reaction), seizures/convulsions, blindness, deafness, paralysis/paresis, malignant neoplasia (including sarcomas at the administration site), respiratory distress, dyspnoea, apnoea, failure of vital organs (total loss of function), uterine haemorrhage, uterine rupture, or pyometra, peritonitis, diabetes mellitus (if reports as SAR), and/or injection site reactions with systemic involvement and reduced mobility.

Blood Sampling

Blood samples of approximately 5 mL were collected at each drug concentration sampling time-point from each animal using 22-gauge needles and 5 mL syringes.

Results

TABLE 3

| Actual Dosages Administered | | | | |
|---|---|---|---|---|
| Dog No. | Day −1 weight (kg) | Dosage THC (mg) | CBD dosage (mg) | Treatment Group |
| Dog 1 | 17.6 | 4.22 | 2.11 | 2 |
| Dog 2 | 17.6 | 4.22 | 2.11 | 2 |
| Dog 3 | 20.7 | 4.97 | 2.48 | 2 |
| Dog 4 | 18.2 | 4.37 | 2.18 | 2 |
| Dog 5 | 21.2 | 2.54 | 5.01 | 3 |
| Dog 6 | 18.6 | 2.23 | 4.46 | 3 |
| Dog 7 | 16.1 | 1.93 | 3.86 | 3 |
| Dog 8 | 18.5 | 2.22 | 4.44 | 3 |
| Dog 9 | 17.7 | 0 | 0 | 1 |
| Dog 10 | 21.1 | 0 | 0 | 1 |
| Dog 11 | 20.7 | 0 | 0 | 1 |

The results of the blood sampling are set out for CBD in Table 4 and for THC in Table 5. The data points from Table 4 and Table 5 were also plotted and these graphs are set out in FIGS. 1-16.

TABLE 4

| Results of CBD administration and sampling | | | | | | | | | | |
|---|---|---|---|---|---|---|---|---|---|---|
| Day −1 weight (kg) | 17.6 | 17.6 | 20.7 | 18.2 | | 21.2 | 18.6 | 16.1 | 18.5 | |
| CBD dose (mg) | 2.11 | 2.11 | 2.48 | 2.18 | | 5.01 | 4.46 | 3.86 | 4.44 | |
| CBD (mg/kg) | 0.12 | 0.12 | 0.12 | 0.12 | | 0.24 | 0.24 | 0.24 | 0.24 | |
| Dog ID | 1 | 2 | 3 | 4 | Mean 0.12 mg/kg | 5 | 6 | 7 | 8 | Mean 0.24 mg/kg |
| 0 | 0 | 0 | 0 | 0 | 0.00 | 0 | 0 | 0 | 0 | 0.00 |
| 0.33 | 3.83 | 8.63 | 1.18 | 6.08 | 4.93 | 7.79 | 12.50 | 2.79 | 20.60 | 10.92 |
| 0.67 | 15.60 | 18.10 | 5.26 | 10.10 | 12.27 | 28.70 | 28.10 | 10.20 | 53.40 | 30.10 |
| 1 | 12.00 | 13.60 | 5.99 | 13.10 | 11.17 | 35.20 | 20.10 | 18.90 | 69.10 | 35.83 |
| 1.5 | 7.50 | 7.99 | 9.07 | 9.84 | 8.60 | 33.20 | 27.00 | 12.70 | 34.60 | 26.88 |
| 2 | 6.27 | 4.48 | 8.08 | 8.72 | 6.89 | 23.70 | 14.90 | 12.60 | 20.30 | 17.88 |
| 3 | 2.83 | 2.33 | 5.83 | 6.25 | 4.31 | 9.21 | 6.33 | 6.79 | 7.66 | 7.50 |
| 4 | 1.95 | 1.24 | 4.08 | 4.31 | 2.90 | 5.28 | 4.07 | 4.40 | 4.36 | 4.53 |
| 6 | 1.56 | 0.76 | 2.99 | 2.75 | 2.02 | 3.40 | 2.22 | 5.74 | 1.87 | 3.31 |
| 8 | 1.12 | 0.53 | 1.23 | 2.32 | 1.30 | 4.68 | 1.23 | 4.36 | 0.91 | 2.79 |
| 12 | 0.48 | 0.23 | 0.37 | 0.55 | 0.41 | 0.88 | 0.63 | 0.85 | 0.72 | 0.77 |
| 16 | 0.00 | 0.00 | 0.26 | 0.36 | 0.16 | 0.55 | 0.49 | 0.65 | 0.47 | 0.54 |
| 24 | | | 0.00 | 0.23 | 0.11 | 0.38 | 0.28 | 0.46 | 0.28 | 0.35 |
| 32 | | | | 0.00 | 0.00 | 0.28 | 0.39 | 0.39 | 0.32 | 0.34 |
| 48 | | | | | | 0.00 | 0.22 | 0.31 | 0.00 | 0.13 |
| 72 | | | | | | | 0.00 | 0.00 | | 0.00 |

The results of the CBD sampling provided in Table 4 demonstrate a good uptake of CBD by the subject canines. First peaks or $C_{max}$ were achieved between 0.67 and 1.5 hours in all subjects. First peak concentrations of CBD ranged from 5 ng/mL to 69 ng/mL. The lowest level of CBD recorded in a subject 12 hours post administration was 0.23 ng/mL CBD. The highest level recorded 12 hours post administration was 0.88 ng/mL. CBD concentrations of 0.26 ng/mL and 0.28 ng/mL were recorded in subjects 16 and 32 hours post administration. The calculated $AUC_{0\infty}$ is 0.339 ng·hour/mL and the terminal half-life (t½) of 12.6 hours.

TABLE 5

Results of THC administration and sampling

| Day −1 weight (kg) | 21.2 | 18.6 | 16.1 | 18.5 | | 17.6 | 17.6 | 20.7 | 18.2 | |
|---|---|---|---|---|---|---|---|---|---|---|
| THC (mg/kg) | 2.54 | 2.23 | 1.93 | 2.22 | | 4.22 | 4.22 | 4.97 | 4.37 | |
| CBD (mg/kg) | 0.12 | 0.12 | 0.12 | 0.12 | | 0.24 | 0.24 | 0.24 | 0.24 | |
| **Dog ID** | **5** | **6** | **7** | **8** | **Mean 0.12 mg/kg** | **1** | **2** | **3** | **4** | **Mean 0.24 mg/kg** |
| 0 | 0 | 0 | 0 | 0 | 0.00 | 0 | 0 | 0 | 0 | 0.00 |
| 0.33 | 6.03 | 10.70 | 2.65 | 17.30 | 9.17 | 10.40 | 24.80 | 3.22 | 24.40 | 15.71 |
| 0.67 | 26.60 | 22.80 | 10.50 | 51.50 | 27.85 | 45.40 | 59.00 | 18.50 | 33.00 | 38.98 |
| 1 | 34.30 | 22.10 | 19.60 | 71.30 | 36.83 | 45.20 | 47.80 | 24.20 | 45.60 | 40.70 |
| 1.5 | 30.00 | 30.00 | 14.60 | 36.20 | 27.70 | 30.10 | 31.40 | 36.40 | 32.70 | 32.65 |
| 2 | 22.30 | 17.10 | 13.50 | 19.20 | 18.03 | 25.60 | 17.40 | 32.20 | 29.40 | 26.15 |
| 3 | 8.19 | 7.28 | 7.41 | 8.47 | 7.84 | 10.70 | 8.85 | 22.10 | 21.60 | 15.81 |
| 4 | 4.19 | 4.09 | 4.62 | 4.25 | 4.29 | 6.77 | 3.88 | 15.80 | 14.10 | 10.14 |
| 6 | 2.50 | 2.09 | 5.75 | 1.64 | 3.00 | 4.86 | 1.48 | 10.50 | 8.47 | 6.33 |
| 8 | 3.64 | 0.99 | 4.21 | 0.70 | 2.38 | 3.61 | 0.84 | 4.01 | 7.46 | 3.98 |
| 12 | 0.56 | 0.47 | 0.75 | 0.83 | 0.65 | 1.72 | 0.84 | 0.97 | 1.91 | 1.36 |
| 16 | 0.34 | 0.40 | 0.60 | 0.44 | 0.44 | 0.62 | 0.39 | 0.88 | 1.09 | 0.75 |
| 24 | 0.23 | 0.25 | 0.42 | 0.22 | 0.28 | 0.30 | 0.23 | 0.53 | 0.58 | 0.41 |
| 32 | 0.00 | 0.35 | 0.39 | 0.36 | 0.28 | 0.38 | 0.28 | 0.50 | 0.58 | 0.43 |
| 48 | | 0.00 | 0.27 | 0.001 | 0.09 | 0.23 | 0.001 | 0.37 | 0.37 | 0.24 |
| 72 | | | 0.00 | | 0.00 | 0.00 | | 0.21 | 0.29 | 0.16 |

THC levels recorded in subject's blood plasma fraction are set out in Table 5. First peaks or $C_{max}$ were achieved between 0.67 and 1.5 hours in all subjects. First peak concentrations of CBD ranged from 19 ng/mL to 71.3 ng/mL. The lowest level of CBD recorded in a subject 12 hours post administration was 0.67 ng/mL CBD. The highest level recorded 12 hours post administration was 1.91 ng/mL. CBD concentrations of 0.34 ng/mL and 0.28 ng/mL were recorded in subject's 16 and 32 hours post administration. The calculated $AUC_{0-\infty}$ is 0.6 ng·hour/mL and the half-life (t½) of 18.4 hours.

TABLE 6

Clinical Observations

| Group | Dog | 42 min | 1 hr 10 min | 1 hr 28 min | 2 hr 28 min | 3 hr 10 min | |
|---|---|---|---|---|---|---|---|
| 1 | 9 | Alert, sitting | Alert, standing | Normal | Alert, sitting | Sitting, alert | Dog remained alert for duration |
| 1 | 10 | Active | Alert, standing | Normal | Alert, sitting, jumping | Being bled | Dog remained alert for duration |
| 1 | 11 | Alert | Alert | Normal | Alert | Alert | Dog remained alert for duration |
| 2 | 2 | Alert, standing | Head bobbing, sitting up | Looked sleepy | Asleep | Alert, sitting | Some evidence of relaxation after 1 hr |
| 2 | 1 | Sitting, quiet | Alert, standing | Normal | A bit sleepy, sitting | Dozing, sitting | Some evidence of relaxation after 2.5 hr |
| 2 | 4 | Quiet, asleep | Alert, standing | Sleepy | Asleep | Alert | Some evidence of relaxation from 40 min |
| 2 | 3 | Quiet | Alert, sitting, chewing feet | Licking self, a bit sleepy | A bit sleepy, licking | Dozing | Some evidence of relaxation after 1.5 hr |
| 3 | 7 | Standing | Alert, sitting | Sleeping | Alert | Sitting, dozing | Some evidence of relaxation after 1.5 hr |
| 3 | 5 | Alert, sitting, relaxed | Sitting/lying, alert | Lying down | A bit sleepy | Asleep | Some evidence of relaxation after 2.5 hr |

TABLE 6-continued

| Clinical Observations | | | | | | | |
|---|---|---|---|---|---|---|---|
| Group | Dog | 42 min | 1 hr 10 min | 1 hr 28 min | 2 hr 28 min | 3 hr 10 min | |
| 3 | 6 | Sitting | Alert, standing | A littlesleepy | A bit sleepy, sitting | Alert | Some evidence of relaxation after 1.5 hr |
| 3 | 8 | Quiet (was before) | Alert, sitting | Normal | — | Dozing | Some evidence of relaxation from 3 hr |

Canine subjects were observed for 12 hours post administration. The results of the visual observations are recorded in Table 6. The physical heart rates and respiratory rates recorded for each subject have been included in Table 7 and the averages for each treatment group were plotted against each other in FIGS. 17 and 18 for heart rate and respiratory rate respectively.

It should be noted that the throughout the 12 hours of observation there was no evidence of any adverse effect arising as a result of the administration of CBD/THC. There were two dogs that exhibited red eyes however two of the controls (TG3) also exhibited the same sign and so redness of the eyes was not attributed to the IVP administration. Importantly, no locomotive issues were seen in the second and third treatments groups that received CBD and THC in the administration. Whilst there were some evidence of relaxation or mild sedation the dogs did not seem incapacitated in any way and did not struggle to walk when they got up to move. There were no gastro-intestinal effects observed, such as diarrhoea or vomiting and all the animals were well and ate normally the next day post administration.

TABLE 7

| Heart rate and Respiratory Rate data | | | | | | | | | | |
|---|---|---|---|---|---|---|---|---|---|---|
| Treatment | | Hours Post Treatment | | | | | | | | |
| Group | | 1 | 2 | 4 | 8 | 12 | 24 | 32 | 48 | 72 |
| 1 | HR | 100 | 72 | 80 | 104 | 120 | 120 | 125 | 92 | 100 |
| | RR | 24 | 16 | 20 | 26 | 264 | 20 | 20 | 24 | 28 |
| 2 | HR | 96 | 104 | 120 | 124 | 132 | 120 | 100 | 104 | 112 |
| | RR | 16 | 30 | 24 | sniffing | 32 | 32 | 26 | | 24 |
| 2 | HR | 88 | 92 | 96 | 100 | 104 | 108 | 104 | 100 | 104 |
| | RR | 18 | 24 | 20 | 22 | 18 | 20 | 22 | 32 | 20 |
| 2 | HR | 88 | 100 | 92 | 100 | 104 | 112 | 126 | 112 | 120 |
| | RR | 24 | 18 | 24 | 24 | 20 | panting | 28 | 16 | 24 |
| 1 | HR | 84 | 80 | 100 | 84 | 88 | 100 | 96 | 104 | 108 |
| | RR | 16 | 16 | 24 | sniffing | 16 | panting | 22 | 24 | panting |
| 1 | HR | 120 | 130 | 120 | 124 | 128 | 124 | 136 | 104 | 108 |
| | RR | 36 | 38 | 36 | 36 | 28 | panting | 28 | 24 | 28 |
| 3 | HR | 96 | 10 | 76 | 80 | 92 | 100 | 98 | 80 | 112 |
| | RR | 16 | 18 | 24 | 16 | 22 | 20 | 22 | 20 | 28 |
| 3 | HR | 92 | 66 | 100 | 88 | 104 | 100 | 100 | 88 | 112 |
| | RR | 18 | 18 | 28 | 20 | 22 | 24 | 24 | 20 | 24 |
| 3 | HR | 84 | 84 | 76 | 72 | 88 | 84 | 104 | 84 | 100 |
| | RR | 18 | 16 | 24 | 18 | 18 | panting | 26 | 20 | 24 |
| 2 | HR | 96 | 84 | 100 | 100 | 96 | 112 | 108 | 112 | 128 |
| | RR | 20 | 18 | 28 | 26 | 20 | 24 | 22 | 20 | 20 |
| 3 | HR | 81 | 100 | 96 | 76 | 118 | 96 | 100 | 96 | 96 |
| | RR | 32 | 24 | 28 | 20 | 28 | 28 | 28 | 20 | 24 |

Figure 1:
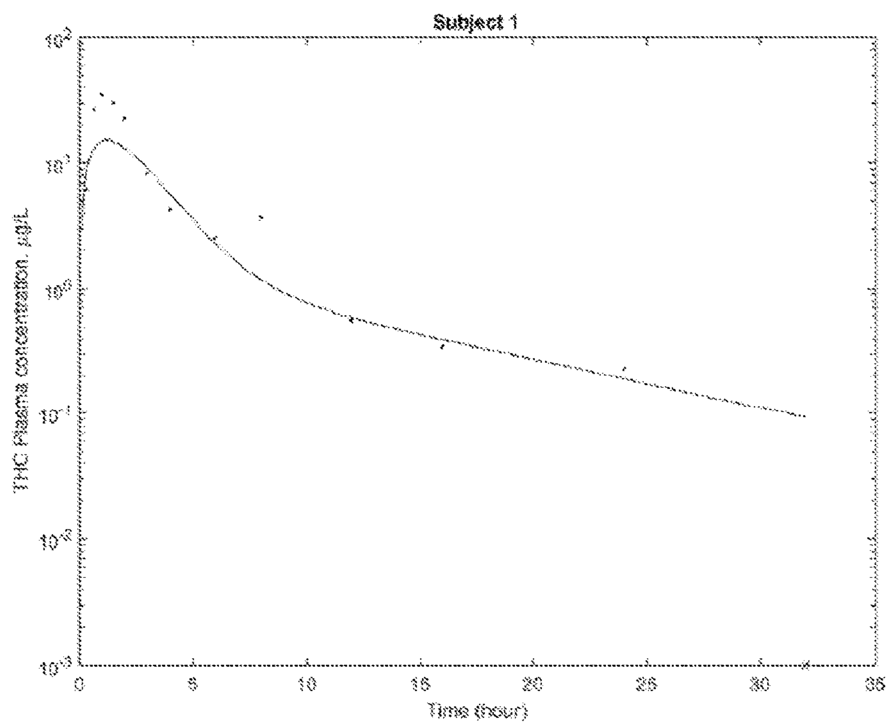
FIG. 1 shows a chart of the pharmacokinetic profile of THC in a first canine subject following administration of a composition of the invention.
Figure 2:
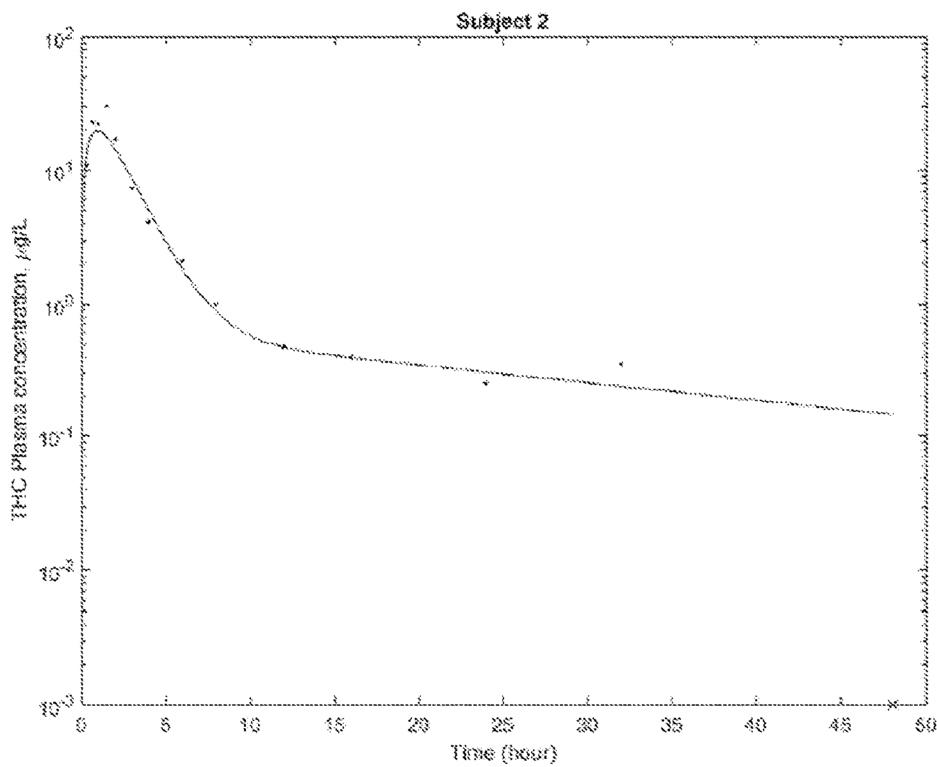
FIG. 2 shows a chart of the pharmacokinetic profile of THC in a second canine subject following administration of a composition of the invention.
Figure 3:
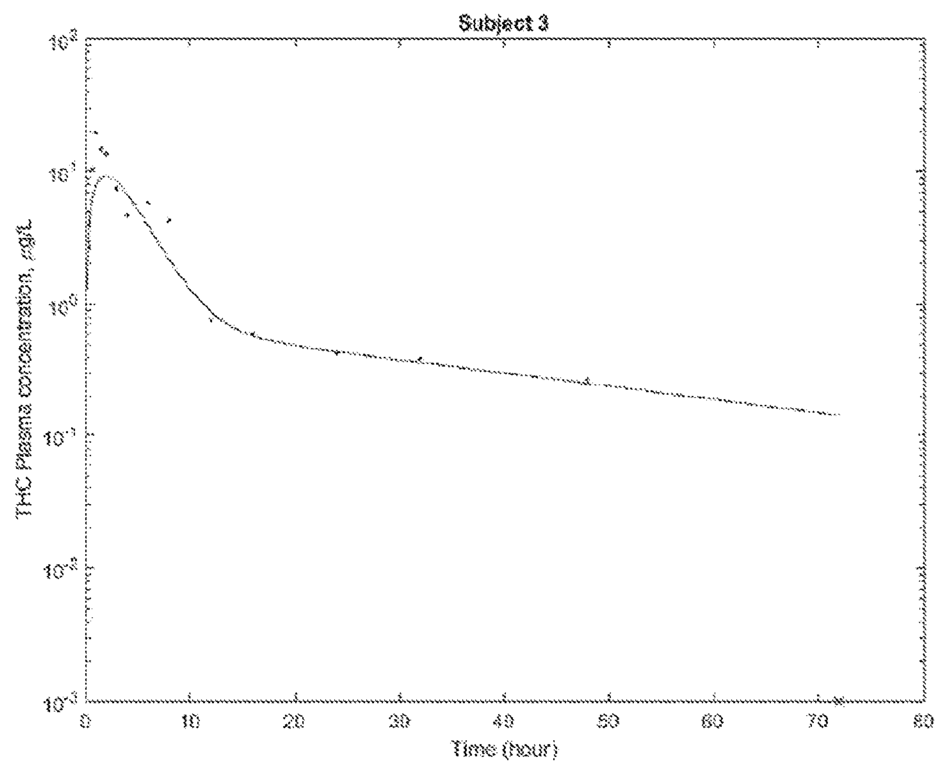
FIG. 3 shows a chart of the pharmacokinetic profile of THC in a third canine subject following administration of a composition of the invention.
Figure 4:
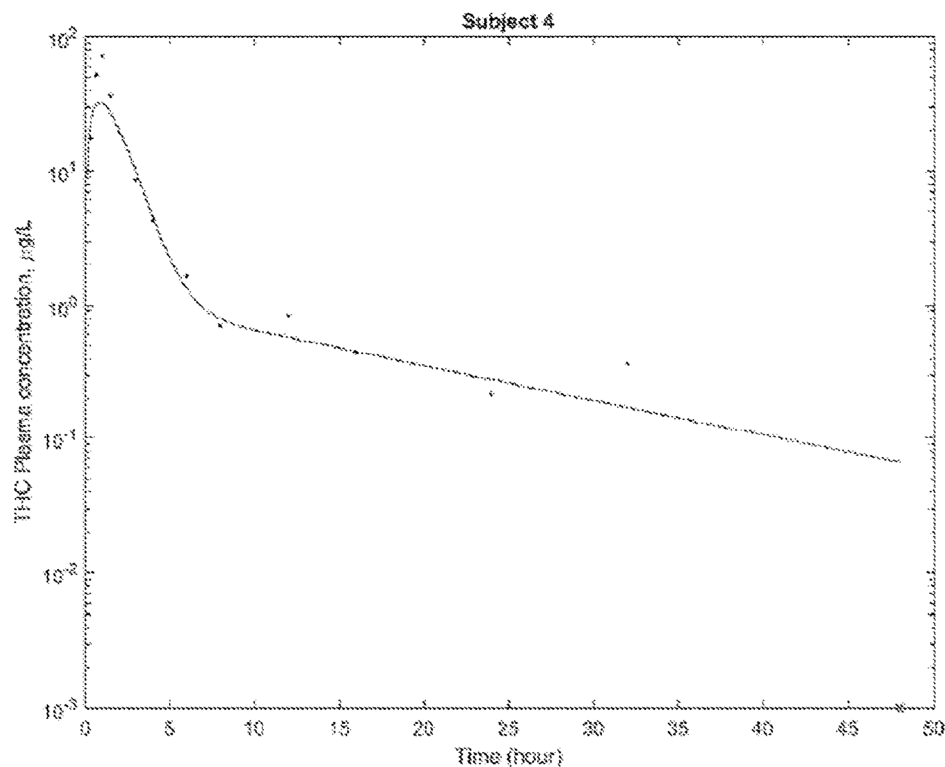
FIG. 4 shows a chart of the pharmacokinetic profile of THC in a fourth canine subject following administration a composition of the first aspect of the invention.
Figure 5:
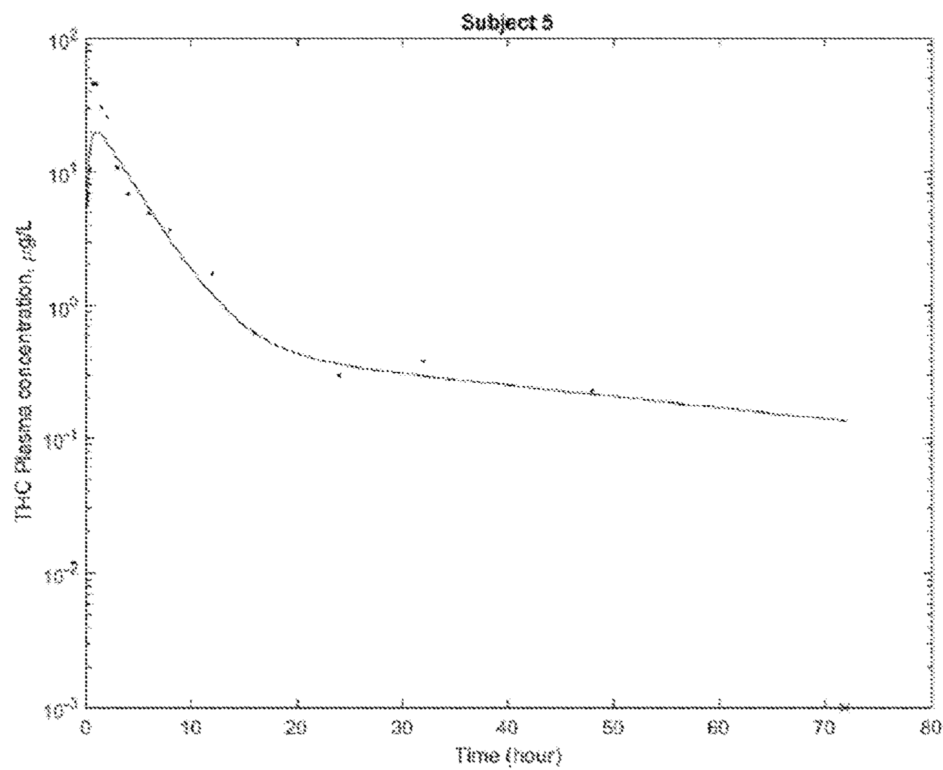
FIG. 5 shows a chart of the pharmacokinetic profile of THC in a fifth canine subject following administration of a composition of the invention.
Figure 6:
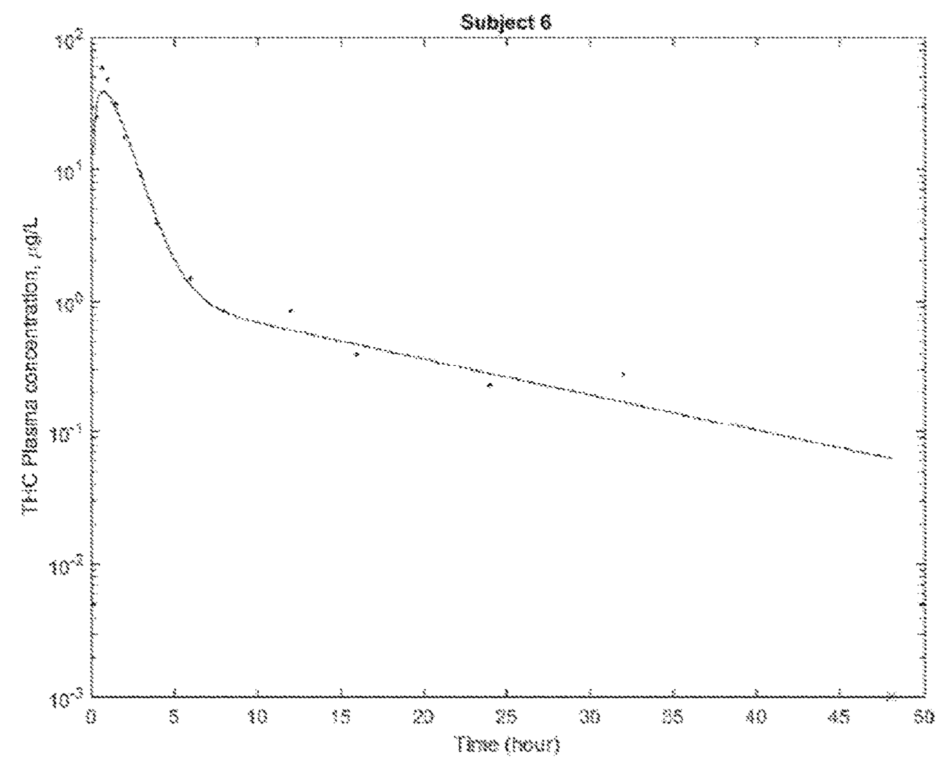
FIG. 6 shows a chart of the pharmacokinetic profile of THC in a sixth canine subject following administration of a composition of the invention.
Figure 7:
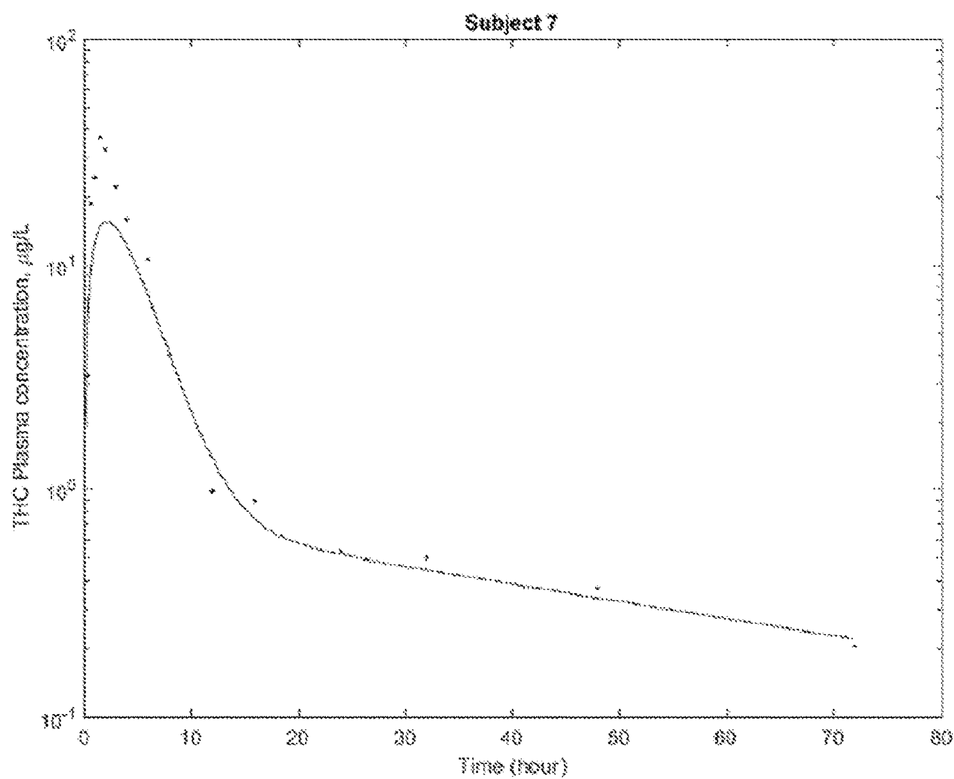
FIG. 7 shows a chart of the pharmacokinetic profile of THC in a seventh canine subject following administration of a composition of the invention.
Figure 8:
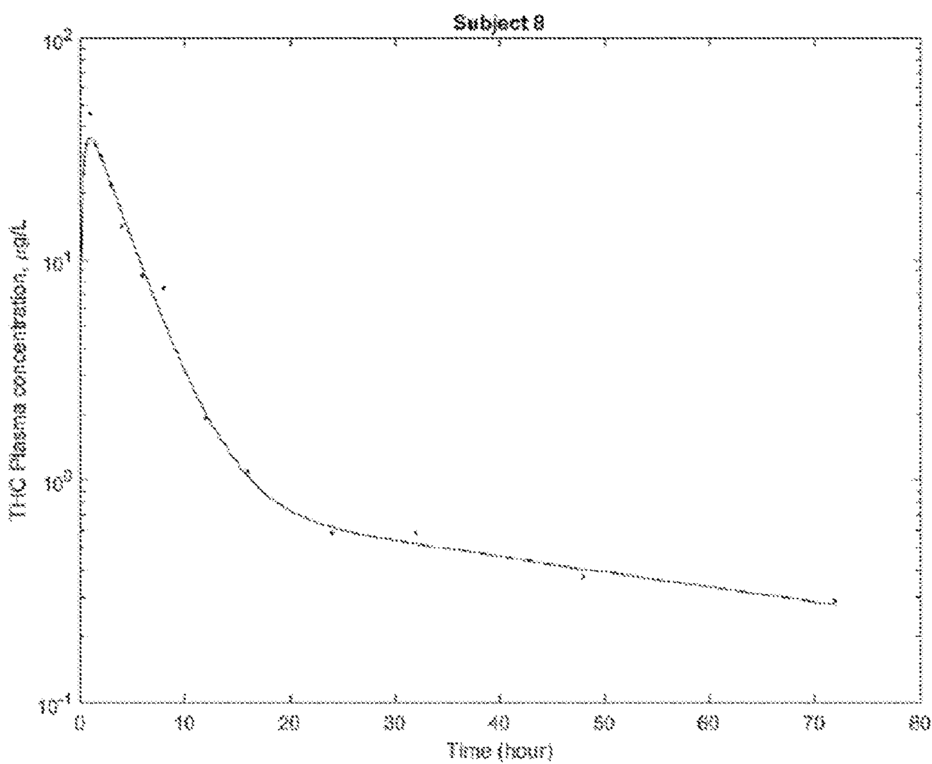
FIG. 8 shows a chart of the pharmacokinetic profile of THC in an eighth canine subject following administration of a composition of the invention.
Figure 9:
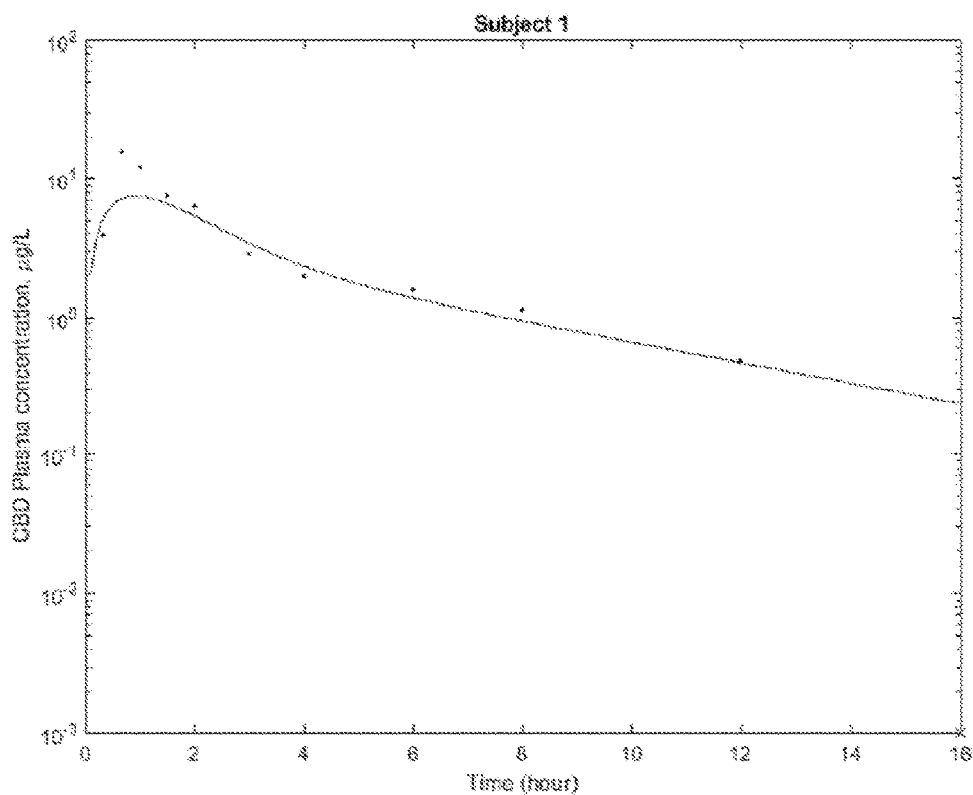
FIG. 9 shows a chart of the pharmacokinetic profile of CBD in the first canine subject following administration of a composition of the invention.
Figure 10:
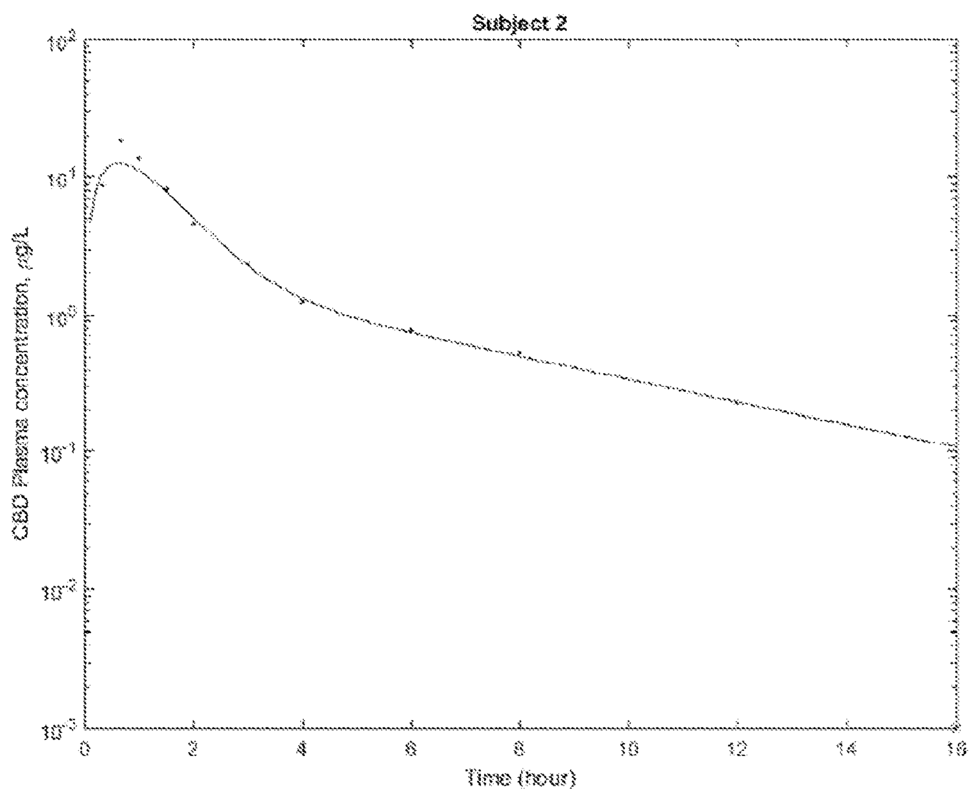
FIG. 10 shows a chart of the pharmacokinetic profile of CBD in the second canine subject following administration of a composition of the invention.
Figure 11:
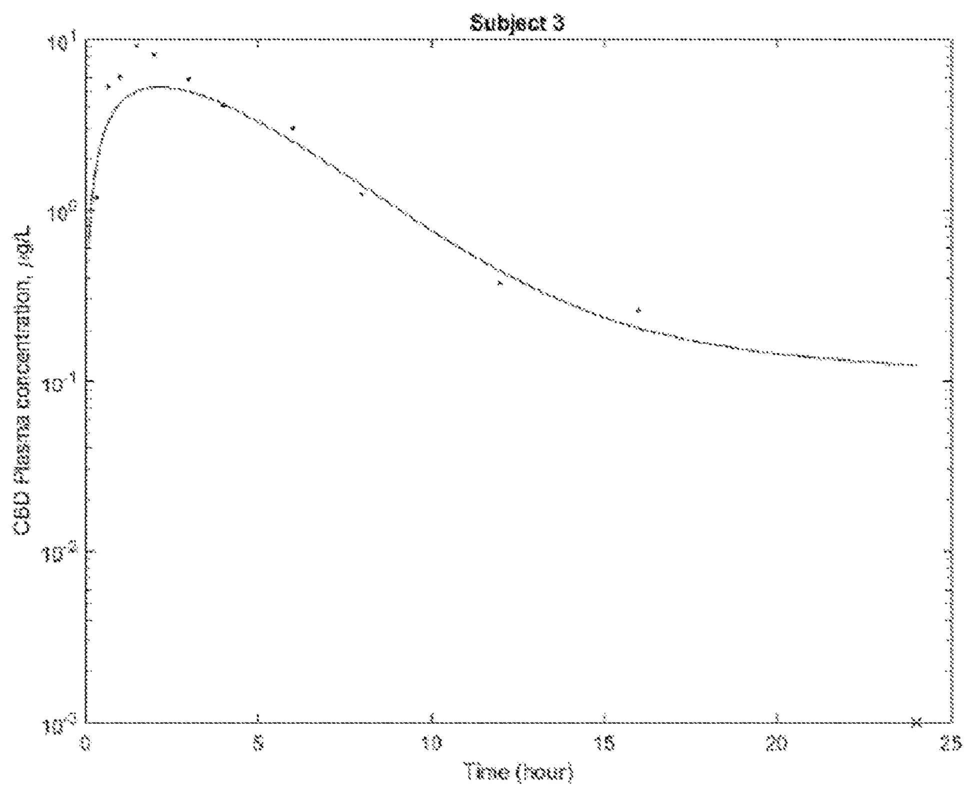
FIG. 11 shows a chart of the pharmacokinetic profile of CBD in the third canine subject following administration of a composition of the invention.
Figure 12:
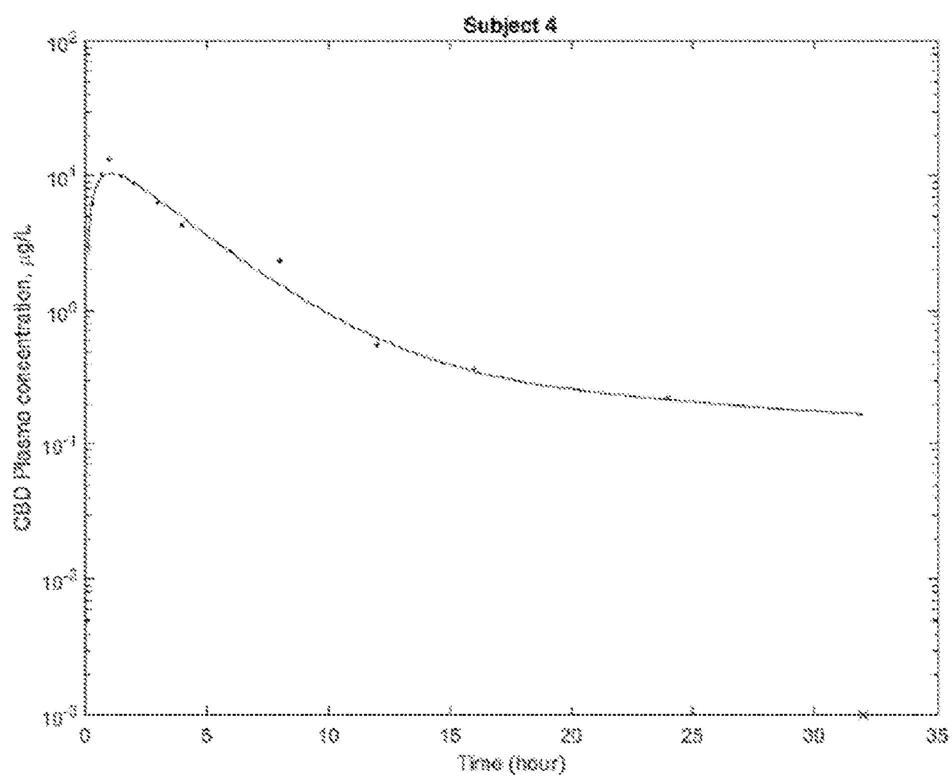
FIG. 12 shows a chart of the pharmacokinetic profile of CBD in the fourth canine subject following administration of a composition of the invention.
Figure 13:
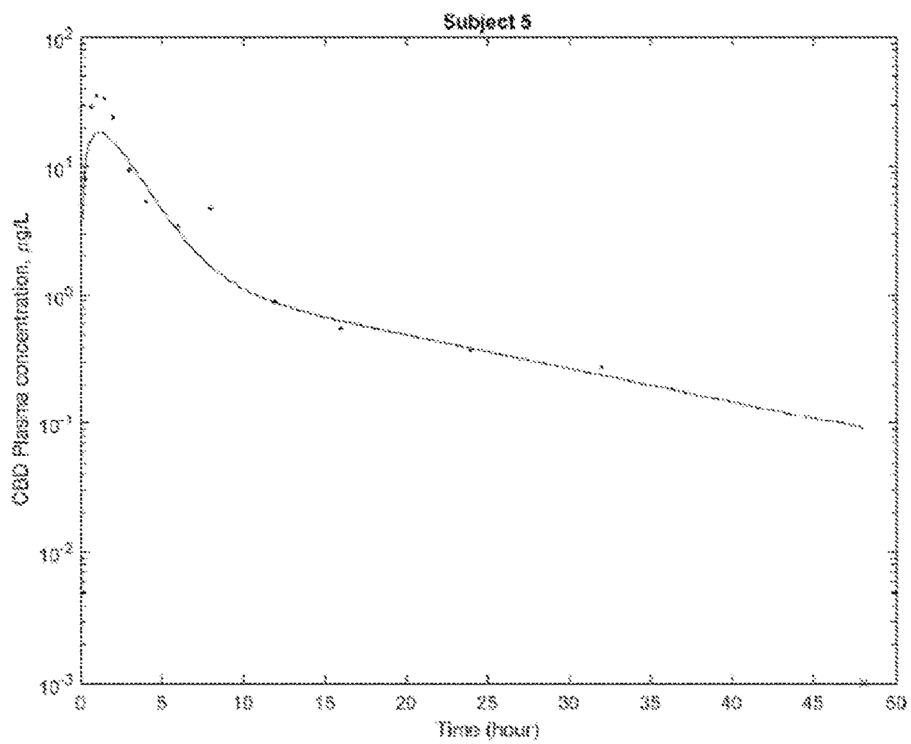
FIG. 13 shows a chart of the pharmacokinetic profile of CBD in the fifth canine subject following administration of a composition of the invention.
Figure 14:
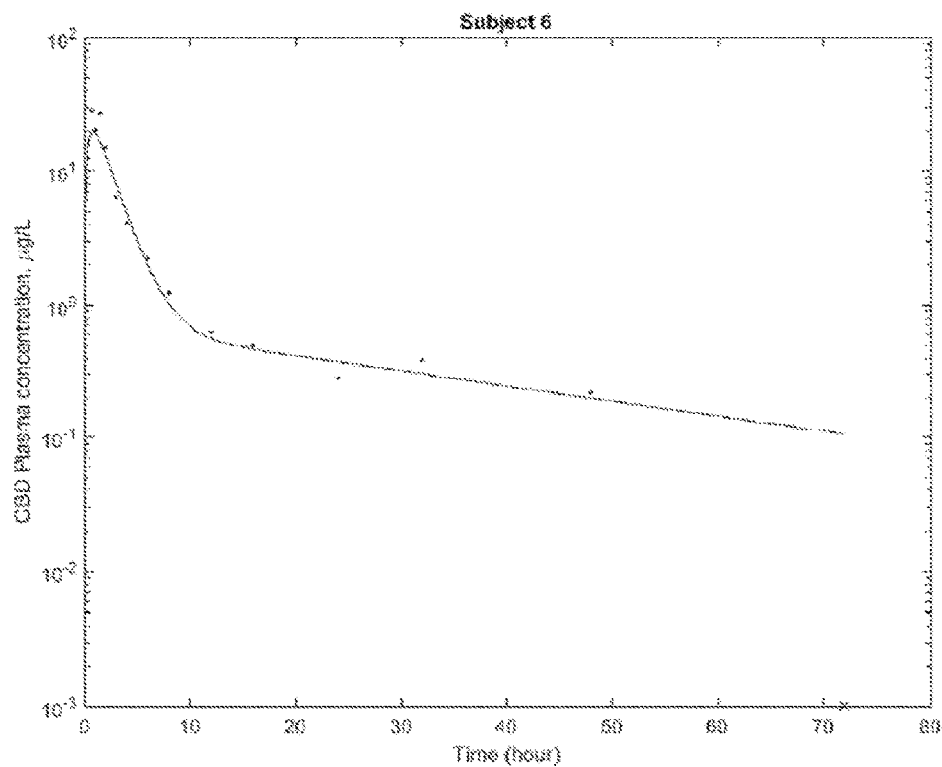
FIG. 14 shows a chart of the pharmacokinetic profile of CBD in the sixth canine subject following administration of a composition of the invention.
Figure 15:
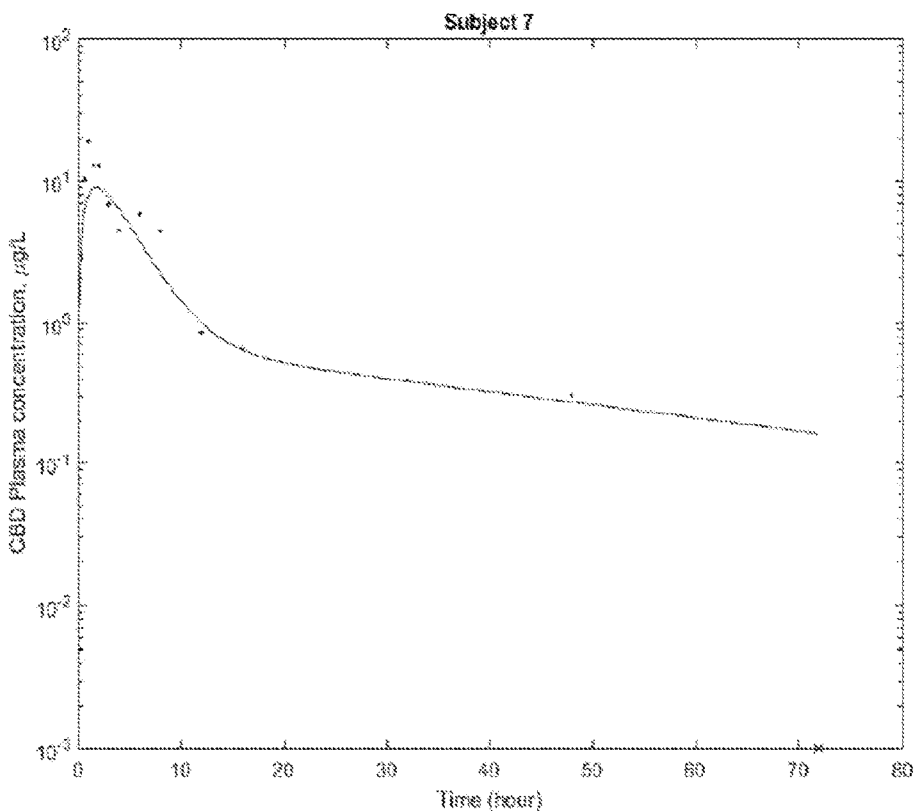
FIG. 15 shows a chart of the pharmacokinetic profile of CBD in the seventh canine subject following administration of a composition of the invention.
Figure 16:
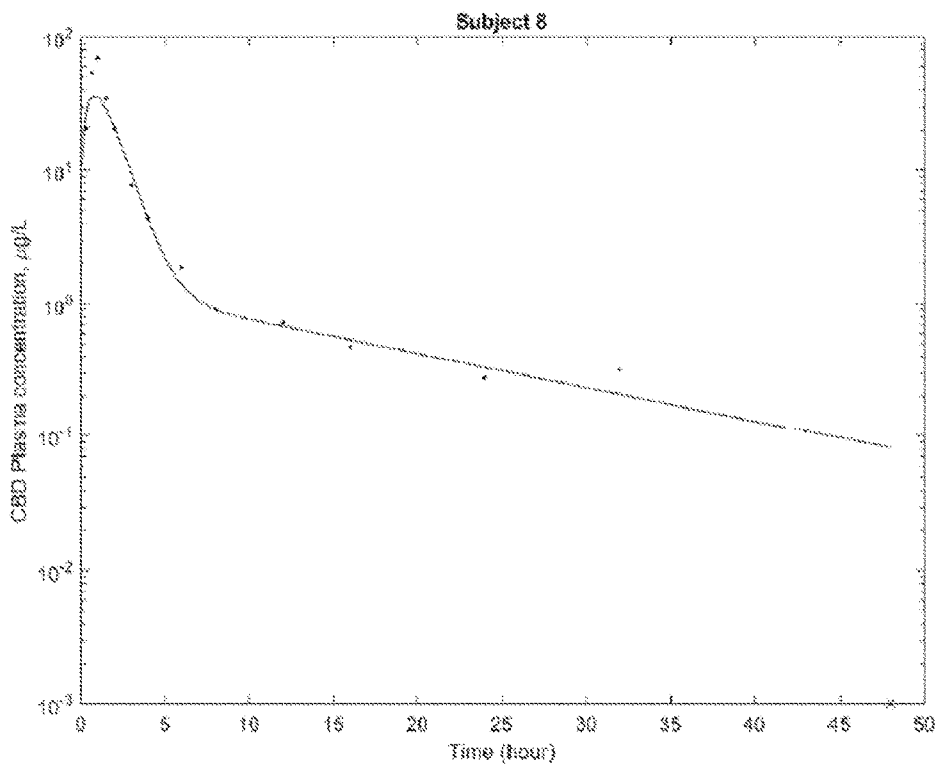
FIG. 16 shows a chart of the pharmacokinetic profile of CBD in the eighth canine subject following administration of a composition of the invention.
Figure 17:
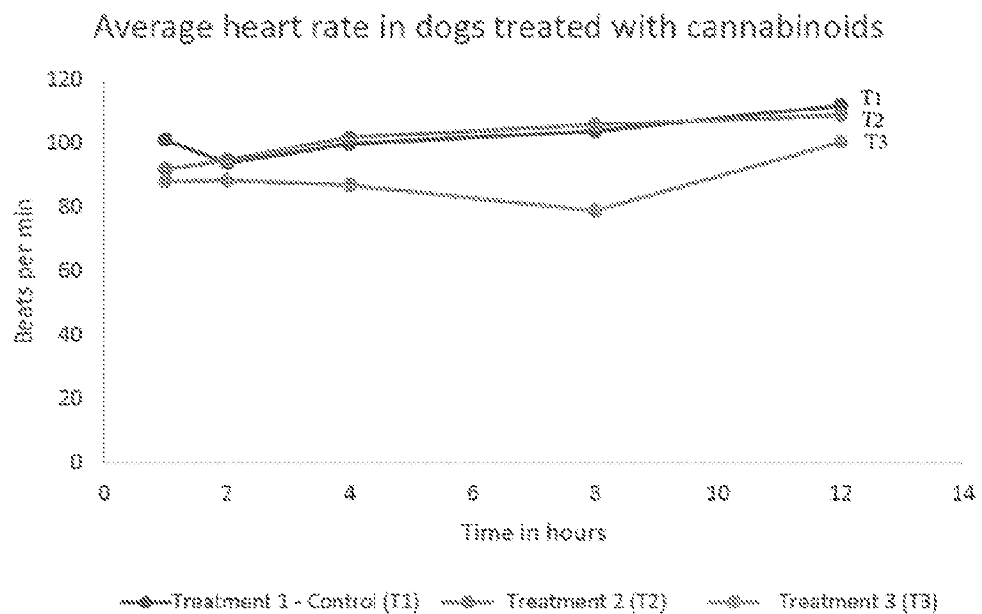
FIG. 17 shows a plot of the heart rates of the 3 treatment groups (11 dogs) for the 12 hours post administration.
Figure 18:
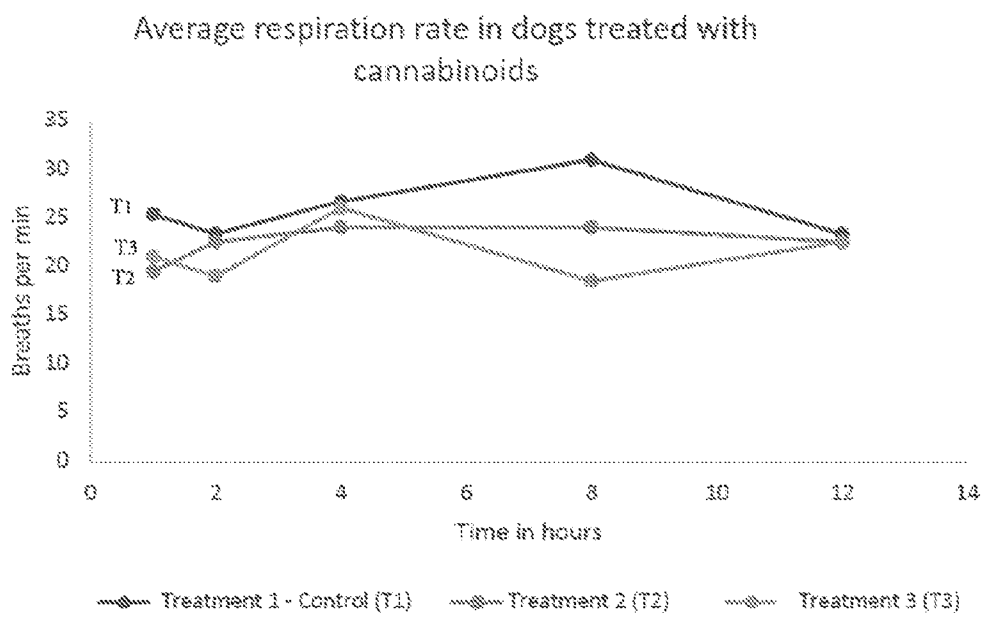
FIG. 18 shows a plot of the respiratory rates of the 3 treatment groups (11 dogs) for the 12 hours post administration.
Figure 19:
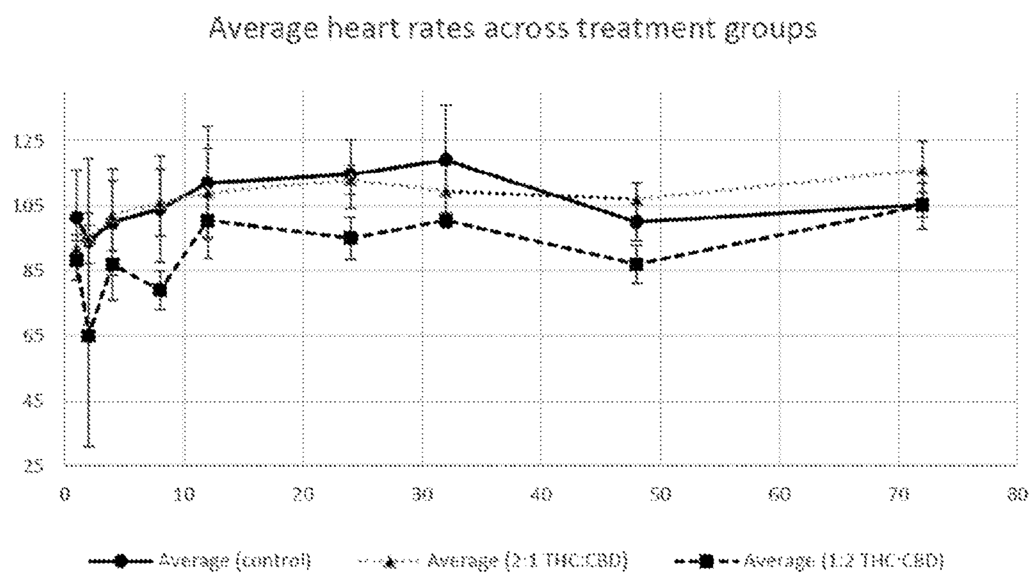
FIG. 19 shows a plot of the heart rates of the 3 treatment groups (11 dogs) for the 72 hours post administration.
Figure 20:
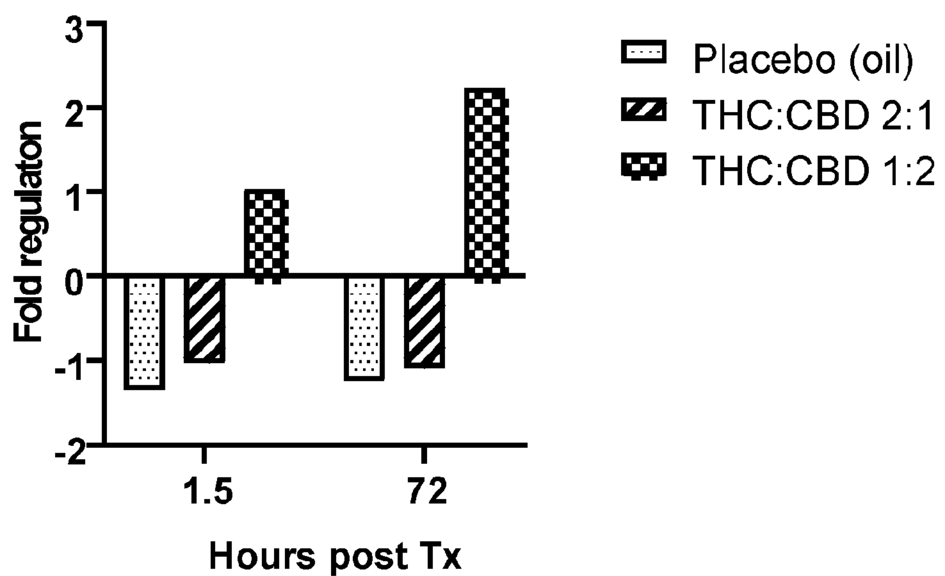
FIG. 20 shows a chart showing the change in chemokine ligand 5 gene (CCL5) expression at 1.5 h and 72 h in blood following administration of (i) medium-chain triglyceride (MCT) oil; (ii) a composition of the invention comprising a 2:1 ratio by weight of THC:CBD and MCT oil; and (iii) a composition of the invention comprising a 1:2 ratio by weight of THC:CBD and MCT oil.
Figure 21:
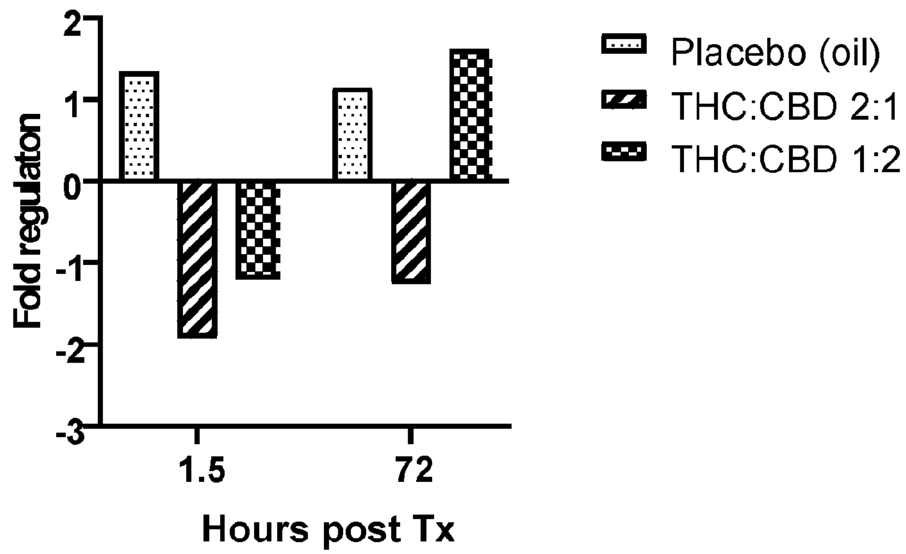
FIG. 21 shows a chart showing the change in cerebellar degeneration-related protein 2 gene (CDR2) expression at 1.5 h and 72 h in blood following administration of (i) MCT oil; (ii) a composition of the invention comprising a 2:1 ratio by weight of THC:CBD and MCT oil; and (iii) a composition of the invention comprising a 1:2 ratio by weight of THC:CBD and MCT oil.
Figure 22:
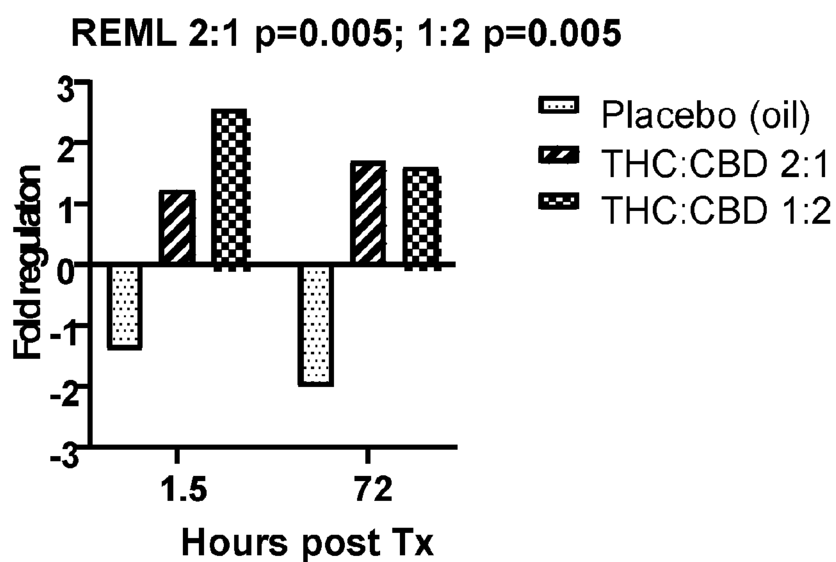
FIG. 22 shows a chart showing the change in cannabinoid receptor 2 gene (CNR2) expression at 1.5 h and 72 h in blood following administration of (i) MCT oil; (ii) a composition of the invention comprising a 2:1 ratio by weight of THC:CBD and MCT oil; and (iii) a composition of the invention comprising a 1:2 ratio by weight of THC:CBD and MCT oil.
Figure 23:
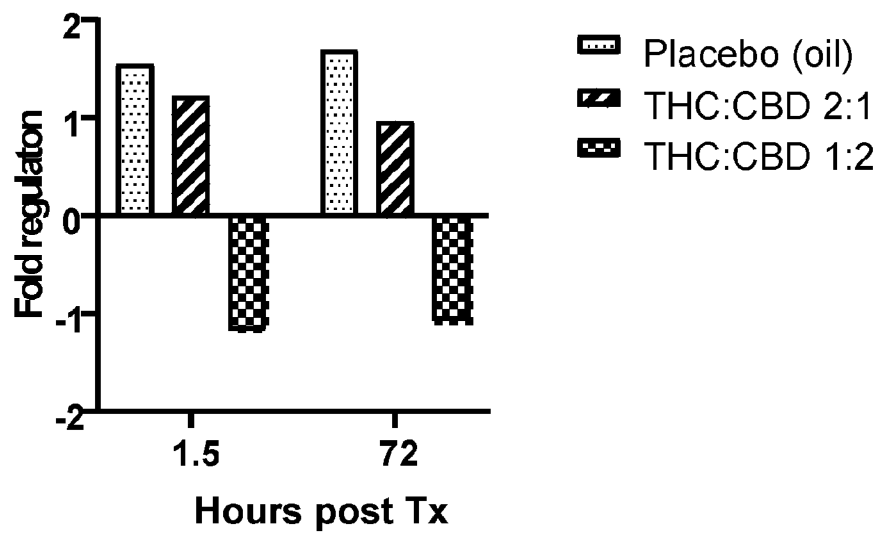
FIG. 23 shows a chart showing the change in interleukin 8 gene (CXCL8) expression at 1.5 h and 72 h in blood following administration of (i) MCT oil; (ii) a composition of the invention comprising a 2:1 ratio by weight of THC:CBD and MCT oil; and (iii) a composition of the invention comprising a 1:2 ratio by weight of THC:CBD and MCT oil.
Figure 24:
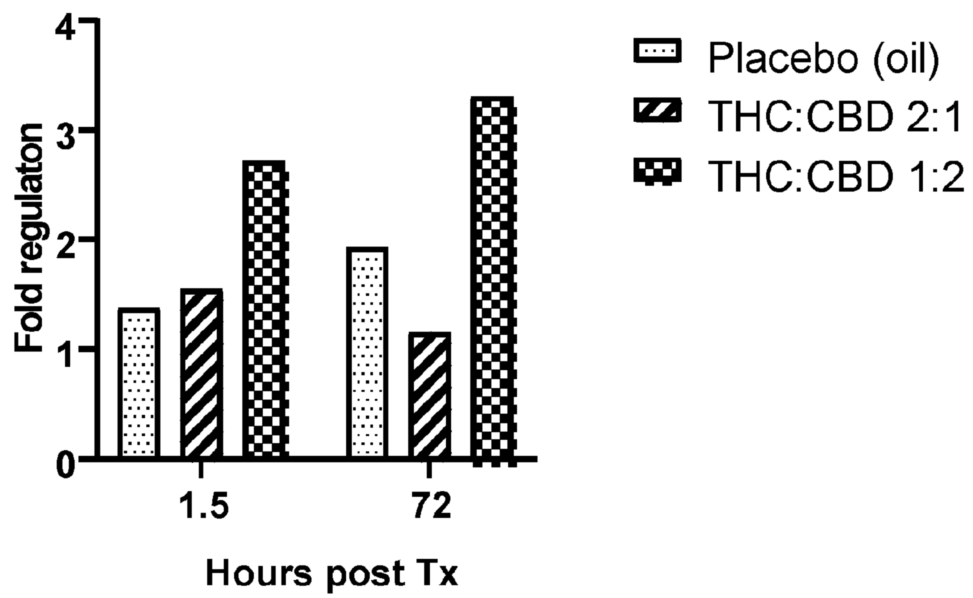
FIG. 24 shows a chart showing the change in adrenoceptor beta 2 gene (ADRB2) expression at 1.5 h and 72 h in blood following administration of (i) MCT oil; (ii) a composition of the invention comprising a 2:1 ratio by weight of THC:CBD and MCT oil; and (iii) a composition of the invention comprising a 1:2 ratio by weight of THC:CBD and MCT oil.

The heart rate data plotted in FIG. 17 shows that there was little difference between the control group (TG1) and (TG2) but there did seem to be a difference with TG3 which received the lower THC dose than then CBD dose. In the respiratory rate graph in FIG. 18, TG3 is also shown as being somewhat lower levels to both TG1 (control) and TG2 (increased CBD). This shows that the concentrations of cannabinoids seen in the study are having physiological effects, up to 12 hours after administration.

Example 2

The composition comprises a combination of THC and CBD in a carrier oil. The THC and CBD were prepared into separate stock solutions in MCT oil at known concentrations and then a portion of each stock solution was mixed to a pre-determined desired ratio of 2:1 THC to CBD. This ratio of cannabinoids is in a MCT oil. Three compositions were prepared comprising a combined concentration of THC and CBD of 0.9% (i.e. about 0.6% THC and about 0.3% CBD), 1.9% and 2.7%.

Example 3

The composition comprises a combination of THC and CBD in a carrier oil. The THC and CBD were prepared into separate stock solutions in MCT oil at known concentrations and then a portion of each stock solution was mixed to a pre-determined desired ratio of 1:2 THC to CBD. This ratio of cannabinoids is in a MCT oil. Three compositions were prepared comprising a combined concentration of THC and CBD of 0.9% (i.e. about 0.3% THC and about 0.6% CBD), 1.9% and 2.7%.

Example 4

This Example describes a gene expression analysis undertaken on the blood samples taken during the study described in Example 1. The gene expression analysis was conducted on blood samples taken prior to treatment, 1.5 h after administration and 72 h after administration.

Dog blood drawn and 100 µl blood immediately added to a labelled room temperature RNAprotect Animal Blood Tube which has been closed and gently inverted 8-10 times, then stored upright at 15-25° C. for 2 hours prior to storing in −20° C. freezer and then shipment on dry ice.

RNA extracted from whole blood collected in RNAprotect Animal Blood tubes using RNeasy Protect Animal Blood kit. RNA was eluted in 30 µl into eppendorf tubes and sealed with parafilm. RNA quality and concentration are determined by using a Nanodrop spectrophotometer to measure the concentration and OD260/280 values of the samples and an Agilent RNA TapeScreen to check RNA quality.

For the integrity measurement, 1 µl of the total RNA was analysed with a RNA ScreenTape using an Agilent TapeStation.

Gene quantification was carried out using real-time reverse transcription polymerase chain reaction (RT-PCR) combined with microarray analysis, using a $RT^2$ Profiler PCR Array. Experimental RNA samples were converted into first strand cDNA. Then, the cDNA templates were mixed with a ready-to-use $RT^2$ qPCR Master Mix and aliquoted into each well of the same plate containing pre-dispensed gene specific primer sets. After qPCR relative expression is determined with the ddCt method. Results are shown in FIGS. 20-24.

Complimentary deoxyribonucleic acid (cDNA) synthesis was carried out using a QIAGEN $RT^2$ First Strand Kit (Catalog #330401). Or, for samples containing a low RNA yield, the $RT^2$ PreAMP reaction was used before qPCR analysis.

Example 5

This Example describes biomarker analysis undertaken on the blood samples taken during the study described in Example 1. The analysis was conducted on blood samples taken prior to treatment, 1.5 h after administration and 72 h after administration.

Biomarker concentration was determined using a magnetic bead panel comprising magnetic beads loaded with antibodies for each biomarker of interest.

Example 6

This Examples describes a study involving up to about 45 dogs, approximately balanced by sex, of various breeds and ages with osteoarthritis (OA) in any joint(s) resulting in impairment of mobility and/or signs of pain.

Treatment allocation is double-blinded placebo-controlled and randomised. Dogs are diagnosed with OA by a veterinarian. Dogs have been on a reasonably stable treatment regime (treatments listed). Dogs are fed the same recorded type and amount of diet for prior to and during study duration. No other oil-based OA treatments or supportive therapies will be used for 2 weeks before and during the study.

Dogs with OA are divided into four groups. Neither owner nor clinician will be aware of the nature of the supplementation.

1. Treatment group 1 (placebo group—15 dogs) will receive olive oil, twice daily orally at a dose of 1 ml/10 kg twice daily for eight weeks.
2. Treatment group 2 (CPAT01—0.75× group—15 dogs) will receive CannPal AUS; CPAT01 blended oil) orally at a dose of 0.54 mg/kg twice daily on food for eight weeks.
3. Treatment group 3 (CPAT01—1.5× group—15 dogs) will receive CannPal AUS; CPAT01 blended oil) orally at a dose of 1.08 mg/kg twice daily on food for eight weeks.
4. Treatment group 4 (CPAT01—2.5× group—15 dogs) will receive CannPal AUS; CPAT01 blended oil) orally at a dose of 1.8 mg/kg twice daily on food for eight weeks.

Dogs are enrolled with the written consent of owners. All procedures comply with applicable Animal Ethics Committee (AEC) requirements and Australian Animal Care laws and regulations. At regular intervals (for example at Week −2, 0, 2, 4, 6 and 8) owners filled out a Canine Brief Pain Inventory (CPBI), Canine Orthopaedic Index (COI) and Hudson Activity Scale (or similar) which are validated owner questionnaires to assess how dogs with OA are progressing or deteriorating. Visits to the veterinarian at about Week 0, 4 and 8 include a veterinary subjective evaluation and blood sampling. Blood samples are tested for CBC/biochemistry to monitor hepatic and renal enzymes (urea, creatinine, ALP, ALT) and white blood cells. Plasma cannabinoid (CBD and THC) assays are also performed from blood at each visit.

The invention claimed is:

1. A method of treating pain, inflammation and/or anxiety in a canine subject in need thereof, comprising orally administering to the canine subject an effective amount of a liquid composition comprising:

a combination of $\Delta^9$-tetrahydrocannabinol (THC) and cannabidiol (CBD) in a ratio by weight of THC:CBD of from 1:1.5 to 1:30, and an oral delivery system comprising a fatty acid;

wherein administration of the liquid composition controls a heart rate of the canine subject.

2. The method of claim 1, wherein the ratio by weight of THC:CBD is from 1:1.5 to 1:2.4.

3. The method of claim 2, wherein the ratio by weight of THC:CBD is about 1:about 2.

4. The method of claim 1, wherein the concentration of CBD in the liquid composition is at least about 0.2%.

5. The method of claim 4, wherein the concentration of CBD in the liquid composition is up to about 7.5%.

6. The method of claim 1, wherein the concentration of CBD in the liquid composition is up to about 7.5%.

7. The method of claim 1, wherein the concentration of THC in the liquid composition is at least about 0.1%.

8. The method of claim 7, wherein the concentration of THC in the liquid composition is up to about 6.5%.

9. The method of claim 1, wherein the concentration of THC in the liquid composition is up to about 6.5%.

10. The method of claim 3, comprising a combined concentration of THC and CBD from 0.9% to 2.7%.

11. The method of claim 1, wherein the oral delivery system comprises a medium-chain triglyceride (MCT) oil.

12. The method of claim 1, wherein the liquid composition further comprises an antioxidant to delay or prevent oxidation of the fatty acid.

13. The method of claim 12, wherein the antioxidant is ascorbic acid, butylated hydroxyanisole, butylated hydroxytoluene (BHT), propyl gallate, a tocopherol or a combination thereof.

14. The method of claim 1, wherein the liquid composition is provided in the form of a food product comprising the liquid composition.

15. The method of claim 1, wherein the average heart rate of the canine subject is lowered for at least about 2 h following administration.

16. The method of claim 1, wherein administration of the liquid composition downregulates expression of interleukin 8 gene (CXCL8, as shown in SEQ ID NO:1) and/or upregulates expression of chemokine (C-C motif) ligand 5 gene (CCL5, as shown in SEQ ID NO:4) and/or upregulates expression of cannabinoid Receptor 2 gene (CNR2, as shown in SEQ ID NO:3) and/or upregulates expression of adrenoreceptor beta 2 gene (ADRB2, as shown in SEQ ID NO:5).

* * * * *